US012617870B2

(12) United States Patent
Lee et al.

(10) Patent No.: US 12,617,870 B2
(45) Date of Patent: May 5, 2026

(54) METHODS OF REVERSING TICAGRELOR ACTIVITY

(71) Applicant: SFJ Pharmaceuticals X, LTD., Pleasanton, CA (US)

(72) Inventors: John Lee, Malvern, PA (US); David James Ballance, Malvern, PA (US)

(73) Assignee: SFJ Pharmaceutical X, LTD., Pleasanton, CA (US)

( * ) Notice: Subject to any disclaimer, the term of this patent is extended or adjusted under 35 U.S.C. 154(b) by 1059 days.

(21) Appl. No.: 17/278,075

(22) PCT Filed: Sep. 20, 2019

(86) PCT No.: PCT/US2019/052173
§ 371 (c)(1),
(2) Date: Mar. 19, 2021

(87) PCT Pub. No.: WO2020/061465
PCT Pub. Date: Mar. 26, 2020

(65) Prior Publication Data
US 2021/0347915 A1    Nov. 11, 2021

Related U.S. Application Data

(60) Provisional application No. 62/836,373, filed on Apr. 19, 2019, provisional application No. 62/806,225, filed on Feb. 15, 2019, provisional application No. 62/733,892, filed on Sep. 20, 2018.

(51) Int. Cl.
| | |
|---|---|
| *C07K 16/44* | (2006.01) |
| *A61P 7/04* | (2006.01) |
| *A61P 39/02* | (2006.01) |
| *A61K 39/00* | (2006.01) |

(52) U.S. Cl.
CPC .............. *C07K 16/44* (2013.01); *A61P 7/04* (2018.01); *A61P 39/02* (2018.01); *A61K 2039/505* (2013.01); *A61K 2039/54* (2013.01); *A61K 2039/545* (2013.01); *C07K 2317/55* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,223,409 A | 6/1993 | Ladner et al. | |
| 5,403,484 A | 4/1995 | Ladner et al. | |
| 5,427,908 A | 6/1995 | Dower et al. | |
| 5,516,637 A | 5/1996 | Huang et al. | |
| 5,571,698 A | 11/1996 | Ladner et al. | |
| 5,580,717 A | 12/1996 | Dower et al. | |
| 5,658,727 A | 8/1997 | Barbas et al. | |
| 5,698,426 A | 12/1997 | Huse | |
| 5,733,743 A | 3/1998 | Johnson et al. | |
| 5,739,277 A | 4/1998 | Presta et al. | |
| 5,750,753 A | 5/1998 | Kimae et al. | |
| 5,780,225 A | 7/1998 | Wigler et al. | |
| 5,821,047 A | 10/1998 | Garrard et al. | |
| 5,969,108 A | 10/1999 | McCafferty et al. | |
| 6,525,060 B1 | 2/2003 | Hardern et al. | |
| 6,821,505 B2 | 11/2004 | Ward | |
| 7,083,784 B2 | 8/2006 | Dall'Acqua et al. | |
| 7,135,180 B2 | 11/2006 | Truong-Le | |
| 7,258,873 B2 | 8/2007 | Truong-Le et al. | |
| 7,326,681 B2 | 2/2008 | Gerngross | |
| 7,378,110 B2 | 5/2008 | Truong-Le et al. | |
| 9,982,061 B2 | 5/2018 | Buchanan et al. | |
| 10,487,154 B2 | 11/2019 | Buchanan et al. | |
| 10,954,308 B2 | 3/2021 | Buchanan et al. | |
| 11,773,186 B2 | 10/2023 | Buchanan et al. | |
| 2002/0098193 A1 | 7/2002 | Ward | |
| 2003/0190311 A1 | 10/2003 | Dall | |
| 2004/0042971 A1 | 3/2004 | Truong-Le et al. | |
| 2004/0042972 A1 | 3/2004 | Truong-Le et al. | |
| 2008/0066200 A1 | 3/2008 | Dickey et al. | |
| 2009/0197834 A1 | 8/2009 | Koga et al. | |
| 2014/0286969 A1* | 9/2014 | Tschoepe ............... A61K 31/40 | |
| | | | 424/178.1 |
| 2016/0108084 A1* | 4/2016 | Gruber ..................... C07K 1/22 | |
| | | | 562/512 |
| 2016/0130366 A1 | 5/2016 | Buchanan et al. | |
| 2016/0176912 A1 | 6/2016 | Cosgrove et al. | |
| 2018/0055940 A1 | 3/2018 | Ma et al. | |
| 2018/0319897 A1 | 11/2018 | Buchanan et al. | |
| 2019/0077882 A1 | 3/2019 | Buchanan et al. | |

(Continued)

FOREIGN PATENT DOCUMENTS

| | | |
|---|---|---|
| CA | 2963166 A1 | 4/2016 |
| CN | 1128801 C | 11/2003 |

(Continued)

OTHER PUBLICATIONS

Almquist, J., et al., "Unraveling the Pharmacokinetic Interaction of Ticagrelor and MEDI2452 (Ticagrelor Antidote) by Mathematical Modeling", CPT: Pharmacometrics & Systems Pharmacology (2016); 5(6): 313-323.

Ames, R. S., et al., "Conversion of murine Fabs isolated from a combinatorial phage display library to full length immunoglobulins," Journal of Immunological Methods (Aug. 18, 1995); 184(2): 177-186.

Amsterdam, E. A., et al., "2014 AHA/ACC Guideline for the Management of Patients With Non-ST-Elevation Acute Coronary Syndromes", A Report of the American College of Cardiology/ American Heart Association Task Force on Practice Guidelines, J Am Coll Cardiol (Dec. 23, 2014); 64(24): e139-e228.

Aradi, Dániel, et al. "Bleeding and stent thrombosis on P2Y12-inhibitors: collaborative analysis on the role of platelet reactivity for risk stratification after percutaneous coronary intervention", European Heart Journal (2015); 36(27): 1762-1771.

(Continued)

*Primary Examiner* — Brad Duffy
(74) *Attorney, Agent, or Firm* — Morrison & Foerster LLP

(57) ABSTRACT

The present disclosure provides a method of reversing ticagrelor-associated bleeding in a patient by administering an antibody or fragment thereof that binds to ticagrelor.

40 Claims, 22 Drawing Sheets

Specification includes a Sequence Listing.

(56) References Cited

U.S. PATENT DOCUMENTS

| | | |
|---|---|---|
| 2021/0371546 A1 | 12/2021 | Buchanan et al. |
| 2023/0192895 A1 | 6/2023 | Lee |
| 2024/0101712 A1 | 3/2024 | Buchanan |

FOREIGN PATENT DOCUMENTS

| | | |
|---|---|---|
| CN | 101646690 A | 2/2010 |
| JP | H03154867 A | 7/1991 |
| JP | 2017517307 A | 6/2017 |
| JP | 6799530 B2 | 12/2020 |
| JP | 7478975 B | 4/2024 |
| TW | I707870 B | 10/2020 |
| WO | WO-9002809 A1 | 3/1990 |
| WO | WO-9110737 A1 | 7/1991 |
| WO | WO-9201047 A1 | 1/1992 |
| WO | WO-9218619 A1 | 10/1992 |
| WO | WO-9222324 A1 | 12/1992 |
| WO | WO-9311236 A1 | 6/1993 |
| WO | WO-9515982 A2 | 6/1995 |
| WO | WO-9520401 A1 | 8/1995 |
| WO | WO-9713844 A1 | 4/1997 |
| WO | WO-9905143 A1 | 2/1999 |
| WO | WO-0034283 A1 | 6/2000 |
| WO | 2008036341 A2 | 3/2008 |
| WO | WO-2008142124 A1 | 11/2008 |
| WO | WO-2009018386 A1 | 2/2009 |
| WO | WO-2009058492 A2 | 5/2009 |
| WO | WO-2013006544 A1 | 1/2013 |
| WO | 2013055984 A1 | 4/2013 |
| WO | WO-2016050867 A1 | 4/2016 |
| WO | WO-2018116267 A2 | 6/2018 |
| WO | WO-2018158332 A1 | 9/2018 |
| WO | WO-2020061465 A1 | 3/2020 |
| WO | WO-2022240754 A2 | 11/2022 |

OTHER PUBLICATIONS

Arbabi Ghahroudi, M., et al. "Selection and identification of single domain antibody fragments from camel heavy-chain antibodies." FEBS letters (1997); 414(3): 521-526.

[Author Unknown] "Thermo Scientific Pierce Epitope Tag Antibodies Antibody Target Unconjugated Biotin HRP DyLight 488 Dye DyLight 550 Dye DyLight 650 Dye DyLight 680 Dye", Fisher Scientific, Jan. 9, 2018, [Online] Retrieved from the Internet, https://www.fishersci.de/content/dam/fishersci/en_US/documents/programs/scientific/brochures-and-catalogs/fliers/thermo-scientific-pierce-epitope-tag-antibodies-flyer.pdf, 2 pages.

Bauer, Robert J., "NONMEM Tutorial Part II: Estimation Methods and Advanced Examples", CPT: Pharmacometrics & Systems Pharmacology (2019); 8(8): 538-556.

Bhatt, Deepak L., et al., "Antibody-based ticagrelor reversal agent in healthy volunteers." New England Journal of Medicine (May 9, 2019); 380(19): 1825-1833.

Bhatt, Deepak L., et al., "Antiplatelet and Anticoagulation Therapy for Acute Coronary Syndromes", Circulation Research (2014); 114(12): 1929-1943.

Bhatt, Deepak L., et al., "Clopidogrel and Aspirin versus Aspirin Alone for the Prevention of Atherothrombotic Events", New England Journal of Medicine (Apr. 20, 2006); 354(16): 1706-1717.

Bhatt, Deepak L., et al., "Patients With Prior Myocardial Infarction, Stroke, or Symptomatic Peripheral Arterial Disease in the CHARISMA Trial", Journal of the American College of Cardiology (May 15, 2007); 49(19): 1982-1988.

Bhatt, Deepak L. "Intensifying Platelet Inhibition—Navigating between Scylla and Charybdis", New England Journal of Medicine (Nov. 15, 2007); 357(20): 2078-2081.

Brilinta® (ticagrelor) Tablets: 60 mg and 90 mg, Label; Highlights of Prescribing Information, Patient Information approved by the U.S. Food and Drug Administration; Revised: Sep. 2016 (Sep. 2016), Initial U.S. Approval: 2011, Reference ID: 3989896, Distributed by: AstraZeneca Pharmaceuticals LP, Wilmington, DE 19850 USA, 26 pages.

Brinkmann, U., et al, "A recombinant immunotoxin containing a disulfide-stabilized Fv fragment", Proceeding of the National Academy of Sciences (Aug. 1993), 90(16): 7538-7542.

Brinkmann, U., et al., "Phage display of disulfide-stabilized Fv fragments," Journal of Immunological Methods (May 11, 1995); 182(1): 41-50.

Buchanan, Andrew, et al., "Structural and functional characterization of a specific antidote for ticagrelor", Blood, The Journal of the American Society of Hematology (2015); 125(22): 3484-3490.

Cannon, Christopher P., et al., "Comparison of ticagrelor with clopidogrel in patients with a planned invasive strategy for acute coronary syndromes (PLATO): a randomised double-blind study", The Lancet (Jan. 23, 2010); 375(9711): 283-293.

Capodanno, Davide, et al., "Management of Antiplatelet Therapy in Patients With Coronary Artery Disease Requiring Cardiac and Noncardiac Surgery", Circulation (2013); 128(25): 2785-2798.

Carter, P., et al., "High Level Escherichia coli Expression and Production of a Bivalent Humanized Antibody Fragment", Nature Biotechnology (Feb. 1992); 10: 163-167.

Cattaneo, M., et al., "Adenosine-mediated effects of ticagrelor: evidence and potential clinical relevance", Journal of the American College of Cardiology (Jun. 17, 2014); 63(23): 2503-2509.

Chen, ZM. et al., "Addition of clopidogrel to aspirin in 45,852 patients with acute myocardial infarction: randomised placebo-controlled trial", The Lancet (Nov. 5, 2005); 366(9497): 1607-1621.

Colburn, Wayne A., "Specific Antibodies and Fab Fragments to Alter the Pharmacokinetics and Reverse the Pharmacologic/Toxicologic Effects of Drugs", Drug Metabolism Reviews (1980); 11(2): 223-262.

Crowther, M.A., et al., "Oral vitamin K versus placebo to correct excessive anticoagulation in patients receiving warfarin: a randomized trial", Annals of Internal Medicine (Mar. 3, 2009); 150(5): 293-300.

Dalen, M., et al., "Ticagrelor-Associated Bleeding in a Patient Undergoing Surgery for Acute Type A Aortic Dissection", Journal of Cardiothoracic and Vascular Anesthesia (Oct. 2013); 27(5): e55-e57.

Daramola, O., et al., "A high-yielding CHO transient system: coexpression of genes encoding EBNA-1 and GS enhances transient protein expression", Biotechnology Progress (Jan.-Feb. 2014); 30(1): 132-141.

Dolgin, E., "Antidotes edge closer to reversing effects of new blood thinners," Nature Medicine (Mar. 2013); 19(3): 251.

Douketis, James D., et al., "Perioperative Management of Antithrombotic Therapy: Antithrombotic Therapy and Prevention of Thrombosis, 9th ed: American College of Chest Physicians Evidence-Based Clinical Practice Guidelines", Chest (2012); 141(2): e326S-e350S.

Ducrocq, Gregory, et al., "A History of Stroke/Transient Ischemic Attack Indicates High Risks of Cardiovascular Event and Hemorrhagic Stroke in Patients With Coronary Artery Disease", Circulation (2013); 127(6): 730-738.

Edwards et al., "The remarkable flexibility of the human antibody repertoire; isolation of over one thousand different antibodies to a single protein, BLyS", J Mol Biol. (2003); 334(1): 103-118.

Effient (prasugrel) Tablets: 5 mg and 10 mg (3), Label; Highlights of Prescribing Information, Patient Information approved by the U.S. Food and Drug Administration; Revised: Jul. 2009 (Jul. 2009), Initial U.S. Approval: 2009, Application No. 22-307, Manufactured by: Eli Lilly and Company, Indianapolis, IN, 46285 USA, 17 pages.

Effient (prasugrel) Tablets: 5 mg and 10 mg (3), Label; Highlights of Prescribing Information, Patient Information approved by the U.S. Food and Drug Administration; Revised: Sep. 2011 (Sep. 2011), Initial U.S. Approval: 2009, Reference ID: 3020401, Manufactured by: Eli Lilly and Company, Indianapolis, IN, 46285 USA, 16 pages.

Emsley, P., and Cowtan, K., "Model-Building Tools for Molecular Graphics", Acta Crystallographica Section D, Biological Crystallography (Dec. 2004); 60(12): 2126-2132.

EP Application No. 19863329.9, Extended European Search Report, mailed Jul. 21, 2022, 8 pages.

Faber, C., et al., "Three-dimensional structure of a human Fab with high affinity for tetanus toxoid", Journal of Immunological Methods (Jan. 1998); 3(4): 253-270.

(56) References Cited

OTHER PUBLICATIONS

Fanning, S. W., et al., "An anti-hapten camelid antibody reveals a cryptic binding site with significant energetic contributions from a nonhypervariable loop", Protein Science (Jul. 2011); 20(7): 1196-1207.

Giezen, J. J., V., et al., "Ticagrelor binds to human P2Y{12} independently from ADP but antagonizes ADP-induced receptor signaling and platelet aggregation", Journal of Thrombosis and Haemostasis (Sep. 2009); 7(9): 1556-1565.

Glockshuber, R., et al. "A comparison of strategies to stabilize immunoglobulin Fv-fragments," Biochemistry (1990); 29(6): 1362-1367.

Godier, Anne, et al., "Inefficacy of Platelet Transfusion to Reverse Ticagrelor", New England Journal of Medicine (Jan. 8, 2015); 372(2): 196-197.

Goel et al., "Plasticity within the antigen-combining site may manifest as molecular mimicry in the humoral immune response", J Immunol. (2004); 173(12): 7358-7367.

Gurbel, Paul A., et al., "Randomized Double-Blind Assessment of the Onset and Offset of the Antiplatelet Effects of Ticagrelor Versus Clopidogrel in Patients With Stable Coronary Artery Disease: The Onset/Offset Study", Circulation (2009); 120(25): 2577-2585.

Hansson, E. C., et al., "Effects of ex vivo platelet supplementation on platelet aggregability in blood samples from patients treated with acetylsalicylic acid, clopidogrel, or ticagrelor", Br J Anaesthesia (Mar. 2014); 112(3): 570-575.

Held, Claes, et al., "Ticagrelor versus clopidogrel in patients with acute coronary syndromes undergoing coronary artery bypass surgery: results from the PLATO (Platelet Inhibition and Patient Outcomes) trial", Journal of the American College of Cardiology (2011); 57(6): 672-684.

Hillis, D.L et al., "2011 ACCF/AHA guideline for coronary artery bypass graft surgery: executive summary: a report of the American College of Cardiology Foundation/American Heart Association Task Force on Practice Guidelines", Circulation (2011); 124(23): 2610-2642.

Husted, S. E., et al., "Pharmacokinetics and pharmacodynamics of ticagrelor in patients with stable coronary artery disease: results from the Onset-Offset and Respond studies", Clinical Pharmacokinetics (Jun. 2012); 51(6): 397-409.

International Application No. PCT/EP2015/072606, International Preliminary Report on Patentability mailed Apr. 4, 2017, 7 pages.

International Application No. PCT/EP2015/072606, International Search Report and Written Opinion, mailed Jan. 18, 2016, 14 pages.

International Application No. PCT/US2019/052173, International Preliminary Report on Patentability, mailed Mar. 23, 2021, 12 pages.

International Application No. PCT/US2019/052173, International Search Report and Written Opinion, mailed Jan. 31, 2020, 16 pages.

International Application No. PCT/US2019/052173, Invitation to Pay Additional Fees, mailed Nov. 22, 2019, 2 pages.

James, Stefan K., et al., "Ticagrelor versus clopidogrel in patients with acute coronary syndromes intended for non-invasive management: substudy from prospective randomised PLATelet inhibition and patient Outcomes (PLATO) trial", BMJ (2011); 342: 1-11.

Janeway C.A., et al al., "Immunobiology: the Immune System in Health and Disease", Current Biology, 1997, 14 pages.

Jayasinghe, Rohan, et al., "Dual antiplatelet therapy: Management in general practice", Australian Family Physician (Oct. 2013); 42(10): 702-705.

Jin, Lijun, et al., "The Prognostic Value of ADP-Induced Platelet Aggregation for Bleeding Complications in Low-Intermediate Risk Patients with Acute Coronary Syndrome Taking Clopidogrel After Percutaneous Coronary Intervention", Heart, Lung and Circulation (2017); 26(1): 49-57.

Kanyavuz et al., "Breaking the law: unconventional strategies for antibody diversification," Nat Rev Immunol. (Jun. 2019); 19(6): 355-368.

Ketileborough, C. A., et al., "Isolation of tumor cell-specific single-chain Fv from immunized mice using phage-antibody libraries and the re-construction of whole antibodies from these antibody fragments", European Journal of Immunology (Apr. 1994); 24(4): 952-958.

Kipriyanov S.M., et al., "Generation and Production of Engineered Antibodies," Molecular Biotechnology (2004); 26(1): 39-60.

Koski, Renee, et al., "Comparative Review of Oral P2Y12 Inhibitors", Pharmacy and Therapeutics (Jun. 2018); 43(6): 352-357.

Ladenson, et al., "Isolation and Characterization of a Thermally Stable Recombinant Anti-Caffeine Heavy-Chain Antibody Fragment", Anal. Chem. (2006); 78(13): 4501-4508.

Liu, F. et al., "Synthesis of 5'-functionalized adenosine: suppression of cyclonucleoside formation," Tetrahedr. Lett. (2001); 42(18): 3153-3154.

Lloyd, C., et al., "Modelling the human immune response: performance of a 1011 human antibody repertoire against a broad panel of therapeutically relevant antigens", Protein Engineering, Design and Selection (2009); 22(3): 159-168.

Lu, G., et al., "A specific antidote for reversal of anticoagulation by direct and indirect inhibitors of coagulation factor Xa," Nature Medicine (Apr. 2013); 19(4): 446-451.

Lunn, David J., et al. "Bayesian Analysis of Population PK/PD Models: General Concepts and Software", Journal of Pharmacokinetics and Pharmacodynamics (2002); 29(3): 271-307.

Luo, D., et al., "VI-linker-Vh orientation-dependent expression of single chain Fv-containing an engineered disulfide-stabilized bond in the framework regions", The Journal of Biochemistry (Oct. 1995); 118(4): 825-831.

Mangiacapra, Fabio, et al., "Incremental Value of Platelet Reactivity Over a Risk Score of Clinical and Procedural Variables in Predicting Bleeding After Percutaneous Coronary Intervention via the Femoral Approach Development and Validation of a New Bleeding Risk Score", Circulation: Cardiovascular Interventions (2015); 8(5): 1-8.

Mehta, Shamir R., et al., "Effects of pretreatment with clopidogrel and aspirin followed by long-term therapy in patients undergoing percutaneous coronary intervention: the PCI-CURE study", The Lancet (2001); 358(9281): 527-533.

Meyer, T., et al., "Production of anti-(ADP-ribose) antibodies with the aid of a dinucleotide-pyrophosphatase-resistant hapten and their application for the detection of mono(ADP-ribosyl)ated polypeptides", The FEBS Journal (1986); 155(1): 157-165.

Nylander, S., et al., "Ticagrelor-Induced Bleeding in Mice Can be Reversed by Fviia {Novoseven®} and FII", Journal of the American College of Cardiology (Mar. 12, 2013); 61(10): E212.

Oprea, T. I., et al., "Associating Drugs, Targets and Clinical Outcomes into an Integrated Network Affords a New Platform for Computer-Aided Drug Repurposing", Molecular Informatics (Mar. 14, 2011); 30(2-3): 100-111.

Pehrsson, S., et al., "Hemostatic effects of the ticagrelor antidote MEDI 2452 in pigs treated with ticagrelor on a background of aspirin", Journal of Thrombosis and Haemostasis (2017); 15(6): 1213-1222.

Persic, L., et al., "An integrated vector system for the eukaryotic expression of antibodies or their fragments after selection from phage display libraries", Gene (Mar. 10, 1997); 187(1): 9-18.

Plavix (clopidogrel bisulfate) Tablets: 75 mg, 300 mg (3), Label; Highlights of Prescribing Information, Patient Information approved by the U.S. Food and Drug Administration; Revised: Aug. 2010 (Aug. 2010), Initial U.S. Approval: 1997, Distributed by: Bristol-Myers Squibb/Sanofi Pharmaceuticals Partnership Bridgewater, NJ 08807 USA, 25 pages.

Pruller, F., et al., "Low platelet reactivity is recovered by transfusion of stored platelets: a healthy volunteer in vivo study", Journal of Thrombosis and Haemostasis (Aug. 2011); 9(8): 1670-1673.

Reed, Grant W., et al., "Point-of-Care Platelet Function Testing Predicts Bleeding in Patients Exposed to Clopidogrel Undergoing Coronary Artery Bypass Grafting: Verify Pre-Op TIMI 45—A Pilot Study", Clinical Cardiology (2015); 38(2): 92-98.

Reiter, Y., et al., "Engineering antibody Fv fragments for cancer detection and therapy: Disulfide-stabilized Fv fragments," Nature Biotechnology (Oct. 1996); 14(10): 1239-1245.

Reiter, Y., et al., "Stabilization of the Fv fragments in recombinant immunotoxins by disulfide bonds engineered into conserved framework regions," Biochemistry (1994); 33(18): 5451-5459.

(56) References Cited

OTHER PUBLICATIONS

Roe, Matthew T., et al., "Prasugrel versus Clopidogrel for Acute Coronary Syndromes without Revascularization", New England Journal of Medicine (Oct. 4, 2012); 367(14): 1297-1309.

Rudikoff et al., "Single amino acid substitution altering antigen-binding specificity", PNAS USA, Mar. 1982, 79(6):1979-1983.

Schiele, et al., "A specific antidote for dabigatran: functional and structural characterization", Blood (May 2, 2013); 121(18): 3554-3562.

Sillén, H., et al., "Determination of ticagrelor and two metabolites in plasma samples by liquid chromatography and mass spectrometry," Journal of Chromatography B, Analytical Technologies in the Biomedical and Life Sciences, vol. 878, Issue 25, pp. 2299-2306 {Sep. 1, 2010).

Sillén, H., et al., "Determination of unbound ticagrelor and its active metabolite (AR-C124910XX) in human plasma by equilibrium dialysis and LC-MS/MS," Journal of Chromatography B, Analytical Technologies in the Biomedical and Life Sciences (Aug. 1, 2011); 879(23): 2315-2322.

Springthorpe, B., et al., "From ATP to AZD6140: The discovery of an orally active reversible P2Y12 receptor antagonist for the prevention of thrombosis", Bioorganic & Medicinal Chemistry Letters (Nov. 1, 2007); 17(21): 6013-6018.

Storey, R. F., et al., "Inhibitory effects of ticagrelor compared with clopidogrel on platelet function in patients with acute coronary syndromes: the PLATO {PLATelet inhibition and patient Outcomes) PLATelet substudy," Journal of the American College of Cardiology (Oct. 26, 2010); 56(18): 1456-1462.

Storey, R.F., et al., "Inhibition of platelet aggregation by AZD6140, a reversible oral P2Y12 receptor antagonist, compared with clopidogrel in patients with acute coronary syndromes," Journal of the American College of Cardiology (Nov. 6, 2007); 50(19): 1852-1856.

Åstrand, Magnus, et al., "Pharmacokinetic-pharmacodynamic modelling of platelet response to ticagrelor in stable coronary artery disease and prior myocardial infarction patients", British Journal of Clinical Pharmacology (2019); 85(2): 413-421.

Tantry, Udaya S., et al., "Consensus and Update on the Definition of On-Treatment Platelet Reactivity to Adenosine Diphosphate Associated With Ischemia and Bleeding", Journal of the American College of Cardiology (2013); 62(24): 2261-2273.

Taylor, G., et al., "Is platelet transfusion efficient to restore platelet reactivity in patients who are responders to aspirin and/or clopidogrel before emergency surgery?", The Journal of Trauma and Acute Care Surgery (May 2013); 74(5): 1367-1369.

Teng, R., et al., "Absorption, Distribution, Metabolism, and Excretion of Ticagrelor in Healthy Subjects", Drug Metabolism & Disposition (Sep. 2010); 38(9): 1514-1521.

Teng, R., et al., "Effects of autologous platelet transfusion on platelet inhibition in ticagrelor-treated and clopidogrel-treated subjects", Journal of Thrombosis and Haemostasis (2016); 14(12): 2342-2352.

Teng, R., et al., "Evaluation of the pharmacokinetics and pharmacodynamics of ticagrelor co-administered with aspirin in healthy volunteers", Platelets (Dec. 2013); 24(8): 615-624.

Thiele, T., et al., "Platelet transfusion for reversal of dual antiplatelet therapy in patients requiring urgent surgery: a pilot study", Journal of Thrombosis and Haemostasis (May 2012); 10(5): 968-971.

Thompson, J., et al., "Affinity Maturation of a High-affinity Human Monoclonal Antibody Against the Third Hypervariable Loop of Human Immunodeficiency Virus: Use of Phage Display to Improve Affinity and Broaden Strain Reactivity", Journal of Molecular Biology (Feb. 16, 1996); 256(1): 77-88.

Valgimigli, Marco, et al., "2017 ESC focused update on dual antiplatelet therapy in coronary artery disease developed in collaboration with EACTS: The Task Force for dual antiplatelet therapy in coronary artery disease of the European Society of Cardiology (ESC) and of the European Association for Cardio-Thoracic Surgery (EACTS)", European Heart Journal (2018); 39(3): 213-260.

Von Rhein, C., et al., "Data processing and analysis with the autoPROC toolbox", Acta Crystallographica Section D (Apr. 2011); 67(4): 293-302.

Wallentin, Lars, et al., "Ticagrelor versus Clopidogrel in Patients with Acute Coronary Syndromes", The New England Journal of Medicine (Sep. 10, 2009); 361(11): 1045-1057.

Wiviott, Stephen D., et al., "Prasugrel versus clopidogrel for patients with unstable angina or non-ST-segment elevation myocardial infarction with or without angiography: a secondary, prespecified analysis of the TRILOGY ACS trial", The Lancet (2013); 382(9892): 605-613.

Wiviott, Stephen D., et al., "Prasugrel versus Clopidogrel in Patients with Acute Coronary Syndromes", New England Journal of Medicine (Nov. 15, 2007); 357(20): 2001-2015.

Young, N. M., et al., "Thermal stabilization of a single-chain Fv antibody fragment by introduction of a disulphide bond," FEBS Letters (Dec. 18, 1995); 37(2): 135-139.

Yusuf, S. et al., "Effects of Clopidogrel in Addition to Aspirin in Patients with Acute Coronary Syndromes without ST-Segment Elevation", N Engl J Med. (Aug. 16, 2001); 345(7): 494-502; "Corrections", N Engl J Med. (Dec. 6, 2001); 345(23): 1716.

Zhang, K., et al., "Structure of the human P2Y12 receptor in complex with an antithrombotic drug", Nature (May 1, 2014); 509(7498): 115-118.

Zhu, Z., et al., "Remodeling domain interfaces to enhance heterodimer formation", Protein Science (Apr. 1997); 6(4): 781-788.

Better, Marc, et al., "*Escherichia coli* secretion of an active chimeric antibody fragment", Science (1988); 240(4855): 1041-1043.

Burton, Dennis R., et al. "Human antibodies from combinatorial libraries", Advances in Immunology (1994); 57: 191-280.

International Search Report and Written Opinion for PCT Application No. PCT/US2022/28343, mailed Nov. 1, 2022, 22 pages.

Mullinax, R. L., et al. "Expression of a heterodimeric Fab antibody protein in one cloning step", Biotechniques (1992); 12(6): 864-869.

Sawai, Hideaki, et al., "Direct production of the fab fragment derived from the sperm immobilizing antibody using polymerase chain reaction and cDNA expression vectors", American Journal of Reproductive Immunology (1995); 34(1): 26-34.

Kuznetsov, D.N. et al. (2011). "Clinical Effectiveness of Thrombolytic Therapy With Alteplase and Double Antiplatelet Therapy in Acute Myocardial Infarction," Cardiovascular Therapy and Prevention 10(6):59-63. [English Abstract].

Perepech, N.B. (2016). "Acute Coronary Syndrome: Pathogenesis, Diagnosis, Treatment, Rehabilitation (Lecture 2)," CardioSomatics 7(2):70-81. [English Abstract].

Almquist, J. et al. (Jun. 1, 2016). "Supplemental Information: Dosing MEDI2452 to Ticagrelor Treated Mice Study Desging 1: Mice were Given Tricagrelor as an i.v. Infusion at a Rate of 240 [mu]gxmin -1 xkg —1 for 5 min, Followed by 30 [mu]gxmin -1 xkg -1 for 15 min. Followed by 30 [mu]gxmin -1 xkg —for 15 min. Immediately After Stop of Ticagrelor Infusion, an," located at https://ascpt.onlinelibrary.wiley.com/doi/10.1002/psp4.12089, 3 pages.

Anonymus. (Feb. 14, 2024). "NCT04286438, Version. 62: Bentracimab in Ticagrelor-Treated Patients with Uncontrolled Bleeding or Requiring Urgent Surgery or Invasive Procedure (REVERSE-IT)," Clinical Trials, 57 pages.

Bhatt, D.L. et al. (Apr. 2, 2022). Bentracimab Immediately and Significantly Reverses the Antiplatelet Effects of Ticagrelor in Older People,' Brigham and Women's Hospital, 21 pages.

Bhatt, D.L. et al. (Feb. 22, 2022). "Suppl. Pevidoa2111047_ Protocol for—Bentracimab for Ticagrelor Reversal in patients Undergoing Urgent Surgery," NEJM Evidence 1(3):317, pages.

Bhatt, D.L. et al. (Feb. 22, 2022). Supplemental Appendix for: Bentracimab for Ticagrelor Reversal in Patients Undergoing Urgent Surgery, NEJM Evidence 1(3):19 pages.

Curry, B. et al. (Oct. 3, 2022). "Bentracimab Demonstrated Reversal of Antiplatelet Effects of Ticagrelor: Impact of Hematocrit and Generic Versions of Ticagrelor in Vitro," European Heart Journal 43(Supp. 2):2720.

International Search Report and Written Opinion mailed on Nov. 17, 2025, for PCT Application No. PCT/US2025/037799, filed on Jul. 15, 2025, 23 pages.

(56)     References Cited

OTHER PUBLICATIONS

Kumbhhani, D.J. ((Apr. 2, 2022). "Phase 2B Study to Evaluate the Efficacy of PB2452 in Reversal of Ticagrelor In subjects Aged 50-80—Bentracimab," American College of Cardiology, located at www.acc.org/Latest-in Cardiology/Clinical/Trials/2022/04/01/03/34/ Bentracimab, 2 pages.

Ortega-Paz, L. (2023, e-pub. Apr. 28, 2023). "Clinical and Pre-Clinical Pharmacokinetics and Pharmacodynamics of Bentracimab," Clinical Pharmacokinetics 62(5):637-679.

Sandinge, A-S. et al. (Jul. 26, 2018). "Quantification of Unbound Concentration of Ticagrelor in Plasma as a Proof of Mechanism Biomarker of the Reversal Agent, MEDI2452," Plos One 13(7):e0201202, 14 pages.

* cited by examiner

Figure 1 ticagrelor ticagrelor active metabolite (TAM)    and ticagrelor inactive metabolite (TIM)

- IPA assesses ticagrelor's inhibition of platelet aggregation
  - IPA peaks at 2 - 4 hours after last oral dose at 80 - 90% inhibition (left graph)
  - Complete PB2452 reversal = IPA reduction to <20%
- SAD subjects are pre-dosed with ticagrelor for 48 hours prior to PB2452 IV administration
  - As expected, no reversal observed with 1 g of PB2452

Figure 3

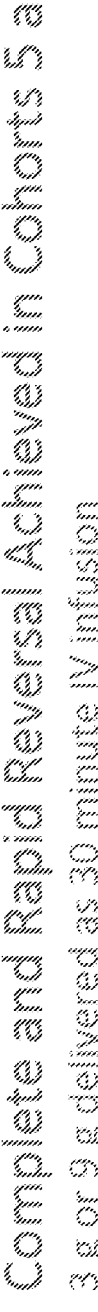
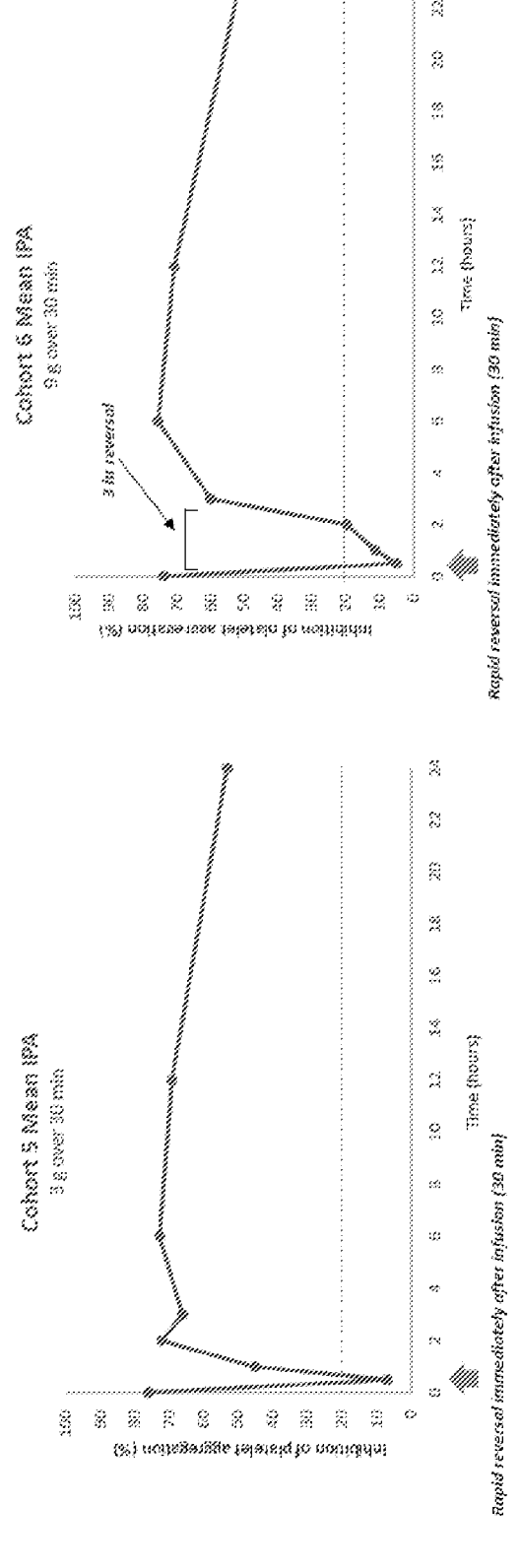

Complete and Rapid Reversal Achieved in Cohorts 5 and 6

3 g or 9 g delivered as 30 minute IV infusion

Cohorts 5 and 6: Rapid, complete reversal with short duration when given as 30 minute IV infusion

- Complete restoration of platelet function at first sampling time point – 30 min, faster than expected
- Speed to reversal critical for patients with active bleeding
- Duration of response was dose-dependent Complete, Sustained Reversal Achieved in Cohort 7

3g 5 min bolus followed by 1.5g 7h 55 min IV infusion

- Clean safety profile: no drug-related AEs
- Reversal in 3 subjects by 5 min
- 16 hr of reversal is clinically important however would like to extend duration of effect
- Verify Now correlates well to IPA Cohorts 8, 9 and 10

Cohorts 8, 9, and 10 achieved study objectives, immediate reversal and sustained duration ● Clean safety profile: no drug-related AEs or SAEs ● Duration of reversal extended to 24 hours, significantly beyond Cohort 7 (16 hours)

Figure 6A

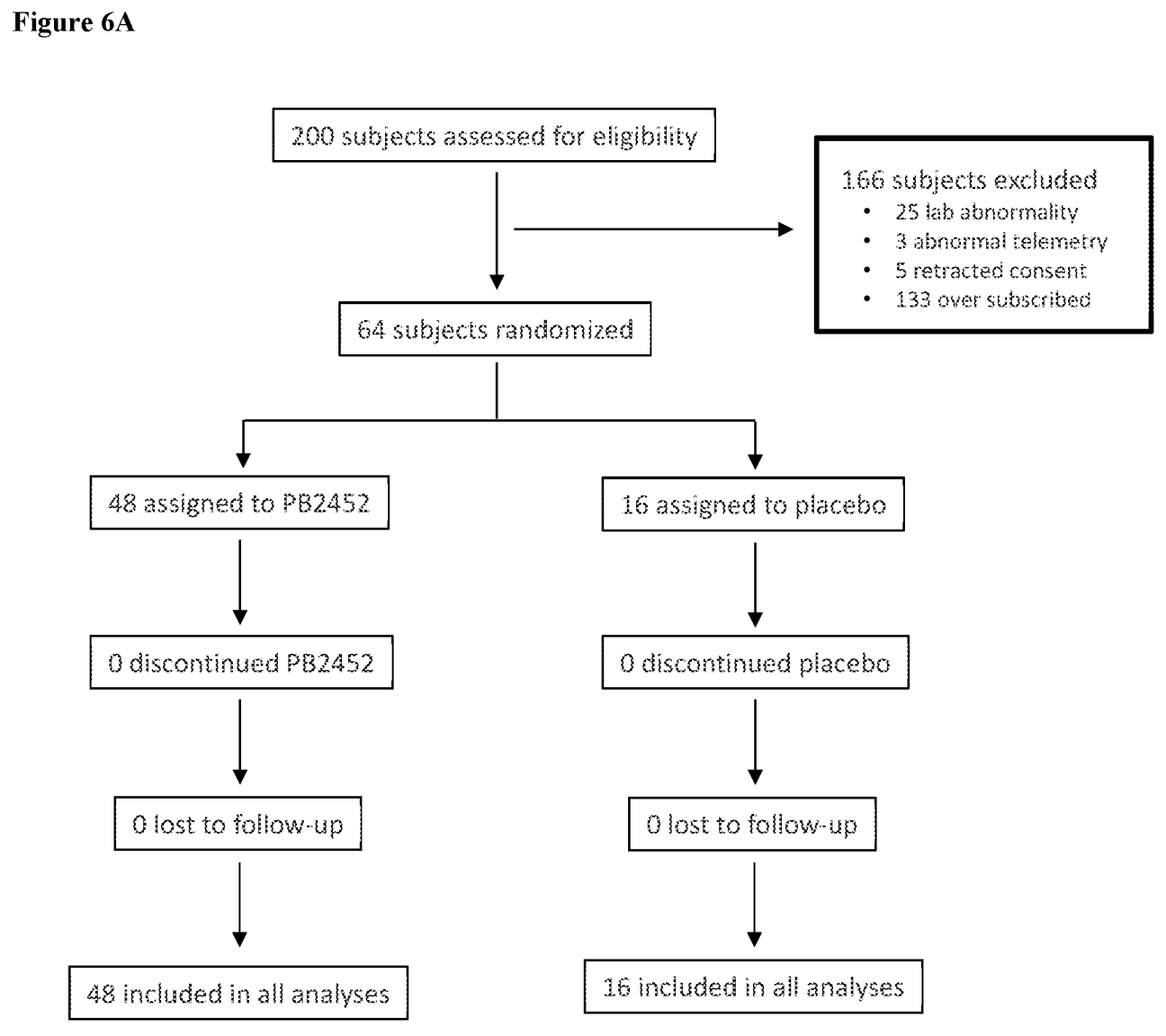

166 subjects excluded
- 25 lab abnormality
- 3 abnormal telemetry
- 5 retracted consent
- 133 over subscribed 200 subjects assessed for eligibility 64 subjects randomized 16 assigned to placebo 0 discontinued placebo 0 lost to follow-up 16 included in all analyses 48 assigned to PB2452

0 discontinued PB2452

0 lost to follow-up 48 included in all analyses

| Cohort | 0.5 hr | 1 hr | 2 hr | 3 hr | 6 hr | 12 hr | 24 hr | 48 hr |
|---|---|---|---|---|---|---|---|---|
| 4 | 1 | 1 | 1 | | 1 | 1 | 1 | 1 |
| 5 | 0.0216 | 0.0433 | 1 | 0.1515 | 1 | 1 | 1 | 1 |
| 6 | 0.0216 | 1 | 0.0433 | 0.0866 | 1 | 1 | 0.5844 | 1 |

P values by timepoint for each cohort

P values by timepoint for each cohort

| Cohort | 5min | 0.25hr | 0.5hr | 1hr | 2hr | 3hr | 6hr | 8hr | 10hr | 12hr | 16hr | 20hr |
|--------|------|--------|-------|-----|-----|-----|-----|-----|------|------|------|------|
| 7 | 0.040 | 0.040 | 0.131 | 0.037 | 0.040 | 0.019 | 0.019 | 0.019 | 0.152 | 0.019 | 0.019 | 0.224 |
| 8 | 0.019 | 0.019 | 0.019 | 0.019 | 0.019 | 0.019 | 0.019 | 0.019 | 0.152 | 0.019 | 0.019 | 0.019 |
| 10 | 0.043 | 0.020 | 0.020 | 0.020 | 0.020 | 0.020 | 0.020 | 0.020 | | 0.020 | 0.020 | 0.020 |

Due to the small sample size for cohort 9 (n=3), statistical testing was not performed.

METHODS OF REVERSING TICAGRELOR ACTIVITY

CROSS-REFERENCE TO RELATED APPLICATIONS

This application is a U.S. National Phase of International Application No.: PCT/US2019/052173, filed Sep. 20, 2019, which claims benefit of Provisional U.S. Application No. 62/733,892, filed Sep. 20, 2018, Provisional U.S. Application No. 62/806,225, filed Feb. 15, 2019, and Provisional U.S. Application No. 62/836,373, filed Apr. 19, 2019, the contents of each of which are incorporated by reference in their entireties for all purposes.

DESCRIPTION OF THE TEXT FILE SUBMITTED ELECTRONICALLY

The contents of the text file submitted electronically herewith are incorporated herein by reference in their entirety: a computer readable format copy of the sequence listing (filename: PHAS-037_04US SeqList_ST25.txt, date recorded: Mar. 19, 2021, file size 44 kilobytes).

BACKGROUND

Acute Coronary Syndrome (ACS) describes a range of conditions associated with sudden reduced blood flow to the heart, including unstable angina and myocardial infarction, or heart attack. ACS is caused by the inappropriate formation of clots in the coronary arteries. These blood clots are made up primarily of platelets, small lens-shaped cells found in the blood that normally aggregate at sites of injury to help stop bleeding. According to the Centers for Disease Control and Prevention, approximately 790,000 Americans have a heart attack every year, and heart attacks are a leading cause of death in the developed world.

The primary treatment for ACS is the use of antiplatelet drugs to prevent the worsening of existing clots or to reduce the formation of additional clots. These clots can occur in the heart or in stents that are placed in the blocked coronary artery to keep the blood vessel open or elsewhere in the body. Without antiplatelet drugs, patients are at a significantly increased risk of recurrent heart attacks, stroke and death. The standard of care for ACS patients is dual anti-platelet therapy, or DAPT, which is a combination of aspirin and an inhibitor of a specific receptor found on platelets known as the $P2Y_{12}$ receptor. This combination, started after a patient experiences a heart attack or other manifestation of ACS, has been shown to significantly reduce platelet aggregation and clot formation and reduce the frequency of recurrent heart attacks, stroke and death.

While the antiplatelet drugs used in DAPT therapy have proven effective at improving overall outcomes in ACS patients, their suppression of blood clotting increases patients' risk of major bleeding. Bleeding events in patients on antiplatelet therapy, which can occur spontaneously or as a result of injury or surgery, are classified as minor or major. In the 18,000-patient clinical trial, Platelet Inhibition and Patient Outcomes, or PLATO, conducted by AstraZeneca, ticagrelor was shown to be superior to the antiplatelet drug clopidogrel, marketed under the brand name Plavix, in reducing recurrent heart attack, stroke and death in patients with ACS (Wallentin et al. 2009). However, in both treatment groups, 11% to 12% of patients in the trial suffered major bleeding events, and in 5.8% of patients, these major bleeding events were fatal or life-threatening. The causes of bleeding varied in the trial population. In approximately 3% of the patients on ticagrelor, major bleeding events were spontaneous and not related to any medical procedure, whereas approximately 9% of patients on ticagrelor developed major bleeding that was related to procedures like coronary artery bypass surgery, or CABG (Wallentin et al. 2009). Although the trial protocol recommended that patients who needed CABG stop taking ticagrelor for one to three days prior to surgery, nearly half of all ticagrelor patients needed surgery urgently and could not wait the up to three days for ticagrelor's effect to dissipate so normal blood clotting could be restored. Overall, up to 80% of CABG patients in the trial suffered a major or life-threatening bleeding event related to the surgery, and for those who needed urgent surgery and could not wait three days for ticagrelor to wash out, approximately 50% experienced a fatal or life-threatening bleeding event (Held et al., 2011). While some of this risk was likely associated with patients' underlying conditions, the overall bleeding risk is significantly increased by antiplatelet drugs, and the current US prescribing information for ticagrelor suggests suspension of ticagrelor treatment for five days prior to surgery.

Despite the increased bleeding risk, antiplatelet drugs, along with anticoagulant drugs which are used to prevent clots in veins, represent some of the most widely prescribed drugs in the United States due to their lifesaving effects. While both of these classes of drugs increase the risk of bleeding, reversal agents have been developed for anticoagulant drugs, but to date, no reversal agents exist for antiplatelet drugs. In the absence of a reversal agent, physicians have limited treatment options, and sometimes administer platelet transfusions, which are unproven in this setting. The ability to quickly reverse the antiplatelet activity of ticagrelor and restore normal clotting would increase its safety, both in instances of major bleeding as well as in situations where surgical or other medical interventions associated with bleeding are urgently needed.

The three oral antiplatelet $P2Y_{12}$ receptor antagonist drugs prescribed in DAPT therapy are clopidogrel, marketed under the brand name Plavix, prasugrel, marketed under the brand name Effient, and ticagrelor, marketed under the brand names Brilinta and Brilique. Unlike clopidogrel and prasugrel that permanently bind to and inhibit the target receptors on platelets, ticagrelor binds to the $P2Y_{12}$ receptor in a transient manner, quickly cycling on and off the receptor. This transient binding of ticagrelor presents a unique opportunity to develop a specific reversal agent for ticagrelor, whereas the permanent binding of the other drugs to the receptor precludes a reversal agent from being developed.

Ticagrelor is considered the best-in-class $P2Y_{12}$ antiplatelet agent because it has demonstrated superior efficacy compared to clopidogrel. Yet, the side-effects of ticagrelor treatment can cause spontaneous bleeding. Further, due to its anti-platelet activity, ticagrelor treatment can be dangerous in patients requiring emergency surgery, and lead to increased blood loss.

Ticagrelor may also be used in patients with unstable angina, in patients with stable ischemic heart disease, in patients with sickle cell disease, including pediatric patients, patients with atrial fibrillation, patients with coronary arterial disease, patients with peripheral arterial disease, patients with ischemic stroke, patients with one or more coronary stents, patients with carotid artery stents, patients with stents following an intracranial aneurysm, patients with arterio-venous fistulae created for hemodialysis. Ticagrelor may also be used in patients with type 2 diabetes mellitus.

SUMMARY OF THE INVENTION

The present disclosure provides methods of reversing the activity of ticagrelor using a human Fab fragment that binds to ticagrelor with high affinity and specificity to reverse ticagrelor's antiplatelet activity.

In some aspects, the present disclosure provides a method of reversing ticagrelor-associated bleeding, or the risk of said bleeding, in a patient in need thereof comprising administering to said patient a composition comprising an effective amount of a pharmaceutical composition comprising an antibody or fragment thereof that binds to ticagrelor ((1S,2S,3R,5S)-3-[7-{[(1R,2S)-2-(3,4-difluorophenyl)cyclopropyl]amino}-5-(propylthio)-3H-[1,2,3]triazolo[4,5-d]pyrimidin-3-yl]-5-(2-hydroxyethoxy)cyclopentane-1,2-diol) or a metabolite or derivative thereof.

In some embodiments, the antibody or a fragment thereof comprises complementarity-determining region (CDR) combinations selected from the group consisting of:

a) SEQ ID NO:53 (VH CDR1), SEQ ID NO:54 (VH CDR2), SEQ ID NO:55 (VH CDR3), SEQ ID NO:58 (VL CDR1), SEQ ID NO:59 (VL CDR2), and SEQ ID NO:60 (VL CDR3);

b) SEQ ID NO:63 (VH CDR1), SEQ ID NO:64 (VH CDR2), SEQ ID NO:65 (VH CDR3), SEQ ID NO:68 (VL CDR1), SEQ ID NO:69 (VL CDR2), and SEQ ID NO:70 (VL CDR3); and c) SEQ ID NO:73 (VH CDR1), SEQ ID NO:74 (VH CDR2), SEQ ID NO:75 (VH CDR3), SEQ ID NO:78 (VL CDR1), SEQ ID NO:79 (VL CDR2), and SEQ ID NO:80 (VL CDR3).

In some embodiments, the antibody or a fragment thereof comprises a combination of heavy chain variable region (VH) and light chain variable region (VL) sequences selected from the group consisting of SEQ ID NO:52 and SEQ ID NO:57; SEQ ID NO:62 and SEQ ID NO:67; and SEQ ID NO:72 and SEQ ID NO: 77.

In some embodiments, the patient has been administered ticagrelor before administration of the anti-ticagrelor antibody or fragment thereof.

In some embodiments, the antibody or fragment thereof is a Fab and the patient is administered a dose between about 1 g and about 48 g. In some embodiments, the dose is between about 9 g to about 18 g of the Fab. In some embodiments, the patient is administered a dose of about 1 g, about 3 g, about 9 g, about 18 g, about 24 g, about 30 g, about 36 g or about 48 g of the Fab.

In some embodiments, the pharmaceutical composition is administered to the patient intravenously. In some embodiments, pharmaceutical composition is administered intravenously over about 15 minutes to about 36 hours.

In some embodiments, the pharmaceutical composition is administered in two or more segments. In some embodiments, the first segment is a bolus. In some embodiments, the administration rates for each of the segments differ. In some embodiments, the administration rates for each of the segments differ for successive segments of the infusion. In some embodiments, the pharmaceutical composition is administered in three or more segments, wherein the administration rates for each of the segments differ for successive segments of the infusion. In some embodiments, the pharmaceutical composition is administered in the following schedule: 12 g infused over 10 minutes, followed by 12 g over 6 hours, followed by 12 g over 18 hours.

In some embodiments, the pharmaceutical composition comprises about 50 mg/mL to about 200 mg/mL of the anti-ticagrelor antibody or fragment thereof, about 5 mM to about 50 mM histidine/histidine hydrochloride buffer, about 100 mM to about 300 mM sucrose, and about 0.01% (w/v) to about 1.0% (w/v) polysorbate 80, pH 5.5 to 6.5. In some embodiments, the pharmaceutical formulation comprises 100 mg/mL of the anti-ticagrelor antibody or fragment thereof, 25 mM histidine/histidine hydrochloride buffer, 290 mM sucrose, and 0.05% (w/v) polysorbate 80, pH 6.0. In some embodiments, the pharmaceutical formulation is diluted in isotonic saline for administration.

In some embodiments, the ticagrelor-associated bleeding is major bleeding. In some embodiments, the major bleeding is characterized by being life-threatening, potentially leading to clinically significant disability, requiring surgery to control the bleeding, requiring treatment with blood products, or is acute bleeding associated with a clinically important drop in hemoglobin. In some embodiments, the patient requires surgery or intervention. In some embodiments, the patient requires urgent surgery or intervention. In some embodiments, the urgent surgery or intervention is known to be associated with a significant risk of bleeding, such as coronary artery bypass surgery, has an adverse surgical outcome if bleeding is not carefully controlled, neurological, ophthalmologic, or joint replacement surgery, associated with risk of experiencing perioperative events; or in a patient at high risk of thrombosis if dual antiplatelet therapy is withheld preoperatively. In some embodiments, the patient requires elective surgery or intervention which is known to be associated with a significant risk of bleeding. In some embodiments, the patient is at risk of developing, or has been diagnosed with Acute Coronary Syndrome (ACS). In some embodiments, the patient is at risk of developing, or has been diagnosed with a disease selected from the group consisting of myocardial infarction (MI), unstable angina, stable ischemic heart disease, in sickle cell disease, including pediatric patients, atrial fibrillation, coronary arterial disease, peripheral arterial disease, ischemic stroke, one or more coronary stents, carotid artery stents, stents following an intracranial aneurysm, and arterio-venous fistulae created for hemodialysis.

In some embodiments, the patient is a pediatric patient. In some embodiments, the pediatric patient is younger than 18 years old. In some embodiments, the pediatric patient is younger than 2 years old.

In some embodiments, the patient is an adult patient. In some embodiments, the adult patient is between 18 and 64 years old inclusive. In some embodiments, the patient is over 64 years old. In some embodiments, the patient is between 65 and 80 years old inclusive.

In some embodiments, the patient has been administered aspirin (acetylsalicylic acid).

In some embodiments, administration of the antibody or fragment thereof reverses ticagrelor activity. In some embodiments, administration of the antibody or fragment thereof restores platelet function. In some embodiments, administration of the antibody or fragment thereof restores platelet aggregation. In some embodiments, administration of the antibody or fragment thereof restores platelet aggregation to at least 80% of baseline. In some embodiments, administration of the antibody or fragment thereof restores platelet aggregation within 1 minute to 60 minutes of administration. In some embodiments, administration of the antibody or fragment thereof restores platelet aggregation within 5 minutes of administration. In some embodiments, administration of the antibody or fragment thereof provides a sustained restoration of platelet aggregation. In some embodiments, the restoration of platelet aggregation is sustained for at least 12 hours after administration. In some embodiments, the restoration of platelet aggregation is sustained for at least 16 hours after administration. In some embodiments, the restoration of platelet aggregation is sustained for at least 24 hours after administration.

In some embodiments, the patient has been administered ticagrelor and one or more additional drugs that impact ticagrelor exposure in the patient. In some embodiments the patient has been administered ticagrelor and one or more additional drugs that inhibit the activity of cytochrome P450 isoform 3A (CYP3A), leading to increased exposure to ticagrelor. In some embodiments the patient has been administered ticagrelor and one or more additional drugs that induce the activity of CYP3A, leading to reduced exposure to ticagrelor.

In some embodiments the patient has taken an overdose of ticagrelor.

BRIEF DESCRIPTION OF THE FIGURES

FIG. 1 shows the structure of Ticagrelor and metabolites of ticagrelor.

FIG. 3 shows mean inhibition of platelet aggregation (IPA) in Cohorts 4 and 6. Intravenous administration of 3 g or 9 g PB2452 over 30 minutes causes complete restoration of platelet function by 30 minutes.

FIGS. 6A-B show an exemplary enrollment and study flowchart. Healthy subjects were screened and randomized according the flow diagram shown. To ensure that full cohorts were randomized for each dose cohort, an excess of subjects were screened prior to each cohort enrollment (A). Subject check-in, randomization, and discharge schedule is shown (B).

6 fyNow PRU in (A), between LTA measured aggregation and VASP ELISA PRI (B), and between VerifyNow PRU and VASP ELISA PRI (C). All timepoints were included. r values represent correlation coefficients. $P<0.0001$ for all analyses.

Figures 10A, 10B:
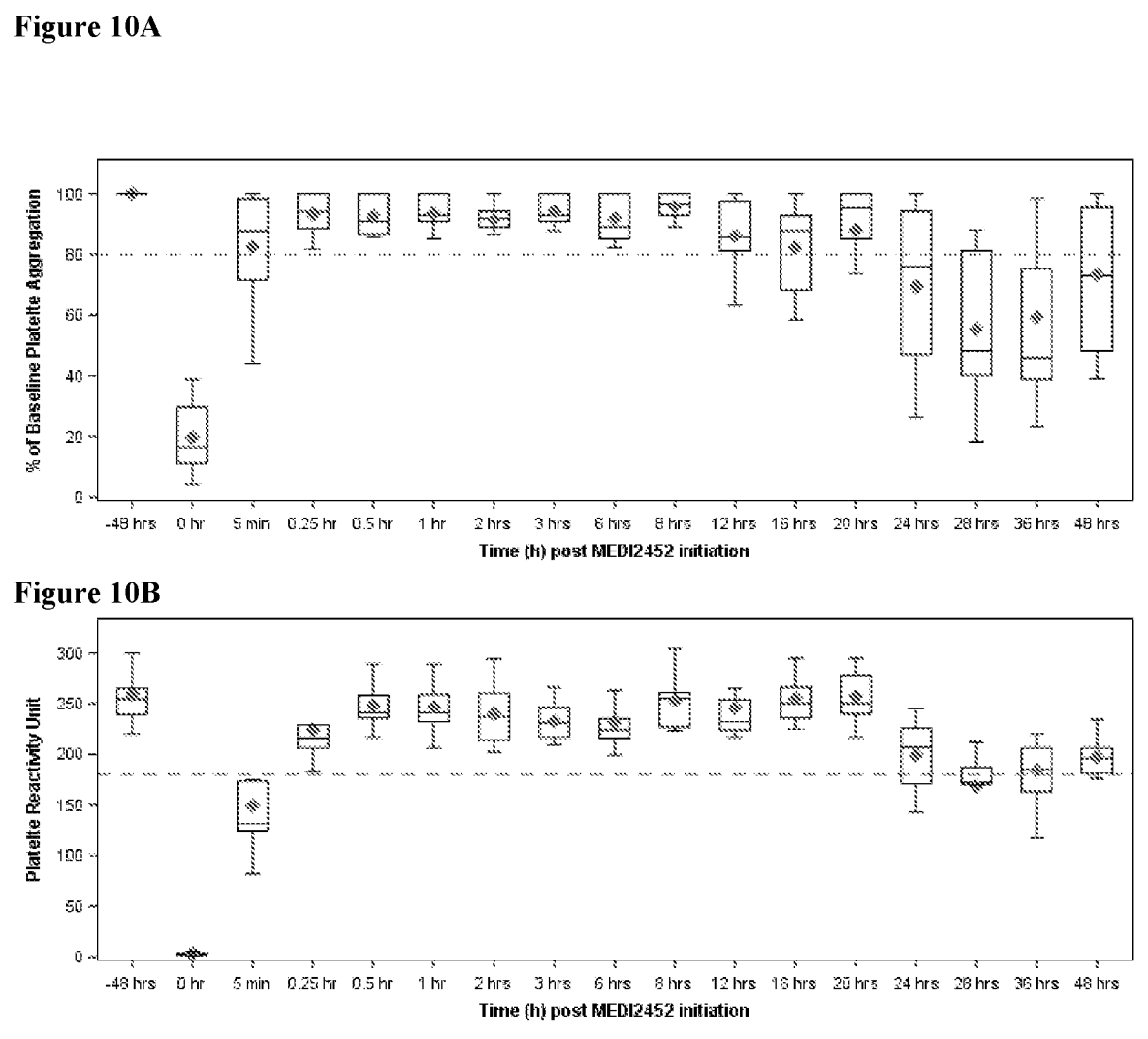
Figure 10C:
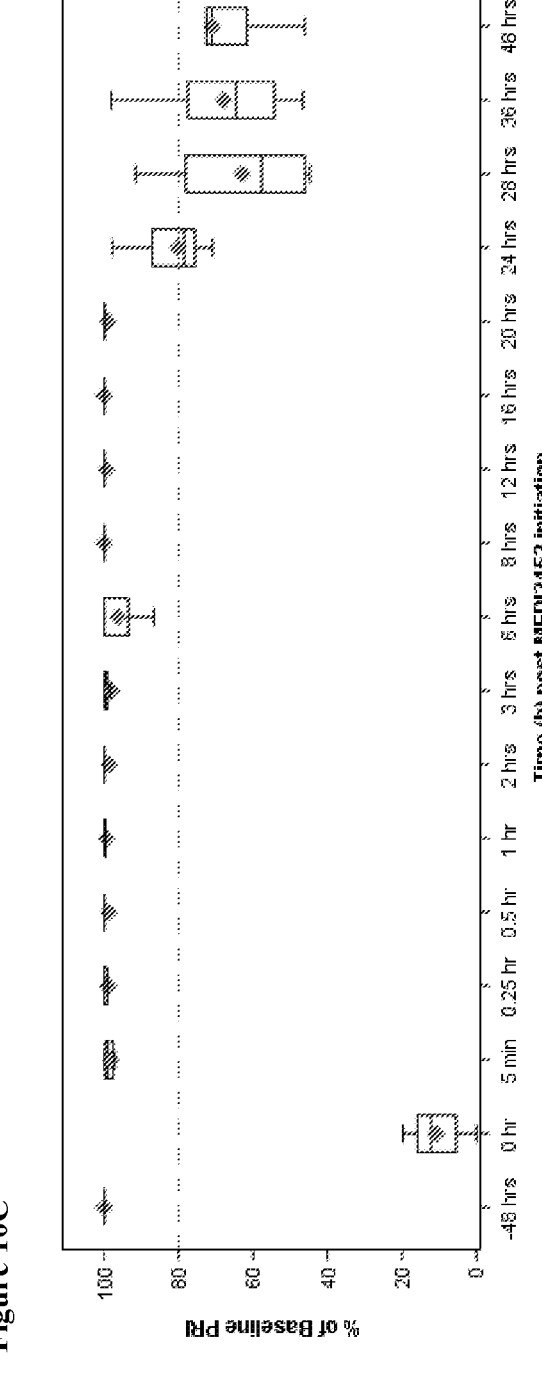

FIGS. 10A-C show the normalization of normal platelet function post-administration of PB2452. The degree of reversal delivered by PB2452 was assessed by comparing platelet function at multiple timepoints post-PB2452, with baseline platelet function assessed in all subjects prior to ticagrelor pretreatment (−48 hr). For platelet aggregation assessed by LTA, normal platelet function post-reversal was considered to be ≥80% of baseline platelet aggregation as shown by the dotted line (A). For VerifyNow platelet reactivity units (PRU), normal platelet function post-reversal was considered to be ≥180 PRU as shown by the dotted line (B). For P2Y12 receptor signaling measured by the VASP platelet reactivity index (PRI), normal platelet function post-reversal was considered to be ≥80% of baseline PRI as shown by the dotted line (C).

FIGS. 11A-D show the pharmacokinetics of PB2452 and ticagrelor. Shown are the circulating drug concentrations of ascending doses of PB2452 over time in Cohorts 4, 5, and 6 (A), the circulating drug concentrations of total ticagrelor over time in Cohorts 4, 5, and 6 (B), the circulating drug concentrations over time of fixed 18 g doses of PB2452 with extended infusion times in Cohorts 7-10 (C), and the circulating drug concentrations of total ticagrelor over time in Cohorts 7-10 (D).

Figure 12A:
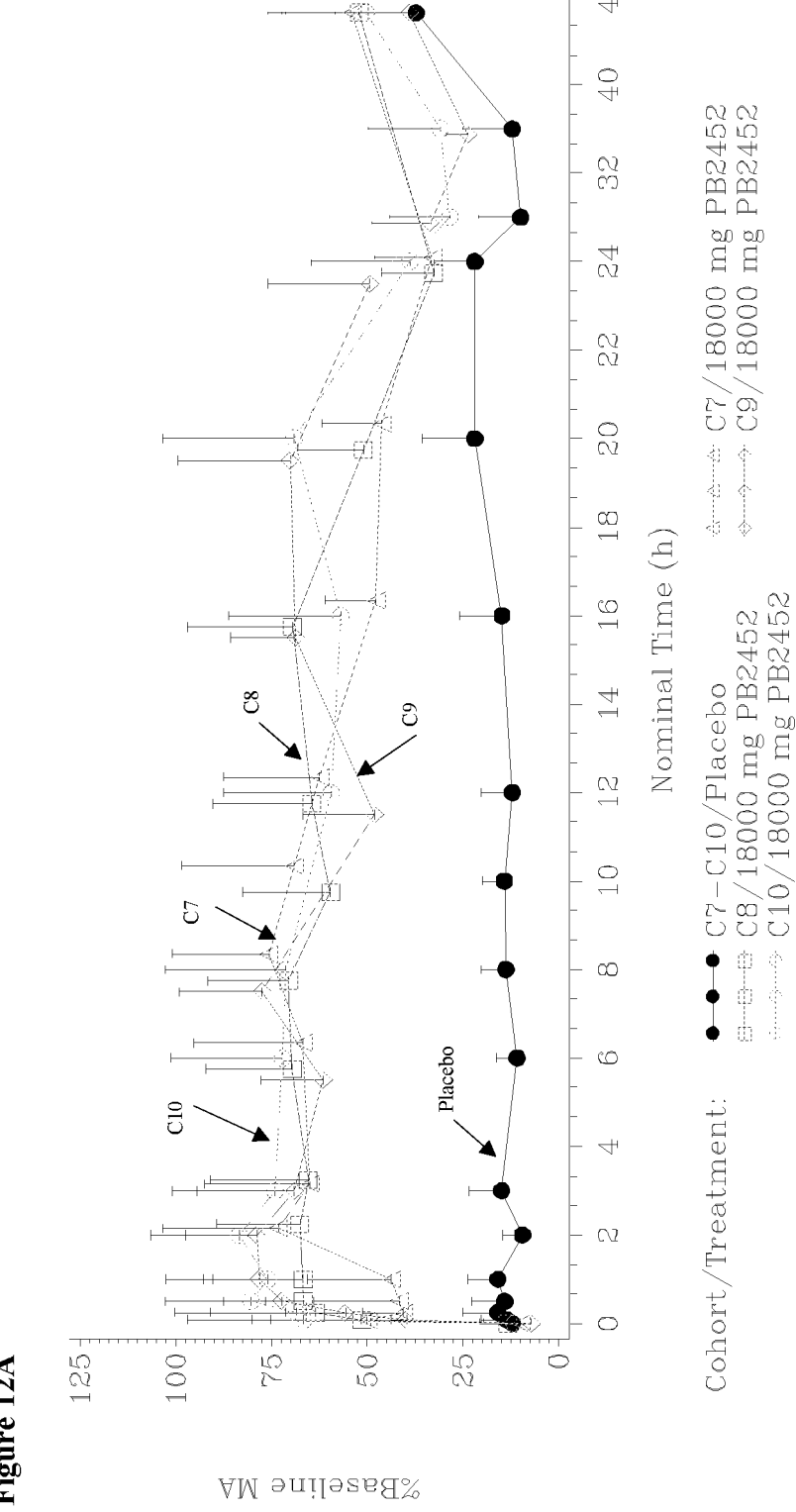
Figure 12B:
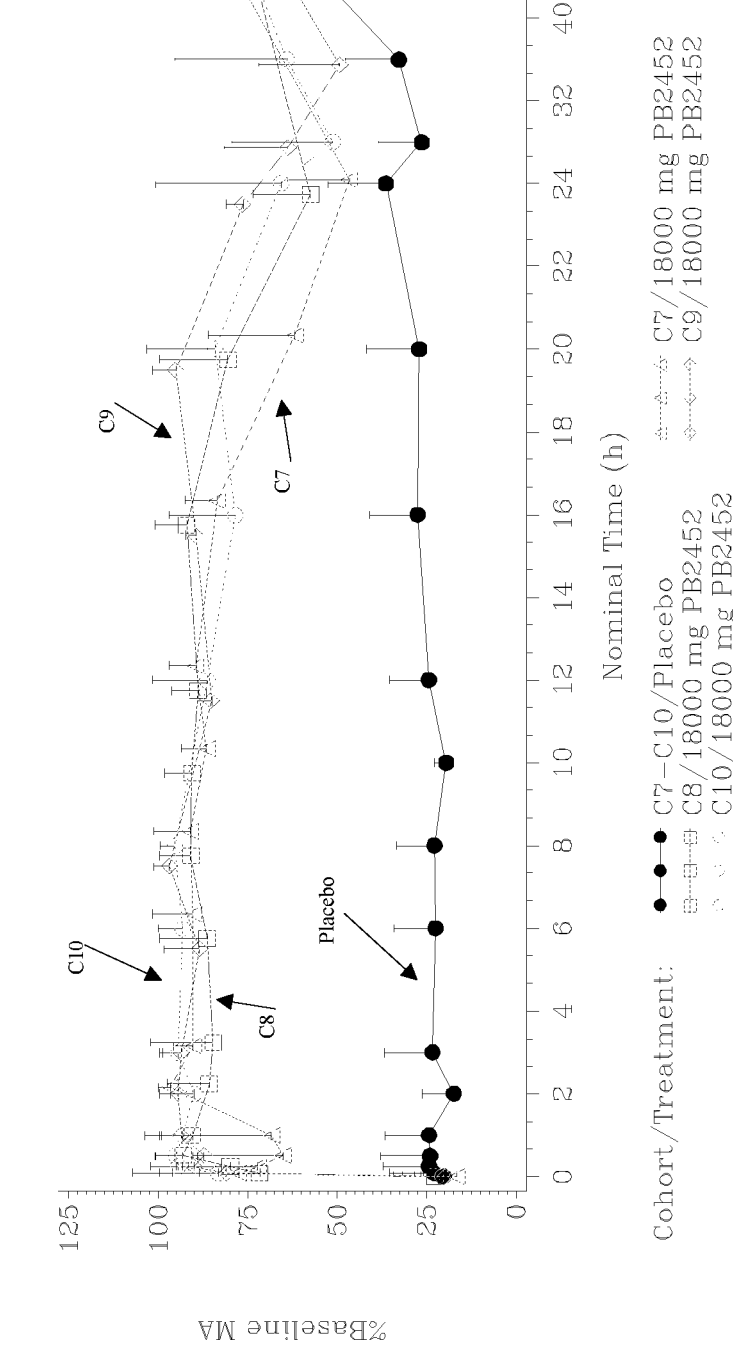

FIGS. 12A-B show platelet aggregation with low-dose ADP. Shown are Cohorts 7-10 mean platelet aggregation data measured by LTA using 5 μM ADP as the $P2Y_{12}$ agonist (A), and Cohorts 7-10 mean platelet aggregation data using 20 μM ADP as the $P2Y_{12}$ agonist (B).

DETAILED DESCRIPTION

Ticagrelor works by binding to the $P2Y_{12}$ receptor on platelets, thereby preventing adenosine diphosphate, or ADP, from causing platelet aggregation. Ticagrelor binds transiently to the $P2Y_{12}$ receptor, cycling on and off, allowing anti-ticagrelor agents, such as PB2452, a human Fab fragment that binds to ticagrelor, to bind to free ticagrelor, thereby preventing ticagrelor's activation of the receptor and removing ticagrelor from circulation. With ticagrelor bound to PB2452 or removed, ADP can once again bind the $P2Y_{12}$ receptor and induce platelet aggregation.

Anti-Ticagrelor Agents

In some aspects, the present disclosure provides agents that bind to ticagrelor ((1S,2S,3R,5S)-3-[7-{[(1R,2S)-2-(3, 4-difluorophenyl)cyclopropyl]amino}-5-(propylthio)-3H-[1,2,3]-triazolo[4,5-d]pyrimidin-3-yl]-5-(2-hydroxyethoxy) cyclopentane-1,2-diol) or a metabolite or derivative thereof.

Figure 1:
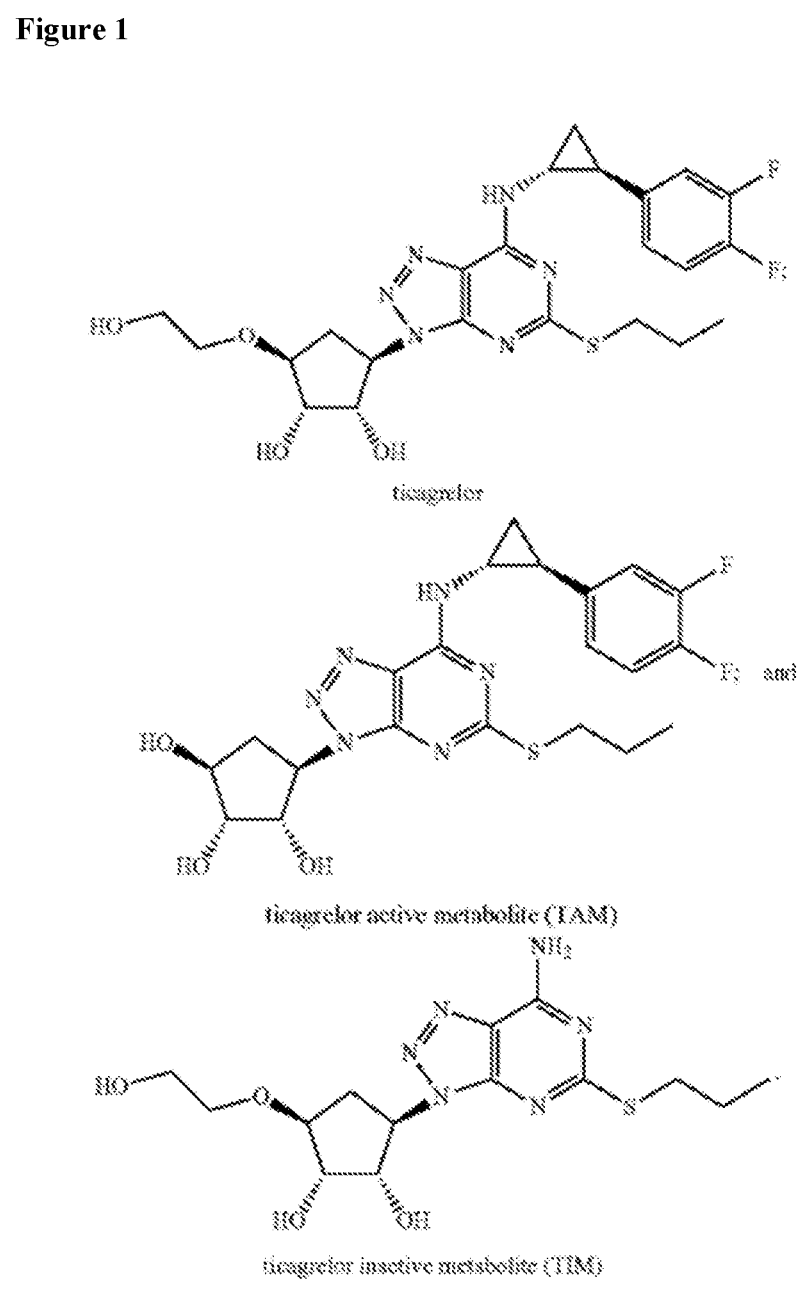

In some embodiments, the ticagrelor and/or metabolite thereof is depicted in FIG. 1. In some embodiments, the ticagrelor metabolite is an active metabolite.

In some aspects, the agent that binds to ticagrelor and/or a metabolite thereof is an antibody or a fragment thereof. In some embodiments, the antibody or fragment thereof is selected from, but is not limited to, a polyclonal antibody, a monoclonal antibody, a humanized antibody, a human antibody, a single chain Fv (scFv), a single domain antibody, a Fab, a F(ab')2, a single chain diabody, an antibody mimetic, an antibody variable domain, a camelid antibody (also known as $V_{HH}$ or nanobody). In some embodiments, the antibody comprises a scFv. In some embodiments, the antibody or a fragment thereof comprises a Fab. In some embodiments the antibody mimetic is an adnectin molecule, an affibody molecule, an affilin molecule, an affimer molecule, an affitin molecule, an alphabody molecule, an anticalin molecule, an aptamer molecule, an armadillo repeat protein molecule, an atrimer molecule, an avimer molecule, a designed ankyrin repeat protein molecule (DARPin) molecule, a fynomer molecule, a knottin molecule, a knottin molecule, a Kunitz domain inhibitor molecule, a monobody, a nanoCLAMP molecule, or a nanofin molecule.

In further embodiments of the above aspects and embodiments, the antibody or a fragment thereof comprises a heavy chain variable region (VH) sequence selected from the group consisting of SEQ ID NO:2, SEQ ID NO:12, SEQ ID NO:22, SEQ ID NO:32, SEQ ID NO:42, SEQ ID NO:52, SEQ ID NO:62, and SEQ ID NO:72; and a light chain variable region (VL) sequence selected from the group consisting of SEQ ID NO:7, SEQ ID NO:17, SEQ ID NO:27, SEQ ID NO:37, SEQ ID NO:47, SEQ ID NO:57, SEQ ID NO:67, and SEQ ID NO:77. In some embodiments, the antibody comprises a combination of VH and VL sequences selected from the group consisting of SEQ ID NO:2 and SEQ ID NO:7; SEQ ID NO:12 and SEQ ID NO:17; SEQ ID NO:22 and SEQ ID NO:27; SEQ ID NO:32 and SEQ ID NO:37; SEQ ID NO:42 and SEQ ID NO:47; SEQ ID NO:52 and SEQ ID NO:57; SEQ ID NO:62 and SEQ ID NO:67; and SEQ ID NO:72 and SEQ ID NO:77. In further embodiments, the antibody comprises a combination of VH and VL selected from the group consisting of SEQ ID NO:52 and SEQ ID NO:57; SEQ ID NO:62 and SEQ ID NO:67; and SEQ ID NO:72 and SEQ ID NO:77.

In further embodiments of the above aspects and embodiments, the antibody or a fragment thereof comprises framework regions (FR) and complementarity-determining regions (CDRs) 1, 2, and 3 of a heavy chain variable region and a light chain variable region, wherein the CDR1, CDR2, and CDR3 sequences of the heavy chain variable region comprise, SEQ ID NO:3 (CDR1), SEQ ID NO:4 (CDR2), and SEQ ID NO:5 (CDR3); SEQ ID NO:13 (CDR1), SEQ ID NO:14 (CDR2), and SEQ ID NO:15 (CDR3); SEQ ID NO:23 (CDR1), SEQ ID NO:24 (CDR2), and SEQ ID NO:25 (CDR3); SEQ ID NO:33 (CDR1), SEQ ID NO:34 (CDR2), and SEQ ID NO:35 (CDR3); SEQ ID NO:43 (CDR1), SEQ ID NO:44 (CDR2), and SEQ ID NO:45 (CDR3); SEQ ID NO:53 (CDR1), SEQ ID NO:54 (CDR2), and SEQ ID NO:55 (CDR3); SEQ ID NO:63 (CDR1), SEQ ID NO:64 (CDR2), and SEQ ID NO:65 (CDR3); or SEQ ID NO:73 (CDR1), SEQ ID NO:74 (CDR2), and SEQ ID NO:75 (CDR3); and wherein the CDR1, CDR2, and CDR3 sequences of the light chain variable region comprise, SEQ ID NO:8 (CDR1), SEQ ID NO:9 (CDR2), and SEQ ID NO:10 (CDR3); SEQ ID NO:18 (CDR1), SEQ ID NO:19 (CDR2), and SEQ ID NO:20 (CDR3); SEQ ID NO:28 (CDR1), SEQ ID NO:29 (CDR2), and SEQ ID NO:30 (CDR3); SEQ ID NO:38 (CDR1), SEQ ID NO:39 (CDR2), and SEQ ID NO:40 (CDR3); SEQ ID NO:48 (CDR1), SEQ ID NO:49 (CDR2), and SEQ ID NO:50 (CDR3); SEQ ID NO:58 (CDR1), SEQ ID NO:59 (CDR2), and SEQ ID NO:60 (CDR3); SEQ ID NO:68 (CDR1), SEQ ID NO:69 (CDR2), and SEQ ID NO:70 (CDR3); or SEQ ID NO:78 (CDR1), SEQ ID NO:79 (CDR2), and SEQ ID NO:80 (CDR3). In further embodiments, the antibody comprises a combination of CDR regions selected from the group consisting of: SEQ ID NO:53 (VH CDR1), SEQ ID NO:54 (VH CDR2), SEQ ID NO:55 (VH CDR3), SEQ ID NO:58 (VL CDR1), SEQ ID NO:59 (VL CDR2), and SEQ ID NO:60 (VL CDR3); SEQ ID NO:63 (VH CDR1), SEQ ID NO:64 (VH CDR2), SEQ ID NO:65 (VH CDR3), SEQ ID NO:68

(VL CDR1), SEQ ID NO:69 (VL CDR2), and SEQ ID NO:70 (VL CDR3); and SEQ ID NO:73 (VH CDR1), SEQ ID NO:74 (VH CDR2), SEQ ID NO:75 (VH CDR3), SEQ ID NO:78 (VL CDR1), SEQ ID NO:79 (VL CDR2), and SEQ ID NO:80 (VL CDR3).

In some embodiments, the antibody or fragment thereof comprises the amino acid sequences of SEQ ID NO:73 (VH CDR1), SEQ ID NO:74 (VH CDR2), SEQ ID NO:75 (VH CDR3), SEQ ID NO:78 (VL CDR1), SEQ ID NO:79 (VL CDR2), and SEQ ID NO:80 (VL CDR3). In some embodiments, the antibody or fragment thereof comprises the amino acid sequences of SEQ ID NO:72 and SEQ ID NO:77. In some embodiments, the antibody or fragment thereof comprising the amino acid sequences of SEQ ID NO: 72 and SEQ ID NO: 77 is PB2452 (MEDI2452). In some embodiments, the antibody or fragment thereof comprises SEQ ID NO: 81. In some embodiments, the antibody or fragment thereof comprises the amino acid sequences of a VH region and a CH region. In some embodiments, the antibody or fragment thereof comprises the amino acid sequences of a VH region and a CH1 region. In some embodiments, the antibody or fragment thereof comprises the amino acid sequences of SEQ ID NO: 72 and a CH1 region. In some embodiments, the antibody or fragment thereof comprises the amino acid sequence of SEQ ID NO: 83. In some embodiments, the antibody or fragment thereof comprises the amino acid sequence encoded by the nucleic acid sequence of SEQ ID NO: 84. In some embodiments, the antibody or fragment thereof comprises the amino acid sequences of a VL and a CL region. In some embodiments, the antibody or fragment thereof comprises the amino acid sequences of SEQ ID NO: 77 and a CL region. In some embodiments, the antibody or fragment thereof comprises the amino acid sequence of SEQ ID NO: 85. In some embodiments, the antibody or fragment thereof comprises the amino acid sequence encoded by the nucleic acid sequence of SEQ ID NO: 86. In some embodiments, the antibody or fragment thereof comprising the amino acid sequences of SEQ ID NO: 83 and SEQ ID NO: 85 is PB2452 (MEDI2452).

In some embodiments, the antibodies or fragments thereof of the disclosure include one or more amino acid substitutions, deletions or additions, either from natural mutations or human manipulation. As indicated, changes are preferably of a minor nature, such as conservative amino acid substitutions that do not significantly affect the folding or activity of the antibody or fragment thereof.

The present disclosure provides antibodies or fragments thereof that comprise, or alternatively consist of, variants (including derivatives) of the VH domains, VH CDRs, VL domains, and VL CDRs described herein, which antibodies immunospecifically bind to ticagrelor or a derivative or metabolite thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. In specific embodiments, the variants encode substitutions of VHCDR3. In a preferred embodiment, the variants have conservative amino acid substitutions at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind ticagrelor or a derivative or metabolite thereof). Following mutagenesis, the encoded protein may routinely be expressed and the functional and/or biological activity of the encoded protein, (e.g., ability to immunospecifically bind ticagrelor or a derivative or metabolite thereof) can be determined using techniques described herein or by routinely modifying techniques known in the art.

In another embodiment, an antibody or fragment thereof of the disclosure that immunospecifically binds to ticagrelor, a derivative, or a metabolite thereof comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VL domains. In another embodiment, an antibody of the disclosure that immunospecifically binds to ticagrelor, a derivative, or a metabolite thereof comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VL CDRs. In another embodiment, an antibody of the disclosure that immunospecifically binds to ticagrelor, a derivative, or a metabolite thereof comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VL CDR3s. Nucleic acid molecules encoding these antibodies are also encompassed by the disclosure.

In another embodiment, an antibody or fragment thereof of the disclosure that immunospecifically binds to ticagrelor, a derivative, or a metabolite thereof comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VH domains. In another embodiment, an antibody of the disclosure that immunospecifically binds to ticagrelor, a derivative, or a metabolite thereof comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VH CDRs. In another embodiment, an antibody of the disclosure that immunospecifically binds to ticagrelor, a derivative, or a metabolite thereof comprises, or alternatively consists of, a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to any one of the VH CDR3s. Nucleic acid molecules encoding these antibodies are also encompassed by the disclosure.

PB2452 is a recombinant human IgG1λ monoclonal Fab antibody fragment that binds specifically to ticagrelor and TAM. PB2452 was obtained by optimization of a human anti-ticagrelor antibody using phage display, from libraries that were generated by randomizing amino acids in the variable heavy or variable light chain complementarity-determining region 3s followed by affinity selection and screening. See US 2016/0130366 which is incorporated by reference herein in its entirety for all purposes. PB2452 is produced in *E. coli* cells and is purified using a 4-step chromatography process.

In some embodiments, the antibody or fragment thereof binds to ticagrelor and neutralizes the anti-platelet aggregation activity of ticagrelor and TAM, thus restoring ADP-induced platelet aggregation in the presence of ticagrelor and TAM.

In some embodiments, the terminal half-life of the antibody or fragment thereof in a subject is about the same as the terminal half-life of ticagrelor and TAM. In some embodiments the antibody terminal half-life is from about 4-24 hours (e.g., 4, 5, 6, 7, 8, 9, 10, 11, 12, 13, 14, 15, 16, 17, 18, 19, 20, 21, 22, 23, or 24 hours). In some embodiments the terminal half-life is from about 4-12 hours (e.g., 4, 5, 6, 7, 8, 9, 10, 11, or 12 hours). In some embodiments, the terminal half-life in a subject is between about 6-9 hours. In some embodiments, the terminal half-life in a subject is between about 6-7 hours. In some embodiments, the terminal half-life is about 6.9 hours.

In some embodiments, the distribution half-life of the antibody or fragment thereof in a subject is about the same as the distribution half-life of ticagrelor and TAM. In some embodiments the distribution half-life is from about 0.1 to 2 hours (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2 hours). In some embodiments the distribution half-life is from about 0.1 to 1 hour (e.g., 0.1, 0.2, 0.3, 0.4, 0.5, 0.6, 0.7, 0.8, 0.9, or 1.0 hour). In some embodiments, the distribution half-life is about 0.89 hours.

In some embodiments, the antibody or fragment thereof provides for a rapid onset of activity. For example, in embodiments the antibody time to onset or the time to neutralize ticagrelor and TAM mediated platelet inhibition, is from about 5-120 minutes, or from about 5-60 minutes. In some embodiments, the time to onset is less than 60 minutes. In some embodiments, the time to onset is about 30 minutes. In some embodiments, the time to onset is less than about 30 minutes. In some embodiments, the time to onset is less than about 10 minutes. In some embodiments, the time to onset is less than about 5 minutes.

In some embodiments, the antibody or fragment thereof provides for sustained inhibition of ticagrelor and TAM activity. In some embodiments, the inhibition of ticagrelor and TAM activity by the antibody or fragment thereof is sustained for about 2 to about 48 hours (e.g. 2, 3, 4, 5, 6, 7, 8, 9 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours). In some embodiments, the sustained inhibition of ticagrelor and TAM activity is dose dependent. In some embodiments, the sustained inhibition of ticagrelor and TAM activity is dependent on the dose administered in a bolus before IV infusion. In some embodiments, the sustained inhibition of ticagrelor and TAM activity is dependent on the dose administered via IV infusion.

In some embodiments, the antibody or fragment thereof of the present disclosure exhibits both rapid (e.g. within 5 minutes of administration) and sustained (e.g. up to 24 or 48 hours) inhibition of ticagrelor and TAM activity.

In some embodiments, the antibody or fragment thereof is administered to the subject in need thereof immediately after the last ticagrelor administration. In some embodiments, the antibody or fragment thereof is administered to the subject in need thereof within about 1 hour to 120 hours after the last ticagrelor administration. In some embodiments, the antibody or fragment thereof is administered to a subject in need thereof within about 1 hour to 72 hours after the last ticagrelor administration. In some embodiments, the antibody or fragment thereof is administered to the subject in need thereof within about 1 hour to 24 hours (e.g. about 1, 2, 3, 4, 5, 6, 7, 8, 9, 10, 11, 12, 13, 14, 15, 16, 17, 18, 19, 20, 21, 22, 23, or 24 hours).

In some embodiments the antibody or fragment thereof has a PK/PD profile that provides for a rapid offset of activity, such that, for example, a subject who has been administered the antibody may recommence with the pre-scribed ticagrelor therapy. In some embodiments, a subject who has received an antibody disclosed herein (e.g., by i.v. infusion) may receive or restart ticagrelor therapy within six hours following the administration of the antibody. In some embodiments, a subject who has received an antibody or fragment thereof disclosed herein (e.g., by i.v. infusion) may receive or restart ticagrelor therapy within twelve hours following the administration of the antibody. In some embodiments, a subject who has received an antibody disclosed herein (e.g., by i.v. infusion) may receive or restart ticagrelor therapy within twenty-four hours following the administration of the antibody.

PB2452 Activity

Without being bound by theory, PB2452 binds to ticagrelor with an affinity that is 100 times stronger than ticagrelor's affinity for the $P2Y_{12}$ receptor. This high affinity enables PB2452 to bind to free ticagrelor, resulting in a rapid reversal of ticagrelor's effect and restoration of platelet activity.

The chemical starting point for the development of ticagrelor was adenosine triphosphate (ATP), and ticagrelor retains an adenosine-like core. To confirm the specificity of PB2452 for ticagrelor and ticagrelor active metabolite (TAM), its binding to ATP, ADP, and adenosine was evaluated. To further confirm PB2452 specificity, a structural database for marketed drugs was interrogated for molecules that have any structural similarity to ticagrelor. From this in silico analysis, a panel of 12 compounds was selected (fenofibrate, nilvadipine, cilostazol, bucladesine, regadenoson, cyclothiazide, cyfluthrin, lovastatin, linezolid, simvastatin, cangrelor, and pantoprazole). The selectivity of PB2452 was determined by competition binding with PB2452 to biotinylated ticagrelor. No inhibition of PB2452 binding to biotinylated ticagrelor was found for ATP, ADP, adenosine, or the 12 structurally related compounds. Thus, PB2452 binds with high affinity and selectivity to ticagrelor and TAM.

In some embodiments, the anti-ticagrelor antibody or fragment thereof reverses, prevents, inhibits, or reduces ticagrelor or TAM activity. In some embodiments, this ticagrelor or TAM activity is selected from, but not limited to, decreasing ADP-induced platelet aggregation and/or binding to the $P2Y_{12}$ receptor. In some embodiments, administration of the anti-ticagrelor antibody or fragment thereof restores ADP-induced platelet aggregation and/or binding to the $P2Y_{12}$ receptor. In some embodiments, the anti-ticagrelor antibody that restores ADP-induced platelet aggregation and/or binding to the $P2Y_{12}$ receptor is PB2452. See US 2016/0130366 which is incorporated by reference herein in its entirety for all purposes.

Methods of Treatment

In some aspects, the present disclosure provides a method of reversing, inhibiting, decreasing, or preventing ticagrelor or TAM activity comprising administering pharmaceutical compositions comprising an anti-ticagrelor antibody or fragment thereof to a subject in need. The reversal, inhibition, decrease, or prevention of ticagrelor or TAM activity may be measured by any means known in the art, including, for example by measuring free or total ticagrelor in blood samples In some embodiments, administration of the pharmaceutical compositions comprising an anti-ticagrelor antibody or fragment thereof restores platelet aggregation. In some embodiments, administration of the pharmaceutical compositions comprising an anti-ticagrelor antibody or fragment thereof inhibits the binding of ticagrelor or TAM to the $P2Y_{12}$ receptor. In some embodiments, the anti-ticagrelor antibody or fragment thereof is PB2452.

In some aspects, the present disclosure provides a method of restoring platelet aggregation comprising administering pharmaceutical compositions comprising an anti-ticagrelor antibody or fragment thereof to a subject in need. In some aspects, the present disclosure provides a method of decreasing blood loss in a patient receiving ticagrelor comprising administering pharmaceutical compositions comprising an anti-ticagrelor antibody or fragment thereof to a subject in need. In some embodiments, administration of the pharmaceutical composition of the present disclosure inhibits ticagrelor-associated bleeding in a patient.

In some embodiments, administration of pharmaceutical compositions comprising an anti-ticagrelor antibody or fragment thereof to a subject in need clears ticagrelor and/or TAM from the patient's body. In some embodiments, administration of pharmaceutical compositions comprising an anti-ticagrelor antibody or fragment thereof to a subject in need reduces the amount of ticagrelor and/or TAM in a patient's blood. In some embodiments, administration of pharmaceutical compositions comprising an anti-ticagrelor antibody or fragment thereof to a subject in need reduces the amount of ticagrelor in a patient's blood by about 100% to about 5% compared to baseline amounts of ticagrelor and/or TAM. In some embodiments, administration of pharmaceutical compositions comprising an anti-ticagrelor antibody or fragment thereof to a subject in need reduces the amount of ticagrelor in a patient's blood serum by about 90%, about 80%, about 70%, about 60%, about 50%, about 40%, about 30%, about 20%, about 10% or about 5% compared to baseline amounts of ticagrelor and/or TAM.

In some embodiments, administration of pharmaceutical compositions comprising an anti-ticagrelor antibody or fragment thereof to a subject reduces the amount of free ticagrelor and/or TAM in the patient's body. In some embodiments, administration of pharmaceutical compositions comprising an anti-ticagrelor antibody or fragment thereof to a subject in need reduces the amount of free ticagrelor and/or TAM in a patient's blood. In some embodiments, administration of pharmaceutical compositions comprising an anti-ticagrelor antibody or fragment thereof to a subject in need reduces the amount of free ticagrelor and/or TAM in a patient's blood by about 100% to about 15% compared to baseline amounts of ticagrelor and/or TAM. In some embodiments, administration of pharmaceutical compositions comprising an anti-ticagrelor antibody or fragment thereof to a subject in need reduces the amount of free ticagrelor and/or TAM in a patient's blood by about 99.9%, about 99.8%, about 99.7%, about 99.6%, about 99.5%, about 99.4%, about 99.3%, about 99.2%, about 99.1%, about 99%, about 98%, about 97%, about 96%, about 95%, about 94%, about 93%, about 92%, about 91%, about 90%, about 80%, about 70%, about 60%, about 50%, about 40%, about 30%, about 20%, about 10% or about 5% compared to baseline amounts of ticagrelor and/or TAM. In some embodiments, ticagrelor or TAM activity is reversed, inhibited, decreased, or prevented for about 1 hour to about 2 days. In some embodiments, ticagrelor or TAM activity is reversed, inhibited, decreased, or prevented for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 36 hours or about 48 hours. In some embodiments, this reversal, inhibition, decrease, or prevention is observed at the time points disclosed herein.

In some embodiments, administration of the pharmaceutical compositions disclosed herein reverses, inhibits, decreases, or prevents ticagrelor or TAM activity in a subject compared to an untreated subject. In some embodiments, ticagrelor or TAM activity is reversed, inhibited, decreased, or prevented by about 1%, about 5%, about 10%, about 20%, about 30%, about 40%, about 50%, about 60%, about 70%, about 80%, or about 90% or about 100% compared with activity in an untreated subject. In some embodiments, this reversal, inhibition, decrease, or prevention is observed at the time points disclosed herein.

In some embodiments, administration of the pharmaceutical compositions disclosed herein reverses inhibition of platelet aggregation in a subject compared to an untreated subject on ticagrelor. In some embodiments, the inhibition of platelet aggregation is reversed by about 1%, about 5%, about 10%, about 20%, about 30%, about 40%, about 50%, about 60%, about 70%, about 80%, or about 90% or about 100% compared with inhibition of platelet aggregation in an untreated subject on ticagrelor. In some embodiments, this reversal of inhibition of platelet aggregation is observed at the time points disclosed herein.

In some embodiments, administration of pharmaceutical compositions comprising an anti-ticagrelor antibody or fragment thereof to a subject restores platelet aggregation in the patient's blood. In some embodiments, administration of pharmaceutical compositions comprising an anti-ticagrelor antibody or fragment thereof to a subject in need restores platelet aggregation in a patient's blood to about 100% to about 15% compared to baseline levels of normal platelet aggregation. In some embodiments, administration of pharmaceutical compositions comprising an anti-ticagrelor antibody or fragment thereof to a subject in need restores platelet aggregation in a patient's blood to about 100%, about 90%, about 80%, about 70%, about 60%, about 50%, about 40%, about 30%, about 20%, about 10% or about 5% of baseline levels of normal platelet aggregation. In some embodiments, administration of pharmaceutical compositions comprising an anti-ticagrelor antibody or fragment thereof to a subject in need restores platelet aggregation in a patient's blood to about 80% or greater of baseline levels of normal platelet aggregation. In some embodiments, platelet aggregation is restored to at least 80% of baseline levels of normal platelet aggregation in about 1 hour to about 2 days after administration. In some embodiments, platelet aggregation is restored at about 5 minutes, about 10 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 36 hours or about 48 hours. In some embodiments, this restoration is observed at the time points disclosed herein.

In some embodiments, administration of pharmaceutical compositions comprising an anti-ticagrelor antibody or fragment thereof to a subject restores platelet aggregation in the patient's blood as measured by the VerifyNow P2Y$_{12}$ (also known as the VerifyNow PRUTest) assay method (Accriva/Instrumentation Laboratory, San Diego CA). In some embodiments, administration of pharmaceutical compositions comprising an anti-ticagrelor antibody or fragment thereof to a subject in need restores platelet aggregation in a patient's blood as measured by the VerifyNow to about 50 to about 250 platelet reactivity units (PRU). In some embodiments, administration of pharmaceutical compositions comprising an anti-ticagrelor antibody or fragment thereof to a subject in need restores platelet aggregation in a patient's blood as measured by the VerifyNow to about 250 platelet reactivity units (PRU), to about 240 PRU, to about 230 PRU, to about 220 PRU, to about 210 PRU to about 200 PRU, to about 190 PRU, to about 180 PRU, to about 170 PRU, to about 160 PRU, to about 150 PRU, to about 140 PUR, to about 130 PRU, to about 120 PRU, to about 110 PRU, to about 100 PRU, to about 90 PRU, to about 80 PRU, to about 70 PRU, to about 60 PRU, to about 50 PRU. In some embodiments, administration of pharmaceutical compositions comprising an anti-ticagrelor antibody or fragment thereof to a subject in need restores platelet aggregation in a patient's blood to at least 180 PRU. In some embodiments, platelet aggregation is restored to at least 180 PRU in about 1 hour to about 2 days after administration. In some embodiments, platelet aggregation is restored to at least 180 PRU at about 5 minutes, about 10 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 36 hours or about 48 hours. In some embodiments, this restoration is observed at the time points disclosed herein.

In some embodiments, administration of pharmaceutical compositions comprising an anti-ticagrelor antibody or fragment thereof to a subject restores platelet aggregation in the patient's blood as measured by the vasodilator-stimulated phosphoprotein (VASP) method. In some embodiments, administration of pharmaceutical compositions comprising an anti-ticagrelor antibody or fragment thereof to a subject in need restores platelet aggregation in a patient's blood as measured by VASP to about 50% to about 150% baseline platelet reactivity index (PRI). In some embodiments, administration of pharmaceutical compositions comprising an anti-ticagrelor antibody or fragment thereof to a subject in need restores platelet aggregation in a patient's blood as measured by VASP to about 150% baseline platelet reactivity index (PRI), to about 140% baseline PRI, to about 130% baseline PRI, to about 120% baseline PRI, to about 110% baseline PRI, to about 100% baseline PRI, to about 90% baseline PRI, to about 80% baseline PRI, to about 70% baseline PRI, to about 60% baseline PRI, to about 50% baseline PRI. In some embodiments, administration of pharmaceutical compositions comprising an anti-ticagrelor antibody or fragment thereof to a subject in need restores platelet aggregation in a patient's blood to at least 100% baseline PRI. In some embodiments, platelet aggregation is restored to at least 100% baseline PRI in about 1 hour to about 2 days after administration. In some embodiments, platelet aggregation is restored to at least 100% baseline PRI at about 5 minutes, about 10 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 36 hours or about 48 hours. In some embodiments, this restoration is observed at the time points disclosed herein.

Patient Populations

The anti-ticagrelor antibodies or fragments thereof of the present disclosure may be administered to any patient in need. In some embodiments, the patient is at risk of, or has been diagnosed with, Acute Coronary Syndrome (ACS). In some embodiments, the patient is at risk of, or has been diagnosed with myocardial infarction (MI). In some embodiments, the patient has a history of MI. In some embodiments, the patient is receiving, or has received ticagrelor. In some embodiments, the patient is receiving, or has received ticagrelor along with another anti-platelet therapy, such as aspirin.

In some embodiments, the patient has unstable angina, stable ischemic heart disease, in sickle cell disease, including pediatric patients, atrial fibrillation, coronary arterial disease, peripheral arterial disease, ischemic stroke, one or more coronary stents, carotid artery stents, stents following an intracranial aneurysm, or arterio-venous fistulae created for hemodialysis.

In some embodiments, the patient has type 2 diabetes mellitus. In some embodiments, the patient has type 2 diabetes mellitus and coronary disease. In some embodiments, the patient has type 2 diabetes mellitus with a history of percutaneous coronary intervention.

In some embodiments, the patient is at higher risk or increased rate of bleeding associated with ticagrelor treatment. In some embodiments, this ticagrelor-associated bleeding is gastrointestinal bleeding. In some embodiments, this ticagrelor-associated bleeding is intracranial bleeding, or intracranial hemorrhage (ICH). In some embodiments, this ticagrelor-associated bleeding is as a result of traumatic injury, such as a road traffic accident. In some embodiments, the ticagrelor-associated bleeding is categorized as major bleeding. Major bleeding will include any bleeding event which is judged by the treating physician to require reversal. This includes, but is not limited to, bleeding events which are life-threatening, potentially leading to clinically significant disability, requiring surgery to control the bleeding, requiring treatment with blood products, or acute bleeding associated with a clinically important drop in hemoglobin levels.

In some embodiments, the patient requires urgent surgery or intervention. Urgent surgery or intervention is defined as requirement for a surgical operation or medical procedure associated with a risk or perioperative bleeding in a situation where it is not medically advisable to withhold ticagrelor five days. Requirement for urgent surgery may include, but is not limited to, patients in any of the following clinical situations: undergoing surgery or procedures known to be associated with a significant risk of bleeding (such as coronary artery bypass surgery); undergoing surgery or procedures which may have an adverse surgical outcome if bleeding is not carefully controlled (such as neurological, ophthalmologic, or joint replacement surgery); at risk of experiencing perioperative events such as shock, myocardial infarction or stroke if significant perioperative bleeding occurs (especially in elderly patients or those with co-morbidities); at high risk of thrombosis if dual antiplatelet therapy is withheld preoperatively (such as patients with recent coronary stent placement).

In some embodiments, the patient has begun experiencing bleeding before administration of an anti-ticagrelor antibody or fragment thereof. In some embodiments, the patient has not begun experiencing bleeding before administration of an anti-ticagrelor antibody or fragment thereof. In some embodiments, the patient requires surgery, and thus poses increased risk of bleeding due to ticagrelor treatment. In some embodiments, the surgery is urgent surgery. In some embodiments the surgery is emergent surgery.

In some embodiments, the patient is an adult. In some embodiments, the adult patient between 30 and 100 years old or more. In some embodiments, the adult patient is over 40 years old, over 50 years old, over 60 years, over 70 years old, over 80 years old, or over 90 years old. In some embodiments, the adult patient is between 50-64 years old. In some embodiments, the adult patient is between 65-75 years old. In some embodiments, the patient is defined as older (e.g. between the ages of 50 and 64 years old inclusive). In some embodiments, the patient is defined as elderly (e.g. over the age of 65 years or between the ages of 65 and 80 years old inclusive). In some embodiments, the older or elderly patient has been pretreated with ticagrelor and aspirin. In some embodiments, older or elderly patients experience higher exposure to ticagrelor and/or a lower response to ticagrelor compared to younger subjects.

In some embodiments, the patient is a young adult. In some embodiments, the young adult patient between 18 and 30 years old or more. In some embodiments, the patient is a pediatric patient under 18 years of age. In some embodiments, the patient is a pediatric patient under 2 years of age. In some embodiments, the pediatric patient or young adult patient has sickle cell disease.

Pharmaceutical Compositions and Administration

The present disclosure provides pharmaceutical compositions including an anti-ticagrelor antibody or fragment thereof with one or more pharmaceutically acceptable excipients and/or diluents. In some embodiments, the anti-ticagrelor antibody or fragment thereof is PB2452.

The formulations of the present disclosure may include any appropriate excipient known in the art. Exemplary excipients include, but are not limited to, amino acids such as histidine, glycine, or arginine; glycerol; sugars, such as sucrose; surface active agents such as polysorbate 20 and polysorbate 80; citric acid; sodium citrate; antioxidants; salts including alkaline earth metal salts such as sodium, potassium, and calcium; counter ions such as chloride and phosphate; sugar alcohols (e.g. mannitol); preservatives; sugar alcohols (e.g. mannitol, sorbitol); and buffering agents. Exemplary salts include sodium chloride, potassium chloride, magnesium chloride, calcium chloride, sodium phosphate dibasic, sodium phosphate monobasic, sodium phosphate, and potassium phosphate.

In certain embodiments, the formulation may include from about 5 mM histidine/histidine hydrochloride buffer to about 100 mM histidine/histidine hydrochloride buffer. In some embodiments, the formulation includes about 50 mM histidine/histidine hydrochloride buffer, about 40 mM histidine/histidine hydrochloride buffer, about 30 mM histidine/histidine hydrochloride buffer, about 25 mM histidine/histidine hydrochloride buffer, about 20 mM histidine/histidine hydrochloride buffer, or about 15 mM histidine/histidine hydrochloride buffer.

In certain embodiments, the formulation may include from about 100 mM sucrose to about 1 M sucrose. In some embodiments, the formulation may include about 150 mM sucrose, about, about 200 mM sucrose, about 250 mM sucrose, about 290 mM sucrose, about 300 mM sucrose, about 350 mM sucrose, about 400 mM sucrose, or about 500 mM sucrose.

In certain embodiments, the formulation may include a surfactant. In some embodiments the surfactant is a non-ionic surfactant. In some embodiments, the non-ionic surfactant is polysorbate 80. In some embodiments, the formulation may include from about 0.01% w/v polysorbate 80 to about 1.00% w/v polysorbate 80. In some embodiments, the formulation may include about 0.01% w/v, about 0.02% w/v, about 0.03% w/v, about 0.05% w/v, about 0.06% w/v, about 0.07% w/v, about 0.08% w/v, about 0.09% w/v, or about 0.1% w/v polysorbate 80.

In certain embodiments, the formulation may include from about 10 mg/mL anti-ticagrelor antibody or fragment thereof to about 200 mg/mL anti-ticagrelor antibody or fragment thereof. In some embodiments, the formulation may include about 10 mg/mL, about 20 mg/mL, about 30 mg/mL, about 40 mg/mL, about 50 mg/mL, about 60 mg/mL, about 70 mg/mL, about 80 mg/mL, about 90 mg/ml, about 100 mg/mL, about 110 mg/mL, about 120 mg/mL, about 130 mg/mL, about 140 mg/mL, or about 150 mg/mL anti-ticagrelor antibody or fragment thereof.

In some embodiments, the formulation includes 100 mg/mL of the anti-ticagrelor antibody or fragment thereof, 25 mM histidine/histidine hydrochloride buffer, 290 mM sucrose, and 0.05% (w/v) polysorbate 80, pH 6.0.

The formulation can be stored frozen, refrigerated or at room temperature. The storage condition may be below freezing, such as lower than about −10° C., or lower than about −20° C., or lower than about −40° C., or lower than about −70° C. Storage conditions are generally less than the room temperature, such as less than about 32° C., or less than about 30° C., or less than about 27° C., or less than about 25° C., or less than about 20° C., or less than about 15° C. In some embodiments, the formulation is stored at 2°–8° C. For example, the formulation may be isotonic with blood or have an ionic strength that mimics physiological conditions In some embodiments, the formulation is formulated at physiological pH. In some embodiments, the formulation is formulated at a pH in the range of about 5.5 to about 8.5. In some embodiments, the formulation is formulated at a pH in the range of about 6.0 to about 8.0. In some embodiments, the formulation is formulated at a pH in the range of about 6.5 to about 7.5. In some embodiments, the formulation is formulated at a pH of 7.5. In some embodiments, formulations with a lower pH demonstrate improved formulation stability compared to formulations at a higher pH. In some embodiments, formulations with a higher pH demonstrate improved formulation stability compared to formulations at a lower pH.

In some embodiments, the formulation is stable at storage conditions. Stability can be measured using any appropriate means in the art. Generally, a stable formulation is one that shows less than a 5% increase in degradation products or impurities. In some embodiments, the formulation is stable for at least about 1 month, at least about 2 months, at least about 3 months, at least about 4 months, at least about 5 months, at least about 6 months, at least about one year, or at least about 2 years or more at the storage conditions. In some embodiments, the formulation is stable for at least about 1 month, at least about 2 months, at least about 3 months, at least about 4 months, at least about 5 months, at least about 6 months, or at least about one year or more at 25° C.

In some aspects, the formulation is a lyophilized product. In some embodiments, the formulation is a lyophilized product containing about 1 g to about 36 g of the anti-ticagrelor antibody or fragment thereof. In some embodiments, the formulation is a lyophilized product containing about 6 g of the anti-ticagrelor antibody or fragment thereof. In some aspects, following reconstitution with water for injection, the product may be further diluted into 0.9% saline for intravenous (iv) infusion. In some embodiments, the product is not lyophilized and is further diluted into 0.9% saline for intravenous (iv) infusion.

In one aspect, the formulations of the disclosure are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). In certain specific aspects, the endotoxin and pyrogen levels in the composition are less than about 1 EU/mg, or less than about 0.1 EU/mg, or less than about 0.01 EU/mg, or less than about 0.001 EU/mg. In some embodiments, the endotoxin and pyrogen levels in the composition are 0.0138 EU/mg or less.

When used for in vivo administration, the formulations of the disclosure should be sterile. The formulations of the disclosure may be sterilized by various sterilization methods, including sterile filtration, radiation, etc. In one aspect, the formulation is filter-sterilized with a pre-sterilized 0.22-micron filter. Sterile compositions for injection can be formulated according to conventional pharmaceutical practice as described in "Remington: The Science & Practice of Pharmacy", 21$^{st}$ ed., Lippincott Williams & Wilkins, (2005).

In some embodiments, the pharmaceutical composition is formulated for intravenous administration. In some embodiments, the formulation is administered intravenously over about 5 minutes to 48 hours. In some embodiments, the formulation is administered in any appropriate volume. In some embodiments, the formulation is administered in a total volume of about 30 mL to about 2 L. In some embodiments, the formulation is administered in a total volume of about 30 mL, about 40 mL, about 50 mL, about 100 mL, about 125 mL, about 150 mL, about 175 mL, about 200 mL, about 225 mL, about 250 mL, about 275 mL, about 300 mL, about 400 mL, about 500 mL, about 1 L, about 1.5 L, or about 2 L. In some embodiments, the formulation is administered intravenously over about 30 minutes in a total volume of about 250 mL. In some embodiments, the formulation is first administered as a bolus, followed by a longer infusion. In some embodiments, the longer infusion following the bolus is about 4 hours. In some embodiments, the longer infusion following the bolus is about 8 hours. In some embodiments, the longer infusion following the bolus is about 12 hours. In some embodiments, the longer infusion following the bolus is about 18 hours. In some embodiments, the longer infusion following the bolus is about 24 hours. In some embodiments, the longer infusion following the bolus is about 36 hours.

In some embodiments, the concentration of anti-ticagrelor antibody or fragment thereof in the formulation varies between 0.4 mg/mL up to 72 mg/mL in a single IV infusion, 250 mL to be delivered over 30 minutes to 12 hours in doses of 0.1 g, 0.3 g, 1.0 g, 3 g, 9 g, 180 g, 24 g, 30 g, 36 g or 48 g or intermediate doses between 9 to 48 g. In some cases, a portion of the therapeutic composition is infused (up to about 12 g) at a faster rate (equivalent to a bolus) for the first 5-20 minutes of the infusion.

In some embodiments, the anti-ticagrelor antibody or fragment thereof is stored in one or more glass vials and subsequently transferred to an infusion bag for administration. In some embodiments, the anti-ticagrelor antibody or fragment thereof is stored in one or more glass vials and subsequently transferred to a syringe for administration using a syringe pump. In some embodiments, the anti-ticagrelor antibody or fragment thereof is stored in pre-filled syringe for administration using a syringe pump. In some embodiments, the anti-ticagrelor antibody or fragment thereof is stored in an IV container, such as Baxter Galaxy Liquid Premix System or Baxter Galaxy Frozen Premix System.

In some embodiments, the antibody or fragment thereof is administered to effect rapid and prolonged reversal of ticagrelor activity. In some embodiments, the infusion rate remains constant over the entire infusion. In some embodiments, the infusion rate varies over the infusion time. In some embodiments, a greater amount of the pharmaceutical composition is administered first in the infusion, and the amount is tapered during the rest of the infusion.

In some embodiments, the infusion duration lasts between about 5 minutes and about 36 hours. In some embodiments, the infusion regimen is selected from, but not limited to infusion of about 3 g to about 36 g at a constant infusion rate over about 1 hour to about 24 hours, infusion of about 3 g over about 5 minutes, followed by infusion of about 15 grams over about 8 hours, infusion of about 6 g over about 15 minutes, followed by infusion of about 6 grams over about 3 hours, followed by infusion of about 6 g over about 8.75 hours, infusion of about 6 g over about 15 minutes, followed by infusion of about 6 grams over about 4 hours, followed by infusion of about 6 g over about 12 hours, infusion of about 6 g over about 10 minutes, followed by infusion of about 6 grams over about 3 hours, followed by infusion of about 6 g over about 13 hours, infusion of about 12 g over about 10 minutes, followed by infusion of about 12 grams over about 6 hours, followed by infusion of about 12 g over about 18 hours.

In some embodiments, if rapid reversal of ticagrelor activity is desired (e.g. during an active bleed in a patient), the antibody or fragment thereof of the present disclosure may be administered according to the below:

1. about 3 g to about 6 g infused over about 5 to about 15 minutes, followed by about 3 g to about 6 g infused over about 1 to about 3 hours, followed by about 3 g to about 6 g infused over about 3 to about 8 hours.
2. about 3 g to about 6 g infused over about 5 to about 15 minutes, followed by about 6 g to about 12 g infused over about 1 to about 3 hours, followed by about 6 g to about 12 g infused over about 3 to about 8 hours.
3. about 3 g to about 6 g infused over about 5 to about 15 minutes, followed by about 6 g to about 12 g infused over about 1 to about 3 hours, followed by about 1 g/hour infused over up to about 24 to about 48 hours.
4. about 9 g infused over about 5 to about 30 minutes, followed by about 1 g/hr to about 3 g/hr infused over about 3 to about 8 hours.
5. about 9 g to about 24 g infused over about 1 to about 4 hours.

In some embodiments, if the patient is about to undergo surgery, the antibody or fragment thereof of the present disclosure may be administered according to the below:

1. about 3 to about 6 g infused over about 5 to about 30 minutes, followed by about 3 to about 6 g infused over about 3 to about 6 hours, followed by about 1 g/hr infused over up to about 12 to about 24 hours;
2. about 3 to about 6 g infused over about 5 to about 15 minutes, followed by about 3 to about 6 g infused over about 1 to about 3 hours, followed by about 1 g/hr infused over about 12 to about 24 hours.
3. about 9 g to about 24 g infused over about 1 to about 4 hours.

In some embodiments, if the patient is taking one or more additional drugs that impact ticagrelor exposure, such as drugs that inhibit the activity of cytochrome P450 isoform 3A (CYP3A), leading to increased exposure to ticagrelor, or the patient has taken an overdose of ticagrelor, the antibody or fragment thereof of the present disclosure may be administered according to the below:

1. about 6 to about 12 g infused over about 5 to about 30 minutes, followed by about 6 to about 12 g infused over about 3 to about 6 hours, followed by about 6 to about 12 g infused over up to about 12 to about 24 hours;
2. about 6 to about 12 g infused over about 5 to about 15 minutes, followed by about 6 to about 12 g infused over about 1 to about 3 hours, followed by about 0.5-1 g/hr infused over about 12 to about 24 hours.
3. about 18 g to about 36 g infused over about 3 to about 6 hours.

The formulations may conveniently be presented in unit dosage form and may be prepared by any method known in the art of pharmacy. Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient (e.g., "a therapeutically effective amount"). The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Suitable dosages may range from about 1000 mg to about 36 g, or from about 9 g to about 24 g, or from about 9 g to about 15 g, or from about 1 g to about 3 g. In some embodiments, the dose may be about 1000 mg, about 3 g, about 9 g, about 18 g, about 24 g, about 30 g, about 36 g, or about 48 g. In some embodiments, the amount of anti-ticagrelor antibody or fragment thereof administered to a patient depends on the amount of ticagrelor the patient has received. In some embodiments, the amount of anti-ticagrelor antibody or fragment thereof administered to a patient depends on the body weight of the patient.

The dose of anti-ticagrelor antibody or fragment thereof administered will be that dose which causes the reversal of ticagrelor-induced platelet disaggregation in 95% of the simulated patient population, with reversal taken to be the reversal of the platelet disaggregation to less than 10% of baseline.

In some embodiments, the patient has been administered at least 180 mg ticagrelor. In some embodiments, the patient has been administered a loading dose of at least 180 mg ticagrelor with 90 mg subsequently administered twice a day. In some embodiments, the patient has been administered ticagrelor at least three days prior to administration of an anti-ticagrelor antibody or fragment thereof. In some embodiments, the patient is administered ticagrelor at the same time as administration of an anti-ticagrelor antibody or fragment thereof. In some embodiments, the patient has been administered an overdose of ticagrelor.

Note that the disclosure similarly contemplates that formulations suitable for diagnostic and research use may also be made. The concentration of active agent in such formulations, as well as the presence or absence of excipients and/or pyrogens can be selected based on the particular application and intended use.

It should be understood that singular forms such as "a," "an," and "the" are used throughout this application for convenience, however, except where context or an explicit statement indicates otherwise, the singular forms are intended to include the plural. All numerical ranges should be understood to include each and every numerical point within the numerical range, and should be interpreted as reciting each and every numerical point individually. The endpoints of all ranges directed to the same component or property are inclusive, and intended to be independently combinable.

The term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein.

EXAMPLES OF NON-LIMITING EMBODIMENTS OF THE DISCLOSURE

Embodiments, of the present subject matter disclosed herein may be beneficial alone or in combination, with one or more other embodiments. Without limiting the foregoing description, certain non-limiting embodiments of the disclosure, numbered 1-42 are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiments explicitly provided below.

Embodiment 1. A method of reversing ticagrelor-associated bleeding, or the risk of said bleeding, in a patient in need thereof comprising administering to said patient a composition comprising an effective amount of a pharmaceutical composition comprising an antibody or fragment thereof that binds to ticagrelor ((1S,2S,3R,5S)-3-[7-{[(1R, 2S)-2-(3,4-difluorophenyl)cyclopropyl]amino}-5-(propyl-thio)-3H-[1,2,3]triazolo[4,5-d]pyrimidin-3-yl]-5-(2-hy-droxyethoxy)cyclopentane-1,2-diol) or a metabolite or derivative thereof.

Embodiment 2. The method of embodiment 1, wherein the antibody or a fragment thereof comprises complementarity-determining region (CDR) combinations selected from the group consisting of:
  a) SEQ ID NO:53 (VH CDR1), SEQ ID NO:54 (VH CDR2), SEQ ID NO:55 (VH CDR3), SEQ ID NO:58 (VL CDR1), SEQ ID NO:59 (VL CDR2), and SEQ ID NO:60 (VL CDR3);
  b) SEQ ID NO:63 (VH CDR1), SEQ ID NO:64 (VH CDR2), SEQ ID NO:65 (VH CDR3), SEQ ID NO:68 (VL CDR1), SEQ ID NO:69 (VL CDR2), and SEQ ID NO:70 (VL CDR3); and
  c) SEQ ID NO:73 (VH CDR1), SEQ ID NO:74 (VH CDR2), SEQ ID NO:75 (VH CDR3), SEQ ID NO:78 (VL CDR1), SEQ ID NO:79 (VL CDR2), and SEQ ID NO:80 (VL CDR3).

Embodiment 3. The method of embodiment 1 or 2, wherein the antibody or a fragment thereof
  comprises a combination of heavy chain variable region (VH) and light chain variable region (VL) sequences selected from the group consisting of SEQ ID NO:52 and SEQ ID NO:57; SEQ ID NO:62 and SEQ ID NO:67; and SEQ ID NO:72 and SEQ ID NO:77.

Embodiment 4. The method of any of embodiments 1-4, wherein the patient has been administered ticagrelor before administration of the anti-ticagrelor antibody or fragment thereof.

Embodiment 5. The method of any of embodiments 1-5, wherein the antibody or fragment thereof is a Fab and the patient is administered a dose between about 1 g and about 48 g.

Embodiment 6. The method of embodiment 5, wherein the dose is between about 9 g to about 18 g of the Fab.

Embodiment 7. The method of embodiment 5 or 6, wherein the patient is administered a dose of about 1 g, about 3 g, about 9 g, about 18 g, about 24 g, about 30 g, about 36 g or about 48 g of the Fab.

Embodiment 8. The method of any of embodiments 1-7, wherein the pharmaceutical composition is administered to the patient intravenously.

Embodiment 9. The method of embodiment 8, wherein the pharmaceutical composition is administered intravenously over about 15 minutes to about 36 hours.

Embodiment 10. The method of any of embodiments 1-9, wherein the pharmaceutical composition is administered in two or more segments.

Embodiment 11. The method of embodiment 10, wherein the first segment is a bolus.

Embodiment 12. The method of embodiment 10 or 11, wherein the administration rates for each of the segments differ.

Embodiment 13. The method of any of embodiments 10-12, wherein the administration rates for each of the segments differ for successive segments of the infusion.

Embodiment 14. The method of any of embodiments 10-13, wherein the pharmaceutical composition is administered in three or more segments, wherein the administration rates for each of the segments differ for successive segments of the infusion.

Embodiment 15. The method of any of embodiments 5-14, wherein the pharmaceutical composition is administered in the following schedule: 12 g infused over 10 minutes, followed by 12 g over 6 hours, followed by 12 g over 18 hours.

Embodiment 16. The method of any of embodiments 1-15, wherein the pharmaceutical composition comprises about 50 mg/mL to about 200 mg/mL of the anti-ticagrelor antibody or fragment thereof, about 5 mM to about 50 mM histidine/histidine hydrochloride buffer, about 100 mM to about 300 mM sucrose, and about 0.01% (w/v) to about 1.0% (w/v) polysorbate 80, pH 5.5 to 6.5

Embodiment 17. The method of embodiment 16, wherein the pharmaceutical formulation comprises 100 mg/mL of the anti-ticagrelor antibody or fragment thereof, 25 mM histidine/histidine hydrochloride buffer, 290 mM sucrose, and 0.05% (w/v) polysorbate 80, pH 6.0.

Embodiment 18. The method of embodiment 16 or 17, wherein the pharmaceutical formulation is diluted in saline for administration.

Embodiment 19. The method of any of embodiments 1-18, wherein the ticagrelor-associated bleeding is major bleeding.

Embodiment 20. The method of embodiment 19, wherein the major bleeding is characterized by being life-threatening, potentially leading to clinically significant disability, requiring surgery to control the bleeding, requiring treatment with blood products, or is acute bleeding associated with a clinically important drop in hemoglobin.

Embodiment 21. The method of any of embodiments 1-20, wherein the patient requires urgent surgery or intervention.

Embodiment 22. The method of embodiment 21, wherein the urgent surgery or intervention is known to be associated with a significant risk of bleeding, such as coronary artery bypass surgery, has an adverse surgical outcome if bleeding is not carefully controlled, neurological, ophthalmologic, or joint replacement surgery, associated with risk of experiencing perioperative events; or in a patient at high risk of thrombosis if dual antiplatelet therapy is withheld preoperatively.

Embodiment 23. The method of any of embodiments 1-22, wherein the patient is at risk of developing, or has been diagnosed with Acute Coronary Syndrome (ACS).

Embodiment 24. The method of any of embodiments 1-23, wherein the patient is at risk of developing, or has been diagnosed with a disease selected from the group consisting of myocardial infarction (MI), unstable angina, stable ischemic heart disease, in sickle cell disease, including pediatric patients, atrial fibrillation, coronary arterial disease, peripheral arterial disease, ischemic stroke, one or more coronary stents, carotid artery stents, stents following an intracranial aneurysm, and arterio-venous fistulae created for hemodialysis.

Embodiment 25. The method of any of embodiments 1-24, wherein the patient is a pediatric patient.

Embodiment 26. The method of embodiment 25, wherein the pediatric patient is younger than 18 years old.

Embodiment 27. The method of embodiment 26, wherein the pediatric patient is younger than 2 years old.

Embodiment 28. The method of any of embodiments 1-24, wherein the patient is an adult patient.

Embodiment 29. The method of embodiment 28, wherein the adult patient is between 18 and 64 years old inclusive.

Embodiment 30. The method of embodiment 28, wherein the patient is over 65 years old.

Embodiment 31. The method of embodiment 30, wherein the patient is between 65 and 80 years old inclusive.

Embodiment 32. The method of any of embodiments 1-31, wherein the patient has been administered aspirin (acetylsalicylic acid).

Embodiment 33. The method of any of embodiments 1-32, wherein administration of the antibody or fragment thereof reverses ticagrelor activity.

Embodiment 34. The method of embodiment 33, wherein administration of the antibody or fragment thereof restores platelet function.

Embodiment 35. The method of embodiment 34, wherein administration of the antibody or fragment thereof restores platelet aggregation.

Embodiment 36. The method of embodiment 35, wherein administration of the antibody or fragment thereof restores platelet aggregation to at least 80% of baseline.

Embodiment 37. The method of embodiment 35 or 36, wherein administration of the antibody or fragment thereof restores platelet aggregation within 1 minute to 60 minutes of administration.

Embodiment 38. The method of embodiment 37, wherein administration of the antibody or fragment thereof restores platelet aggregation within 5 minutes of administration.

Embodiment 39. The method of any of embodiments 35 to 38, wherein administration of the antibody or fragment thereof provides a sustained restoration of platelet aggregation.

Embodiment 40. The method of embodiment 39, wherein the restoration of platelet aggregation is sustained for at least 12 hours after administration.

Embodiment 41. The method of embodiment 40, wherein the restoration of platelet aggregation is sustained for at least 16 hours after administration.

Embodiment 42. The method of embodiment 41, wherein the restoration of platelet aggregation is sustained for at least 24 hours after administration.

This disclosure is further illustrated by the following non-limiting examples.

EXAMPLES

Example 1—A Phase 1, Randomized, Double-Blind, Placebo-Controlled, Single Ascending Dose Study to Evaluate the Safety, Tolerability, Pharmacokinetics, and Pharmacodynamics of PB2452 with and without Ticagrelor Pre Treatment in Healthy Volunteers Primary Objective: 1) To evaluate the safety and tolerability of single ascending intravenous (IV) doses of PB2452 with or without oral ticagrelor; 2) To evaluate the effect of single ascending doses of PB2452 on ticagrelor antiplatelet activity using light transmittance aggregometry (LTA).

Secondary Objectives: 1) To determine the pharmacokinetics of ascending doses of IV PB2452 in the presence and absence of ticagrelor; 2) To determine the pharmacokinetics of ticagrelor and its active metabolite TAM in the presence and absence of PB2452; 3) To assess the effectiveness of a single IV PB2452 dose in reversing ticagrelor antiplatelet activity by measuring P2Y$_{12}$ reaction units (PRU) with VerifyNow™ P2Y$_{12}$ assay and platelet reactivity index (PRI) with vasodilator stimulated phosphoprotein (VASP) phosphorylation assay by enzyme-linked immunosorbent assay (ELISA); 3) To evaluate the pharmacokinetics and pharmacodynamics of restarting a single dose of oral ticagrelor 24 hours after IV PB2452 administration if a sixth dose of ticagrelor is given; 4) To evaluate the immunogenicity potential of PB2452

Exploratory Objectives: To evaluate the effect of PB2452 on the pharmacokinetic (PK) profile of unbound ticagrelor and unbound TAM plasma concentrations.

Study design and methodology: This is a Phase 1, first-in-human, randomized, double-blind, placebo-controlled, single ascending dose, sequential group study to evaluate the safety, tolerability, pharmacokinetics, and pharmacodynamics of PB2452 with and without ticagrelor pretreatment when administered to healthy male and female subjects. All references to study drug within the content of the protocol apply to PB2452 or matching placebo.

This study will have up to 10 cohorts and up to a total of approximately 80 subjects. The starting dose of PB2452 will be 100 mg and the planned doses for subsequent cohorts are 300, 1000, 3,000, 9,000, and 18,000 mg. Other doses may also be tested and may exceed 18,000 mg.

The study will consist of a screening period (Days −45 to −4), check-in/pretreatment (Day −3 to Day −1), an in-house treatment period (Days 1 through 3), and follow-up visits (Days 4, 7, and 28 [+2 days]). Subjects will receive an IV dose of study drug on Day 1. On Day 1, subjects who meet all of the inclusion criteria and none of the exclusion criteria will be randomly assigned to receive PB2452 or placebo in a ratio of 3:1 in all treatment cohorts:

Cohorts 1 to 3: For the initial cohort (Cohort 1), 4 healthy subjects will be randomly assigned in a 3:1 ratio of active treatment to placebo (3A:1P) to receive a single 100 mg IV dose of study drug over 30 minutes. For the second cohort (Cohort 2), 4 healthy subjects will be randomly assigned (3A:1P) to receive a single 300 mg IV dose of study drug over 30 minutes. For the third cohort (Cohort 3), 4 healthy subjects will be randomly assigned (3A:1P) to receive a 1,000 mg IV dose of study drug over 30 minutes.

Cohorts 4 to 6: Provided no safety concerns arise in previously dosed cohorts, 8 subjects in each of Cohorts 4 through 6 will be randomly assigned in a 3:1 ratio (6A:2P) to receive a single IV dose of study drug within approximately 2 hours after the 5th dose of ticagrelor pretreatment. For ticagrelor pretreatment, subjects will receive an oral loading dose of 180 mg ticagrelor in the morning (Day −2), followed by 90 mg ticagrelor orally every 12 hours for 4 additional doses, prior to administration of a single IV dose of study drug within approximately 2 hours after the 5th ticagrelor dose (Day 1). Subjects in each of Cohorts 4 through 6 will receive ticagrelor pretreatment, as described above, and a single IV dose of 1,000, 3,000, or 9,000, or 18,000 mg of study drug, respectively, over 30 minutes. Cohorts 4 through 6 will be dosed sequentially following the safety and dose-escalation assessment of each preceding dose cohort.

Cohorts 7 to 10: For Cohort 7, following ticagrelor pretreatment, subjects will be randomly assigned in a 3:1 ratio (6A:2P) to receive a single IV dose of study drug. The intravenous infusion will be initiated 2 hours after the 5th ticagrelor dose and will administer PB2452 continuously, but at different rates during the infusion period as follows: 3,000 mg over 5 minutes, followed by 15,000 mg for 7 hours 55 minutes.

For cohort 8, the infusion rates during the infusion period will be as follows: 6,000 mg over 15 minutes, followed by 6,000 mg for 3 hours, followed by 6,000 mg for 8.75 hours. For cohort 9, the infusion rates during the infusion period will be as follows: 6,000 mg over 15 minutes, followed by 6,000 mg for 4 hours, followed by 6,000 mg for 12 hours. For cohort 10, the infusion rates during the infusion period will be as follows: 6,000 mg over 10 minutes, followed by 6,000 mg for 3 hours, followed by 6,000 mg for 13 hours.

Subjects in Cohorts 1 through 3 will check in to the clinical site on Day −1. On Day 1, subjects will receive a single IV dose of study drug in the morning. Subjects will be discharged from the clinical site on Day 3 and will return for follow-up visits on Days 4, 7, and 28 (+2 days).

Subjects in Cohorts 4 through 10 will check into the clinical site on Day −3. In the morning on Day −2, subjects will begin pretreatment with ticagrelor. On Day 1, subjects will receive a single IV dose of study drug in the morning. Subjects in Cohorts 4 through 8 (and also Cohort 9 if they do not receive a 6th dose of ticagrelor) will be discharged from the clinical site on Day 3 and will return for follow-up visits on Days 4, 7, and 28 (+2 days). Cohort 10 will be discharged from the clinical site on Day 7 and will return for their final follow up visit on Day 28 (+2 days).

On Day 2, subjects in Cohort 9 may receive an additional dose of ticagrelor in the morning 24 hours after the initiation of the study drug infusion. In this case subjects will be discharged from the clinical site on Day 4 and will return for follow-up visits on Days 7 and 28 (+2 days). If the 6th ticagrelor dose is not given they will be discharged from the unit on Day 3 and will return for follow-up visits on Days 4, 7, and 28. The decision on whether to administer this 6th dose of ticagrelor will be made based upon review of data from prior cohorts.

Plasma samples for PK and pharmacodynamics (PD) analysis of PB2452, ticagrelor, and its active metabolite, TAM, and urine samples for the PK analysis of ticagrelor and TAM will be collected at specified intervals up to 28 days after dosing. Hour 0 will be the initiation of the study drug infusion for all cohorts.

Safety and tolerability will be carefully monitored throughout the study. Immunogenicity will be determined in all subjects at baseline and for up to 28 days following administration of the study drug.

Sentinel Dosing: Dosing for Cohort 1 (first exposure of PB2452 in humans) will proceed with two sentinel subjects initially randomly assigned to receive a single IV dose of study drug. Blinded safety data from the sentinel subjects up to 24 hours following the study drug infusion will be reviewed by the investigator before the remaining 2 subjects in Cohort 1 are dosed. The remaining subjects will be dosed at least 24 hours after the sentinel subjects. Additionally, dosing for Cohort 4 (first exposure of the combination of PB2452 with ticagrelor in humans) will proceed with 2 sentinel subjects pre-treated with ticagrelor prior to receiving a single IV dose of PB2452 or placebo randomized in a 1:1 ratio of active to placebo. Blinded safety data from the sentinel subjects up to 24 hours following the ticagrelor and study drug administration will be reviewed by the investigator before the remaining 6 subjects in Cohort 4 are dosed. The remaining subjects will be dosed at least 24 hours after the sentinel subjects.

Dose Escalation: A safety review committee (SRC) will be formed for blinded reviews of safety (e.g., clinical laboratory results, adverse events [AEs], 12-lead electrocardiograms [ECGs], vital signs) and available PK data through Day 4 for each dose cohort. Dose escalation to successive cohorts will be based upon safety of the preceding cohort. The investigator will make a recommendation on whether to proceed to the next predefined dose level, pause dosing for review of additional safety and/or PK data, or to adjust the dose of the next dose cohort. The decision to adjust or pause the dose or proceed to the next cohort will be made by the SRC. The safety data will be reviewed in a blinded manner and must be deemed acceptable to the SRC prior to dosing of the next higher dose group.

Based on the review of safety and PK data, if available, the SRC may choose to repeat a dose level, administer a dose less than the previous dose, or escalate to a dose lower than the next planned dose. The SRC has the authority to make the decision to proceed with dose escalation after review of the available safety data regarding any DLTs.

Stopping Criteria: After completion of Day 4 for each dose cohort, the SRC will review and assess all available safety (e.g., clinical laboratory results, AEs, ECGs, vital signs), tolerability, and available PK data to make a dose escalation decision for next dose cohort. Dose escalation will be suspended if any of the following scenarios occur after confirmation of receipt of PB2452 and review by the SRC:

Any preclinical or clinical events that, in the opinion of the SRC, contraindicate further dosing of additional subjects with PB2452;

Any serious adverse event (SAE) in a dose cohort;

Data from the previous dose cohort indicating safety concerns for the next cohort to be dosed at a higher level, such as unanticipated responses (e.g., clinically significant changes in clinical laboratory data, ECGs, cardiac telemetry, vital signs, or physical examinations);

Two or more subjects in a dose cohort experience any DLT, or 1 subject experiences a grade 2 or higher AE (DLT) that in the opinion of the SRC warrants suspension of dose escalation;

Two or more subjects have >3× upper limit of normal (ULN) of either alanine aminotransferase (ALT) or aspartate aminotransferase (AST), or >2×ULN for bilirubin or alkaline phosphatase where no other reason can be found to explain the increases; or One or more subjects experiences a grade 2 or higher infusion-related reaction despite having been pre-medicated for infusion-related reactions.

Dose escalation may also be suspended if, in the opinion of the SRC or sponsor, any other significant safety or tolerability issues are identified in the comprehensive review of available data that warrant further evaluation before additional subjects are dosed. This may include emerging nonclinical data, clinically relevant AEs, or relevant data from other sources indicating safety concerns even if the event(s) per se does not meet the protocol-specified definition of a dose-limiting toxicity. The SRC has the authority to make the decision to proceed with dose escalation after review of the available safety data regarding SAEs and other stopping criteria.

Inclusion Criteria:

1) The subject is male or female between 18 and 50 years of age, inclusive for Cohorts 1-10 male or female subjects.

2) The subject has a body mass index between 18 and 35 $kg/m^2$ and a weight of ≥50 kg but ≤120 kg, inclusive, at screening.

3) The subject is considered by the investigator to be in good general health as determined by medical history, clinical laboratory test results, vital sign measurements, 12-lead ECG results, and physical examination findings at screening.

4) Female subjects of childbearing potential must not be pregnant, lactating, or planning to become pregnant before 3 months after the last dose of study drug, and have a negative serum pregnancy test at screening and check-in. Female subjects of childbearing potential must use 2 effective methods of birth control (i.e., oral, implantable, patch, or injectable contraceptives in combination with a condom, hormone-containing intrauterine device that has been in place for at least 2 months prior to screening in combination with a condom, double-barrier method [i.e., condoms, sponge, diaphragm, or cervical cap with spermicidal gels or cream], or vasectomy for male subjects or male partners of female subjects) from 30 days before study drug administration through the end of the study. Women are considered not to be of childbearing potential if they have fulfilled one of the following criteria: documentation of irreversible surgical sterilization (i.e., hysterectomy, or bilateral oophorectomy [not tubal ligation]), or postmenopausal (defined as amenorrhea for 12 consecutive months following cessation of all exogenous hormonal treatments, and documented plasma follicle-stimulating hormone level >40 IU/mL, or amenorrhea for 24 consecutive months). Male subjects with partners of childbearing potential must agree to use appropriate and effective measures of contraception (e.g., condom plus diaphragm with spermicide; condom plus spermicide) during the study and for 30 days after the last dose of study drug, and to refrain from donating sperm for at least 7 days prior to the dose of study drug and until at least 90 days following the last dose of study drug.

5) The subject agrees to comply with all protocol requirements.

6) The subject is able to provide written informed consent.

Exclusion Criteria

1. History of any clinically significant acute or chronic disease or medical disorder.

2. History or presence of gastrointestinal, hepatic (with the exception of Gilbert's syndrome), or renal disease or renal insufficiency (i.e., estimated glomerular filtration rate <60 ml/min/1.73 m$^2$), or any other condition known to interfere with absorption, distribution, metabolism, or excretion of drugs.

3. Any clinically significant illness, medical/surgical procedure, or trauma within 4 weeks of the administration of study drug or any planned surgical procedure that will occur during the study (from screening through the Day 28 follow up visit).

4. Any clinically significant abnormal findings in physical examination, vital signs, laboratory assessments, and ECG parameters identified during screening or check-in. Note: abnormal test results may be repeated once for confirmation.

Specific vital sign exclusionary criteria occurring after 10 minutes of supine rest are any of the following:

Systolic blood pressure >150 mm Hg;

Diastolic blood pressure >90 mm Hg; or

Heart rate <50 or >100 beats per minute.

Specific exclusionary criteria for ECG parameters at screening or check-in are any of the following:

Prolonged Fridericia-corrected QT interval (QTcF)>450 milliseconds (msec), shortened QTcF<340 msec, or pause >3 seconds, or family history of long QT syndrome;

Prolonged PR (PQ) interval >240 msec, intermittent second- or third-degree atrioventricular (AV) block or AV dissociation, or shortened PR interval <120 msec;

Incomplete, full, or intermittent bundle branch block (QRS<110 msec with normal QRS and T wave morphology is acceptable if there is no evidence of left ventricular hypertrophy;

5. Any history of arterial or venous thrombosis, including any of the following:

History of transient ischemic attack, cardiovascular accident, stroke (ischemic or hemorrhagic), unstable angina, myocardial infarction, or peripheral arterial disease; or History of deep venous thrombosis, pulmonary embolus, thrombophlebitis, or cavernous malformations.

6. Any increased risk of bleeding, including the following:

Recent history (within 30 days preceding the first dose of study drug) of gastrointestinal bleeding;

Any history of severe head trauma, intracranial hemorrhage, intracranial neoplasm, arteriovenous malformation, aneurysm, or proliferative retinopathy;

Any history of intracranial, intraocular, retroperitoneal, or spinal bleeding;

Any recent (within 30 days preceding the first dose of study drug) major trauma;

History of hemorrhagic disorders that may increase the risk of bleeding (e.g., hemophilia, von Willebrand's disease);

Receiving chronic treatment with nonsteroidal anti-inflammatory drugs (including aspirin [greater than 100 mg daily]), anticoagulants, or other antiplatelet agents that cannot be discontinued (including clopidogrel, prasugrel, ticlopidine, dipyridamole, or cilostazol).

Have taken, within 30 days of screening, any oral or parenteral anticoagulant, including low molecular-weight heparin;

Have taken non-steroidal anti-inflammatory medications, including aspirin within 14 days of screening;

7. The subject has a positive test result for hepatitis B surface antigen, hepatitis C virus antibody, or human immunodeficiency virus types 1 or 2 antibodies at screening.

8. Any ongoing or recent (i.e., during the screening period) minor medical complaints that may interfere with the interpretation of the study data or are considered unlikely to comply with study procedures, restrictions, and requirements as judged by the investigator.

9. Any risk of bradycardic events (e.g., known sick sinus syndrome, atrial fibrillation, or second- or third-degree AV block).

10. Concomitant oral or IV therapy with strong CYP3A inhibitors, CYP3A substrates with narrow therapeutic indices, or strong CYP3A inducers, which cannot be stopped within at least 5 half-lives, but not shorter than 10 days, before randomization (a list of examples can be found in Section 6.2).

11. Any prescription (excluding hormonal birth control) or over-the-counter medications (except paracetamol [up to 2 g per day], including herbal or nutritional supplements, within 14 days before the first dose of study drug.

12. The subject has consumed grapefruit or grapefruit juice, Seville orange or Seville orange-containing products (e.g., marmalade), or alcohol-, or xanthine-containing products within 48 hours before dosing with study drug.

13. The subject is participating in any other study or is taking part in a non-medication study which, in the opinion of the investigator, would interfere with the outcome of the study.

14. The subject has received another new chemical entity (defined as a compound which has not been approved for marketing) or any marketed or investigational biologic agent within 30 days of the administration of study drug in this study. The period of exclusion begins 30 days after the final dose or 5 half-lives of the experimental medication has elapsed, whichever is longer.

15. The subject has involvement with any Sponsor or study site employee or their close relatives (e.g., spouse, parents, siblings, or children whether biological or legally adopted).

16. The subject has previously received PB2452 or had been randomized to receive study drug in an earlier cohort for this study.

17. The subject is a smoker or has used nicotine or nicotine-containing products (e.g., snuff, nicotine patch, nicotine chewing gum, mock cigarettes, or inhalers) within 3 months before the infusion of study drug.

18. The subject has a known or suspected history of drug abuse (including alcohol) or has a positive test result for drugs of abuse, alcohol, or cotinine (nicotine level above 300 ng/mL) at screening or check-in.

19. The subject has been involved in strenuous activity or contact sports within 24 hours before the infusion of study drug and while confined in the clinical site.

20. The subject has donated blood or plasma within 1 month of screening or any blood donation/loss more than 500 mL during the 3 months prior to the infusion of study drug.

21. The subject has a history of severe allergy/hypersensitivity or ongoing allergy/hypersensitivity, as judged by the investigator or history of hypersensitivity to drugs with a similar chemical structure or class to ticagrelor, any biologic therapeutic agent, or any significant food allergy that could preclude a standard diet in the clinical site.

22. Concern for the inability of the subject to comply with study procedures and/or follow-up, or, in the opinion of the investigator, the subject is not suitable for entry into the study.

Evaluation Criteria:

Safety Assessments: Safety and tolerability will be assessed by monitoring and recording of AEs, clinical laboratory test results (hematology, coagulation, serum chemistry, and urinalysis), vital sign measurements (systolic and diastolic blood pressures, oral body temperature, respiratory rate, and heart rate), 12-lead ECG results, cardiac telemetry monitoring, immunogenicity, and physical examination findings.

Pharmacokinetic Assessments

Plasma Collection: Blood samples for PK analysis of PB2452 in plasma will be collected from all subjects at the following time points: before dosing (within 10 minutes prior to the initiation of study drug infusion and up to 28 days after the initiation of study drug infusion. Specific collection times for each cohort are listed in the table below:

| Summary of Pharmacokinetic Assessments for PB2452 | |
| --- | --- |
| Cohorts 1-6 | −10 minutes, 0.5, 1, 1.5, 2, 3, 4, 6, 8, 12, 24, 48, 72 hours, 7 and 28 days |
| Cohorts 7-10 | −10 minutes, 5 minutes, 0.25, 0.5, 1, 2, 3, 4, 6, 8, 8.25, 9, 10, 11, 12, 16, 20, 24, 32, 48 hours, 7 and 28 days |

Plasma samples for determining total concentration of ticagrelor and its active metabolite, TAM (or ARC-124910XX) will be collected from subjects in Cohorts 4 through 10 before dosing (within 10 minutes prior to the initiation of the study drug infusion [Hour 0], and up to 48 hours following the initiation of study drug infusion. Specific collection times for each cohort are listed in the table below:

| Summary of Pharmacokinetic Assessments for ticagrelor and active metabolite TAM | |
| --- | --- |
| Cohorts 4-6 | −10 minutes, 0.5, 1, 2, 3, 4, 6, 12, 24, and 48 hours |
| Cohorts 7-10 | −10 minutes, 5 minutes, 0.25, 0.5, 1, 2, 3, 6, 8, 10, 12, 14, 16, 20, 24, 32, and 48 hours |

If in Cohort 9, a 6th dose of ticagrelor is administered 24 hours after the study drug infusion, additional PK samples will be collected up to 24 hours following the administration of the 6th ticagrelor dose as noted in the table below:

| Summary of Pharmacokinetic Assessments for Ticagrelor and Active Metabolite TAM AFTER a 6th dose of Ticagrelor has been given | |
| --- | --- |
| Cohort 9 | 0.5, 1, 2, 3, 6, 12, and 24 hours AFTER the administration of the $6^{th}$ dose of ticagrelor |

Plasma samples for determining unbound ticagrelor and TAM concentrations will be collected from subjects in Cohorts 4 through 10 before dosing (within 10 minutes prior to the initiation of study drug infusion [Hour 0] and up to 48 hours following the initiation of study drug infusion). Specific collection times for each cohort are listed in the table below:

| Summary of Pharmacokinetic Assessments for unbound ticagrelor and active metabolite TAM | Summary of Pharmacokinetic Assessments for Unbound Ticagrelor and TAM |
| --- | --- |
| Cohorts 4-6 | −10 minutes, 0.5, 1, 2, 3, 6, 12, 24, and 48 hours |
| Cohorts 7-10 | −10 minutes, 5 minutes, 0.25, 0.5, 1, 2, 3, 6, 8, 10, 12, 14, 16, 20, 24, 32, and 48 hours |

The Following Plasma PK Parameters for PB2452 Will be Calculated:

Area under the plasma concentration versus time curve (AUC) from time 0 to the time of the last quantifiable concentration (AUC0-t);

Observed maximum plasma concentration (Cmax);

Time to reach the observed maximum plasma concentration (Tmax);

AUC from time 0 extrapolated to infinity (AUC0-inf) (if data permit);

Terminal elimination half-life (t½) (if data permit);

Apparent clearance (CL) (if data permit);

The Following Plasma PK Parameters for Ticagrelor and TAM Will be Calculated:

Cmax;

Tmax;

AUC from time 0 to 12 hours after dosing (AUC0-12);

AUC from time 0 to 24 hours after dosing (AUC0-24);

AUC from time 0 to 48 hours after dosing (AUC0-48);

AUC from time 0 to the time of last quantifiable concentration (Clast) (AUC0-t);

AUC0-inf (if data permit);

t½ (if data permit);

For Cohorts receiving a 6th dose of ticagrelor 24 hours following study drug, PK parameters AUC0-24 and AUC 0-inf (if data permits) will only be calculated. Additional PK parameters might be included.

Pharmacodynamic Assessments:

Blood samples for PD analysis will be collected from subjects in Cohorts 4 through 10 at the following time points: before dosing (within 60 minutes prior to first ticagrelor dose on Day −2) and again before dosing (within 10 minutes prior to the initiation of the study drug] infusion [Hour 0]), and up to 48 hours after the initiation of study drug infusion. Specific collection times are listed in the table below:

| Summary of Pharmacodynamic Assessments | |
| --- | --- |
| | Pharmacodynamic |
| Cohorts 1-6 | Day −2 (60 minutes prior to first ticagrelor dose) and Day 1 (−10 minutes, 0.5, 1, 2, 3, 6, 12, 24 and 48 hours) |

-continued

Blood samples for PD analysis will be collected from subjects in Cohorts
4 through 10 at the following time points: before dosing (within 60
minutes prior to first ticagrelor dose on Day −2) and again before
dosing (within 10 minutes prior to the initiation of the study drug]
infusion [Hour 0]), and up to 48 hours after the initiation of study
drug infusion. Specific collection times are listed in the table below:
Summary of Pharmacodynamic Assessments

| | |
|---|---|
| Cohorts 7-10 | Day −2 (60 minutes prior to first ticagrelor dose) and Day 1 (−10 minutes, 5 minutes, 0.25, 0.5, 1, 2, 3, 6, 8, 10, 12, 16, 20, 24 and 48 hours) |
| | If in cohort 9 a 6th Ticagrelor dose is administered 24 hours after the infusion of study drug, additional PD samples will be collected as follows: |
| Cohort 9 | Day 2: 1, 2, 6 and 12 hours post 6th ticagrelor dose. Note: A 24 hour post-6th ticagrelor dose PD sample is equivalent to the 48 hour post-study drug sample already being collected. |

The following PD data and parameters will be generated from LTA, $P2Y_{12}$ reaction units (pRU), and platelet reactivity index (PRI) assays.

The maximal, final extent of aggregation and area under the curve for up to four platelet agonists, [(20 μM adenosine diphosphate (ADP), 5 μM adenosine diphosphate (ADP), 1.6 mM arachidonic acid (AA) and 15 μM thrombin receptor activating peptide (TRAP)] at each assessment point will be recorded.

percent of baseline platelet aggregation;
Maximal platelet aggregation;
Time to maximal platelet aggregation;
Time to 60%, 80%, 90% of baseline platelet aggregation.
VerifyNow™ $P2Y_{12}$: 1) PRU at each assessment point; 2) Percent of baseline in PRU; 3) Maximal PRU; 4) Time to maximal PRU; 5) Time to 60%, 80%, 90% of baseline PRU
VASP by ELISA: 1) PRU at each assessment point; 2) Percent of baseline in PRU; 3) Maximal PRU; 4) Time to maximal PRU; 5) Time to 60%, 80%, 90% of baseline PRU
Study Drug, Dosage, and Route of Administration:
PB2452:

All cohorts: PB2452 (concentration will vary between 0.4 mg/mL up to 72 mg/mL) single IV infusion, 250 mL to be delivered over 30 minutes to 12 hours in escalating doses of 100, 300, 1,000, 3,000, 9,000, 18,000 mg, 24,000 or 36,000 mg or intermediate doses between 9,000 to 36,000 mg. In some cases, the sponsor may elect to infuse a portion of study drug (up to 6 g) at a faster rate (equivalent to a bolus) for the first 5-20 minutes of the infusion.
Matching Placebo:

All Cohorts: 0.9% sodium chloride single IV infusion, 250 mL to be delivered at a rate matching the defined active infusion duration.
Ticagrelor:

Cohorts 4 through 10: ticagrelor 90 mg oral tablet (immediate release); administered as 180 mg (2×90 mg tablet) loading dose plus 90 mg every 12 hours for 4 additional Cohort 9: may have one additional dose administered as 180 mg ([2×90 mg) oral tablets (immediate release)] 24 hours after the initiation of the study drug infusion.

Example 2—Human Clinical Trial Data—PB2452
Reverses Ticagrelor Activity

Ticagrelor is an oral $P2Y_{12}$ inhibitor used with aspirin to reduce the risk of ischemic events in patients with acute coronary syndromes. As with other antiplatelet drugs, spontaneous major bleeding and bleeding associated with urgent invasive procedures are concerns. The antiplatelet effects of ticagrelor cannot be reversed with platelet transfusion. A rapid-acting reversal agent would be useful.

In a first-in-human randomized, double-blind, placebo-controlled, healthy volunteer study, intravenous (IV) PB2452, a monoclonal antibody fragment that binds ticagrelor with high affinity, was evaluated as a ticagrelor reversal agent. Platelet function was assessed using light transmission aggregometry (LTA), VerifyNow, and vasodilator stimulated phosphoprotein (VASP) assays before and after 48 hours of ticagrelor administration Of the sixty-four subjects randomized, 48 received PB2452 and 16 received placebo. After 48 hours of ticagrelor, platelet aggregation was suppressed by ~80%. Compared with placebo, PB2452 administered as a 10-minute intravenous bolus, followed by 16-hour infusion, significantly restored platelet function measured by multiple assays. Onset of reversal occurred within 5 minutes and was sustained for over 20 hours (P<0.0001, Bonferroni adjusted across all time points for all assays). There was no evidence of rebound in platelet activity after drug cessation. There were no drug-related adverse events.

PB2452, a specific reversal agent for ticagrelor, provided immediate and sustained reversal of ticagrelor's antiplatelet effects safely and effectively using multiple assays. PB2452 may represent a useful approach to treating or preventing ticagrelor-associated bleeding complications.
Background Antiplatelet therapy is an essential part of secondary prevention of cardiovascular events. (Bhatt (2014). In particular, dual antiplatelet therapy—the combination of aspirin with an oral $P2Y_{12}$ antagonist—is the predominant approach in patients with acute coronary syndromes, coronary artery stenting, and prior myocardial infarction. (Yusuf 92001); Mehta (2001); Bhatt (2006); Bhatt (2007); Chen (2005); Wiviott (2007); Prasugrel (2012); Wiviott (2013). The three oral P2Y12 receptor antagonists in use are clopidogrel, prasugrel, and ticagrelor. (Koski (2018)). Randomized trials have found that ticagrelor is superior to clopidogrel across the entire spectrum of acute coronary syndromes. (Wallentin (2009); Cannon (2010); James (2011).

A limitation of all three oral P2Y12 antagonists is that they increase the risk of bleeding, which persists for several days after cessation. (Plavix prescribing information; Brilinta prescribing information; Effient prescribing information). This creates challenge in patients with major bleeding, such as intracranial or gastrointestinal hemorrhage. (Ducrocq (2013); Bhatt (2007)). Additionally, patients in need of urgent and especially emergent invasive procedures are also at increased risk of periprocedural bleeding complications. If an emergent procedure is needed, the proceduralist must accept an increased bleeding risk, often after empirically providing platelet transfusions. If urgent, the operator either proceeds and anticipates increased bleeding hazard or postpones the procedure for several days with the attendant risks of delaying a clinically indicated procedure. Society guidelines recommend cessation of oral $P2Y_{12}$ receptor antagonists at least five days prior to surgery. (Capodanno (2013); Douketis (2012)).

Currently, there are no reversal agents for $P2Y_{12}$ receptor antagonists. Unlike the other $P2Y_{12}$ antagonists, ticagrelor is a reversible inhibitor. Consequently, ticagrelor will bind to $P2Y_{12}$ on transfused platelets, thereby rendering them ineffective. Therefore, a specific reversal agent for ticagrelor would be desirable.

Trial Design

This study was a single-center, randomized, double-blind, placebo-controlled, single ascending dose study to evaluate the safety, efficacy, and pharmacokinetics of PB2452 in healthy subjects 18 to 50 years of age who were or were not given ticagrelor pre-treatment. As shown in Table 1, ten sequential dose cohorts were evaluated.

TABLE 1

Final Study Design

| Cohort | Ticagrelor Pretreatment | PB2452 IV regimen | Subjects (Active:Placebo) |
|---|---|---|---|
| 1 | None | 0.1 g 30 min | 3A:1P |
| 2 | | 0.3 g 30 min | 3A:1P |
| 3 | | 1.0 g 30 min | 3A:1P |
| 4 | 180 mg PO + | 1.0 g 30 min | 6A:2P |
| 5 | 90 mg BID × | 3.0 g 30 min | 6A:2P |
| 6 | 2 days | 9.0 g 30 min | 6A:2P |
| 7 | | 18 g (3 g 5 min + 15 g hr 55 min) | 7 6A:2P |
| 8 | | 18 g (6 g 15 min + 6 g hr + 6 g 8 hr 45 min) | 3 6A:2P |
| 9 | | 18 g (6 g 15 min + 6 g hr + 6 g 12 hr) | 4 3A:1P |
| 10 | | 18 g (6 g 10 min + 6 g hr + 6 g 13 hr) | 3 6A:2P | g = grams
A = active
P = placebo
Abbreviations: BID, twice daily

Cohorts 1-3 each enrolled 4 subjects and assessed intravenous doses of 0.1, 0.3, and 1.0 grams of PB2452 infused for 30 minutes in the absence of ticagrelor pre-treatment.

Subjects in Cohorts 4 to 10 were pre-treated with a 180 mg oral ticagrelor loading dose followed by 90 mg twice daily for 48 hours prior to evaluation of PB2452 at doses of 1.0 to 18 grams. Cohorts 4, 5, and 6 each consisted of 8 subjects randomly assigned to receive 1.0, 3.0, and 9.0 grams of PB2452 or placebo after ticagrelor pretreatment. Cohorts 7 to 10 received an 18-gram fixed dose of PB2452 via various infusion regimens or placebo. Infusions of PB2452 in these cohorts were initiated 2 hours after the last ticagrelor pretreatment dose to coincide with the peak concentration of ticagrelor. (Gurbel (2009). Subjects in all cohorts were randomized in a 3:1 ratio to receive PB2452 or placebo.

Subject Eligibility: Eligible subjects were healthy males and female 18 to 50 years of age with a body mass index between 18 and 35 kg/m$^2$ and weight from ≥50 kg to ≤120 kg. Subjects with any contraindication to ticagrelor, medical history suggestive of an increased risk of bleeding, or estimated glomerular filtration rate below 60 mL/min/1.73 m$^2$ were excluded. Written informed consent was obtained from all subjects.

Outcomes

The primary efficacy outcome was the effectiveness of PB2452 in reversing the antiplatelet effect of ticagrelor by analyzing platelet aggregation using light transmission aggregometry at multiple time points before and after PB2452 or placebo administration in ticagrelor pretreated subjects. Secondary efficacy outcomes were the effectiveness of ticagrelor reversal assessed using VerifyNow and the vasodilator stimulated phosphoprotein phosphorylation immunoassay (VASP).

The primary safety outcome was the frequency and severity of treatment emergent adverse events (AEs) associated with PB2452 with or without oral ticagrelor pretreatment.

Clinical laboratory test results, vital sign measurements, 12-lead ECG and continuous telemetry results, and physical examination findings were also assessed at multiple timepoints from screening to the end of the 28-day safety follow-up period. Immunogenicity was assessed before and at 7 and 28 days after PB2452 administration.

Other secondary outcomes included assessment of the PB2452 and ticagrelor pharmacokinetic profiles and evaluation of PB2452 immunogenicity at day 7 and 28 post-infusion.

Statistical Analysis

The sample size of 64 was based on clinical and practical considerations and not on a formal statistical power calculation. The sample size was considered sufficient to adequately assess the safety, efficacy, and pharmacokinetic profiles of PB2452 and the pharmacokinetic and pharmacodynamic profiles of ticagrelor. Reversal of antiplatelet effect was evaluated by comparing the mean percent of baseline platelet aggregation between PB2452 and placebo using Wilcoxon rank-sum test. Multiplicity was adjusted using the Bonferroni method. Correlations between each pair of the platelet function tests were evaluated using Pearson's correlation and Spearman's rank correlation coefficient. Mean data from subjects receiving placebo were pooled across cohorts for all presentations. Categorical variables are summarized by their frequencies and percentages, and continuous variables are presented with the number of subjects with non-missing data, mean, standard deviation, median, minimum, and maximum. Descriptive statistics are presented for each cohort, and pooled placebo and PB2452 data. For pharmacodynamic data, platelet aggregation results were compared between each cohort and pooled placebo data (cohorts 4 to 6 and cohort 7 to 10 were pooled separately). All analyses were performed with SAS software, version 9.4 (SAS Institute).

Results

Figure 6B:
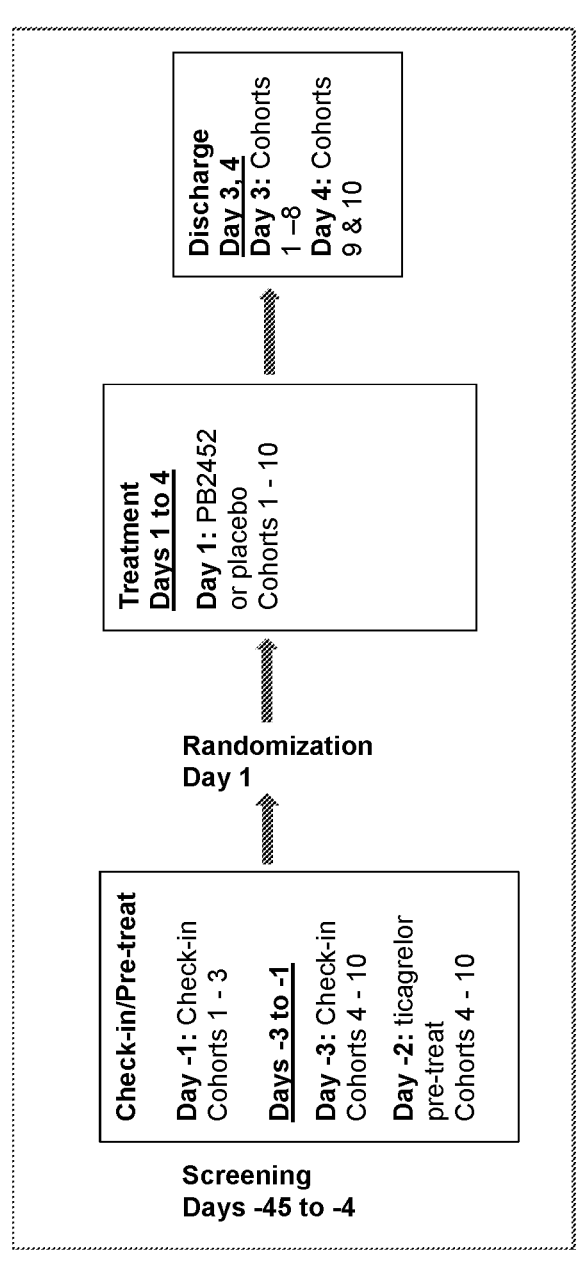

Study Population: A total of 64 subjects were randomized. Of these, 48 received PB2452 and 16 received placebo. Of the 48 receiving PB2452, 21 received the highest dose of 18 grams and 39 received ticagrelor pretreatment. Final study design and subject flow diagrams are shown in Table 1 and FIG. 6, respectively. Baseline characteristics of the subjects are provided in Table 2.

TABLE 2

Baseline Characteristics

| | All Placebo (N = 16) | All MEDI2452 (PB2452) (N = 48) |
|---|---|---|
| Age (years), Mean (min-max) | 34.0 (8.26) | 30.5 (8.76) |
| Sex, n (%) | | |
| Male | 11 (68.8) | 23 (47.9) |
| Female | 5 (31.3) | 25 (52.1) |
| Weight (kg), Mean (SD) | 86.2 (13.5) | 78.2 (14.8) |
| Height (cm), Mean (SD) | 173.3 (6.4) | 167.8 (10.2) |
| BMI (kg/m$^2$), Mean (SD) | 28.6 (3.3) | 27.7 (4.1) |
| Ethnicity, n (%) | | |
| Hispanic or Latino | 6 (37.5) | 22 (45.8) |
| Not Hispanic or Latino | 10 (62.5) | 26 (54.2) |
| Race, n (%) | | |
| White | 7 (43.8) | 27 (56.3) |
| Black or African American | 8 (50.0) | 18 (37.5) |
| Asian | 0 | 1 (2.1) |
| American Indian or Alaska Native | 1 (6.3) | 0 |

TABLE 2-continued

| | | |
|---|---|---|
| Baseline Characteristics | | |
| | All Placebo (N = 16) | All MEDI2452 (PB2452) (N = 48) |
| Native Hawaiian or Other Pacific Islander | 0 | 1 (2.1) |
| Multiple | 0 | 1 (2.1) |
| Platelet count, Mean (SD) (×1000/uL) | 239 (52.1) | 253 (46.8) |
| LTA Platelet aggregation, Mean (SD) (%) | 82.1 (7.53) | 82.9 (7.49) |
| VerifyNow P2Y12 PRU, Mean (SD) | 226.4 (39.9) | 237.7 (36.8) |
| VASP ELISA PRI, Mean (SD) | 89.8 (4.17) | 90.2 (3.64) |

Safety: Overall PB2452 was considered safe and well-tolerated. A total of 30 treatment-emergent adverse events were reported in 19 of the 64 subjects (29.7%). Of the 48 subjects given PB2452, 17 (35.4%) reported 27 adverse events, whereas 2 of the 16 subjects given placebo (12.5%) reported 3 adverse events (Table 3). None of the adverse events was considered related to study drug. There were no study-drug related serious adverse events, dose-limiting toxicities, or infusion-related reactions. There were no deaths or adverse events leading to study drug discontinuation. One subject experienced 2 serious adverse events (alcohol poisoning and acute respiratory failure) after discharge from the clinical site both of which were considered unrelated to study drug. With the exception of 1 subject in Cohort 3, all subjects with adverse events had received ticagrelor pretreatment. Changes in mean clinical laboratory results, vital sign measurements, and ECG values were similar across treatment groups and when compared with placebo.

TABLE 3

| | | | |
|---|---|---|---|
| Treatment-emergent Adverse Events, Safety Population | | | |
| Preferred Term | All Placebo (N = 16) n (%) | All PB2452 (N = 48) n (%) | All Subjects (N = 64) n (%) |
| Total Number of TEAEs | 3 | 27 | 30 |
| Number of Subjects with at Least 1 TEAE | 2 (12.5) | 17 (35.4) | 19 (29.7) |
| Infusion site bruising | 0 | 4 (8.3) | 4 (6.3) |
| Medical device site reaction | 0 | 3 (6.3) | 3 (4.7) |
| Infusion site extravasation | 0 | 2 (4.2) | 2 (3.1) |
| Vessel puncture site bruise | 0 | 2 (4.2) | 2 (3.1) |
| Abdominal pain | 0 | 1 (2.1) | 1 (1.6) |
| Acute respiratory failure | 0 | 1 (2.1) | 1 (1.6) |
| Alcohol poisoning | 0 | 1 (2.1) | 1 (1.6) |
| Blood urine present | 0 | 1 (2.1) | 1 (1.6) |
| Conjunctivitis | 0 | 1 (2.1) | 1 (1.6) |
| Contusion | 1 (6.3) | 0 | 1 (1.6) |
| Dizziness | 0 | 1 (2.1) | 1 (1.6) |
| Eyelid irritation | 1 (6.3) | 0 | 1 (1.6) |
| Gastroenteritis | 0 | 1 (2.1) | 1 (1.6) |
| Hematuria | 0 | 1 (2.1) | 1 (1.6) |
| Infusion site reaction | 0 | 1 (2.1) | 1 (1.6) |
| Musculoskeletal chest pain | 1 (6.3) | 0 | 1 (1.6) |
| Nasopharyngitis | 0 | 1 (2.1) | 1 (1.6) |
| Oropharyngeal pain | 0 | 1 (2.1) | 1 (1.6) |

TABLE 3-continued

| | | | |
|---|---|---|---|
| Treatment-emergent Adverse Events, Safety Population | | | |
| Preferred Term | All Placebo (N = 16) n (%) | All PB2452 (N = 48) n (%) | All Subjects (N = 64) n (%) |
| Pharyngitis streptococcal | 0 | 1 (2.1) | 1 (1.6) |
| Pneumonia aspiration | 0 | 1 (2.1) | 1 (1.6) |
| Skin abrasion | 0 | 1 (2.1) | 1 (1.6) |
| Upper limb fracture | 0 | 1 (2.1) | 1 (1.6) |

Note:
A treatment-emergent AE (TEAE) is defined as any event not present before exposure to study drug or any event already present that worsens in intensity or frequency after the exposure. For analysis purposes, TEAEs are the events with onset on or after initiation of study drug. At each level of subject summarization, a subject is counted once if the subject reported 1 or more events. Percentages are based on the number of subjects in the safety population for each treatment group and overall. Adverse events are coded using MedDRA version 21.0.

Reversal of Ticagrelor

Figure 2:
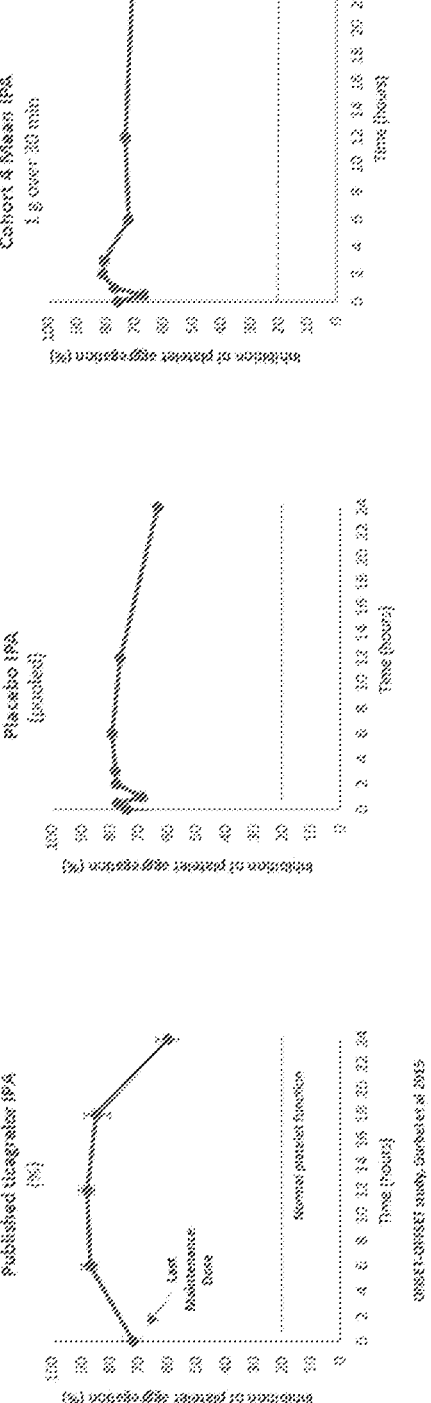
FIG. 2 shows mean inhibition of platelet aggregation (IPA) in Cohort 4. Administration of 1 g PB2452 intravenously does not reverse ticagrelor action.
Figure 4:
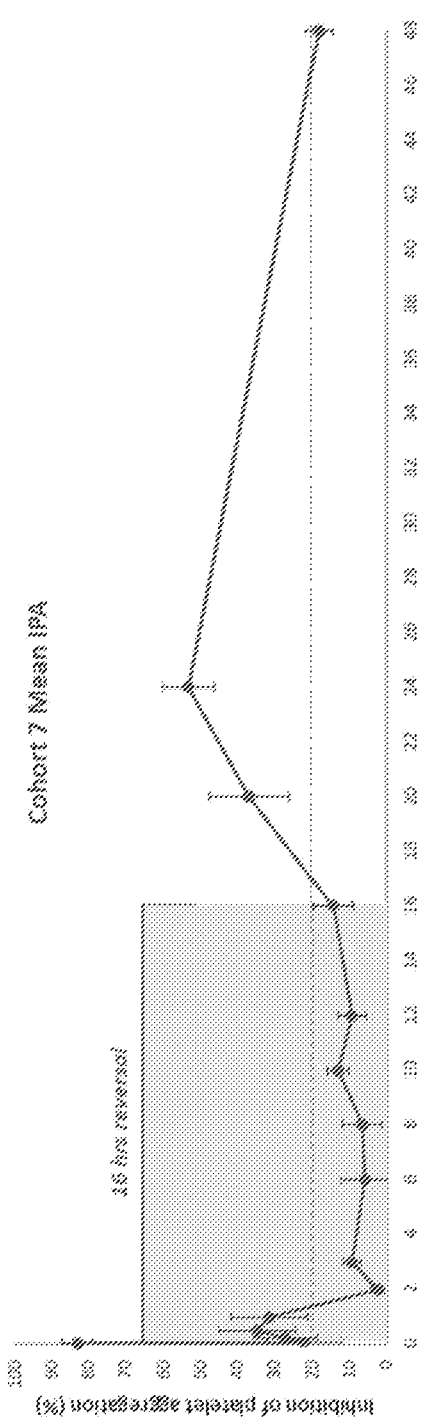
FIG. 4 shows inhibition of platelet aggregation (IPA) in Cohort 7. Administration of PB2452 causes ticagrelor reversal for 16 hours.
Figure 5:
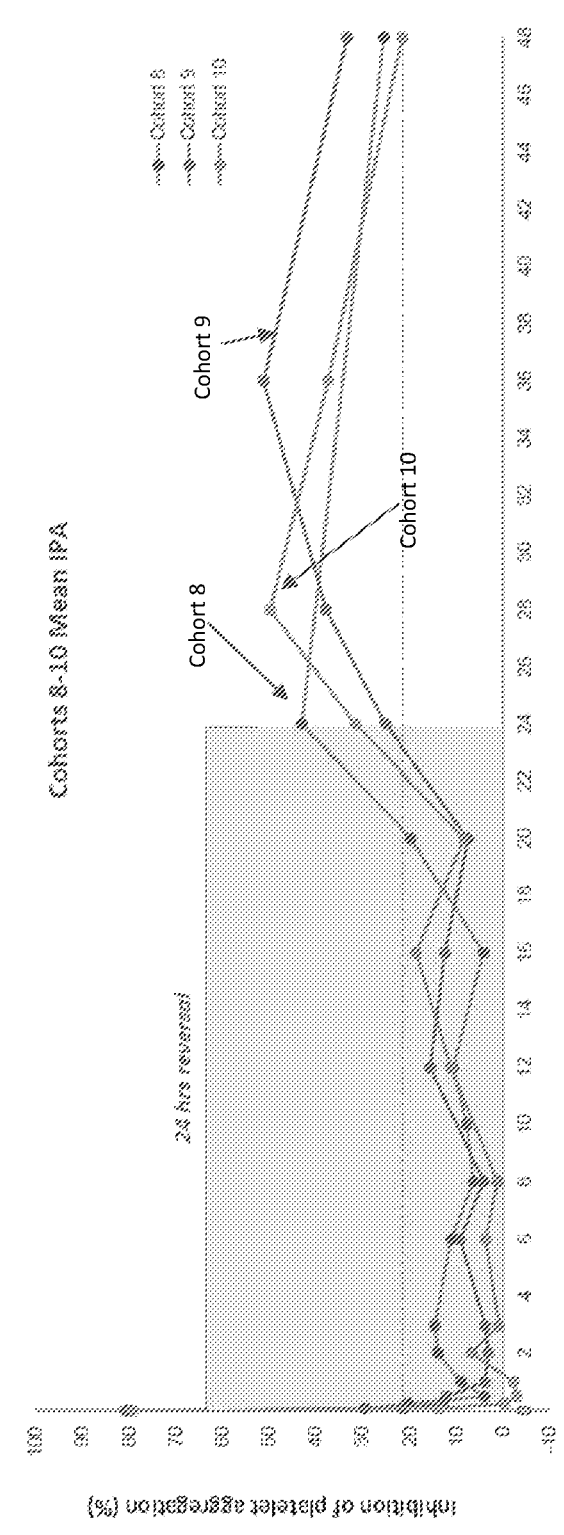
FIG. 5 shows inhibition of platelet aggregation (IPA) in Cohorts 8, 9, and 10. Administration of PB2452 causes ticagrelor reversal for about 24 hours.
Figure 7A:
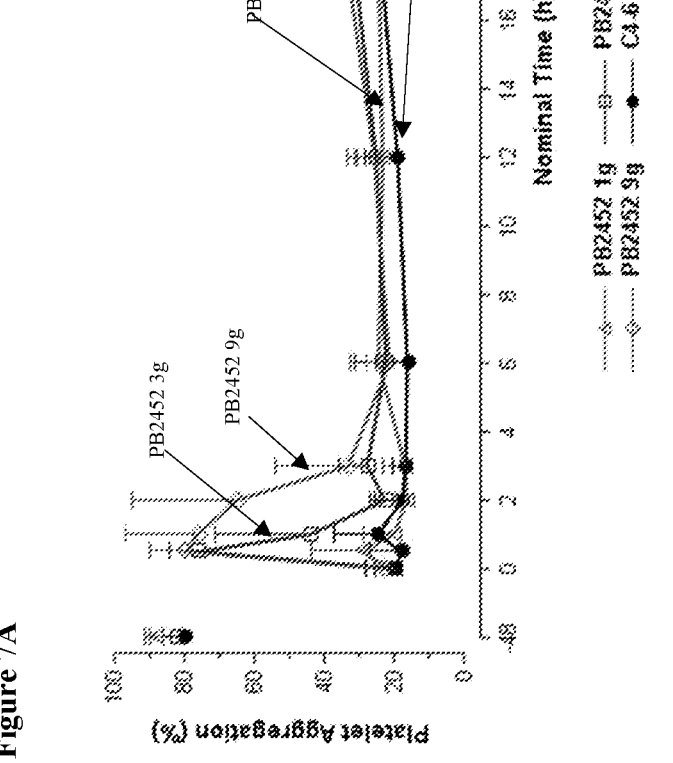
FIGS. 7A-B show the onset and duration of ticagrelor reversal. Shown is the observed increase in platelet aggregation measured by LTA in the PB2452 and placebo groups (Cohorts 4-6) administered ascending doses of PB2452 intravenously for 30 minutes (A). Subjects in Cohorts 7-10 were administered fixed 18 g doses of PB2452 with infusion durations of 8, 12, and 16 hours in Cohorts 7, 8, and 9/10, respectively (B). The −48 hr timepoint shows platelet aggregation prior to administration of ticagrelor.
Figure 7B:
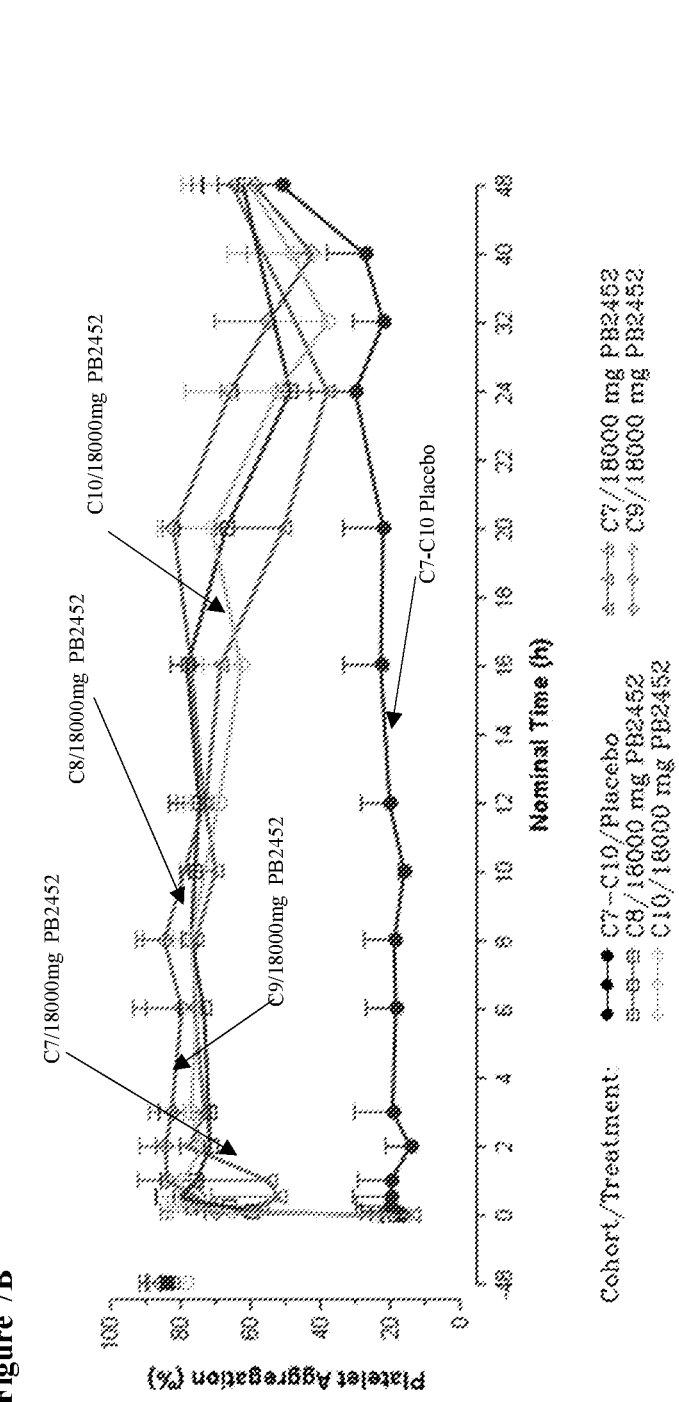

Ticagrelor reversal was assessed in Cohorts 4 to 10. Subjects were pretreated with ticagrelor for 48 hours prior to receiving PB2452 or placebo. In those receiving placebo, platelet aggregation was suppressed by 80-85% after 48 hours of ticagrelor pretreatment and remained suppressed for an additional 24 hours after ticagrelor was stopped. Platelet function gradually increased between 24 and 48 hours (FIGS. 3-5; FIGS. 7A and 7B), and no reversal was observed with administration of 1 g of PB2452 (FIG. 2). With PB2452, the first significant reversal of ticagrelor was observed at the 3.0 and 9.0 gram dose levels in Cohorts 5 and 6, respectively (FIGS. 7A and 7B). Significant but transient increases in mean platelet aggregation were observed at 30 minutes, the first time point immediately after completion of the 30 minute infusion. Duration of reversal was dose-dependent and lasted 1 to 3 hours (FIG. 7A).

To achieve more rapid and sustained reversal, the total PB2452 dose was increased to 18 grams in Cohorts 7 to 10 to accommodate an initial bolus of PB2452 and longer infusions of 8, 12, or 16 hours. In Cohort 7, a 3.0 gram bolus of PB2452 followed by an 8 hour infusion significantly increased mean platelet aggregation by 2 hours with a duration of approximately 12 hours (FIG. 7B). In Cohorts 8 to 10, the bolus was increased to 6.0 grams followed by infusions for 12 or 16 hours. With the larger bolus, reversal was achieved within 5 minutes of initiation of the infusion and was sustained for 16 to 24 hours (FIG. 7B).

Figure 8A:
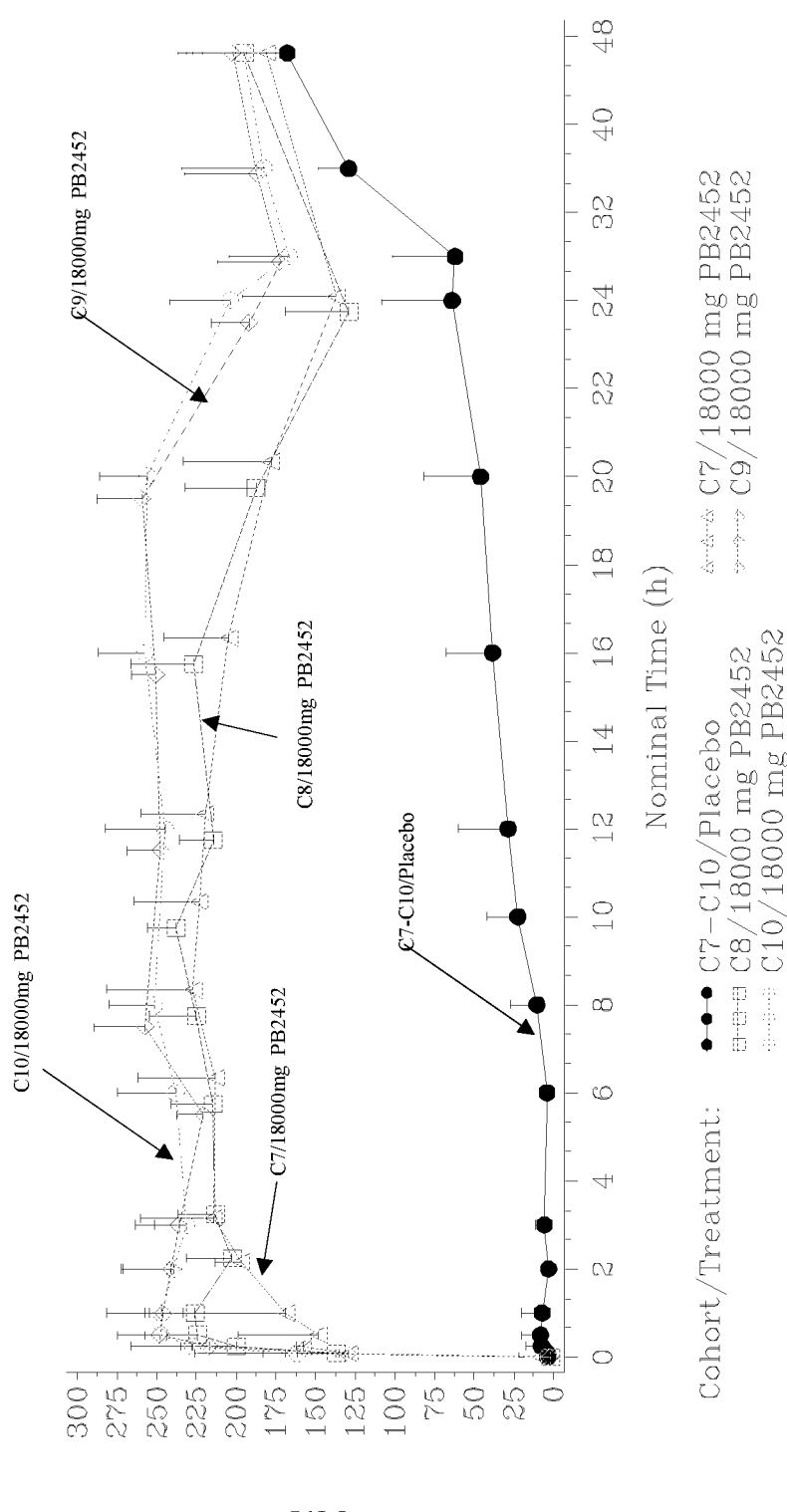
FIGS. 8A-B show the onset and duration of ticagrelor reversal by VerifyNow and VASP ELISA. Shown are mean platelet function analyses for Cohort 7-10 subjects treated with PB2452 (open markers) or placebo (solid circles) measured at multiple timepoints pre- and post-PB2452 (or placebo) infusion. Time 0 represents mean platelet function after 48 hr pretreatment with ticagrelor, but prior to PB2452 infusion. Mean platelet aggregation (PRU) measured by VerifyNow is shown in (A). Mean VASP ELISA PRI is shown in (B).
Figure 8B:
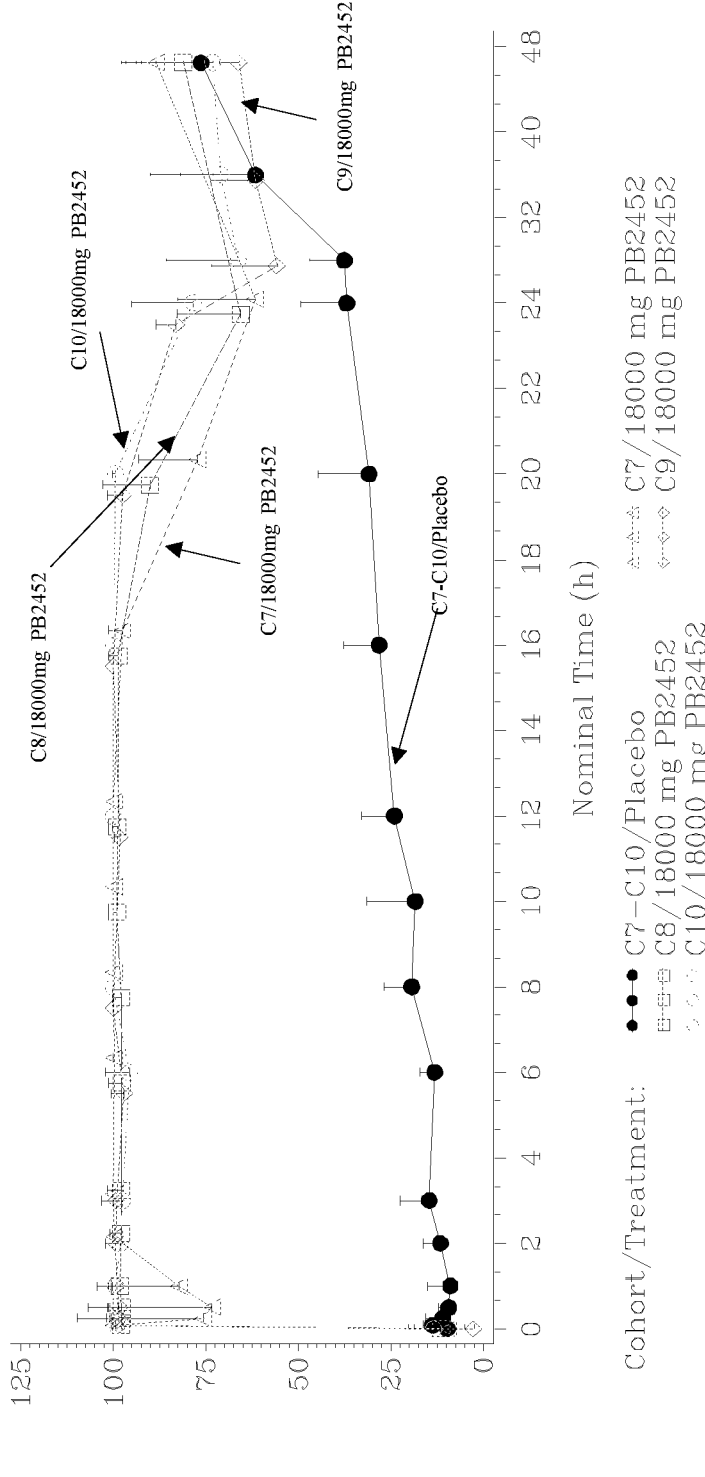
Figure 9A:
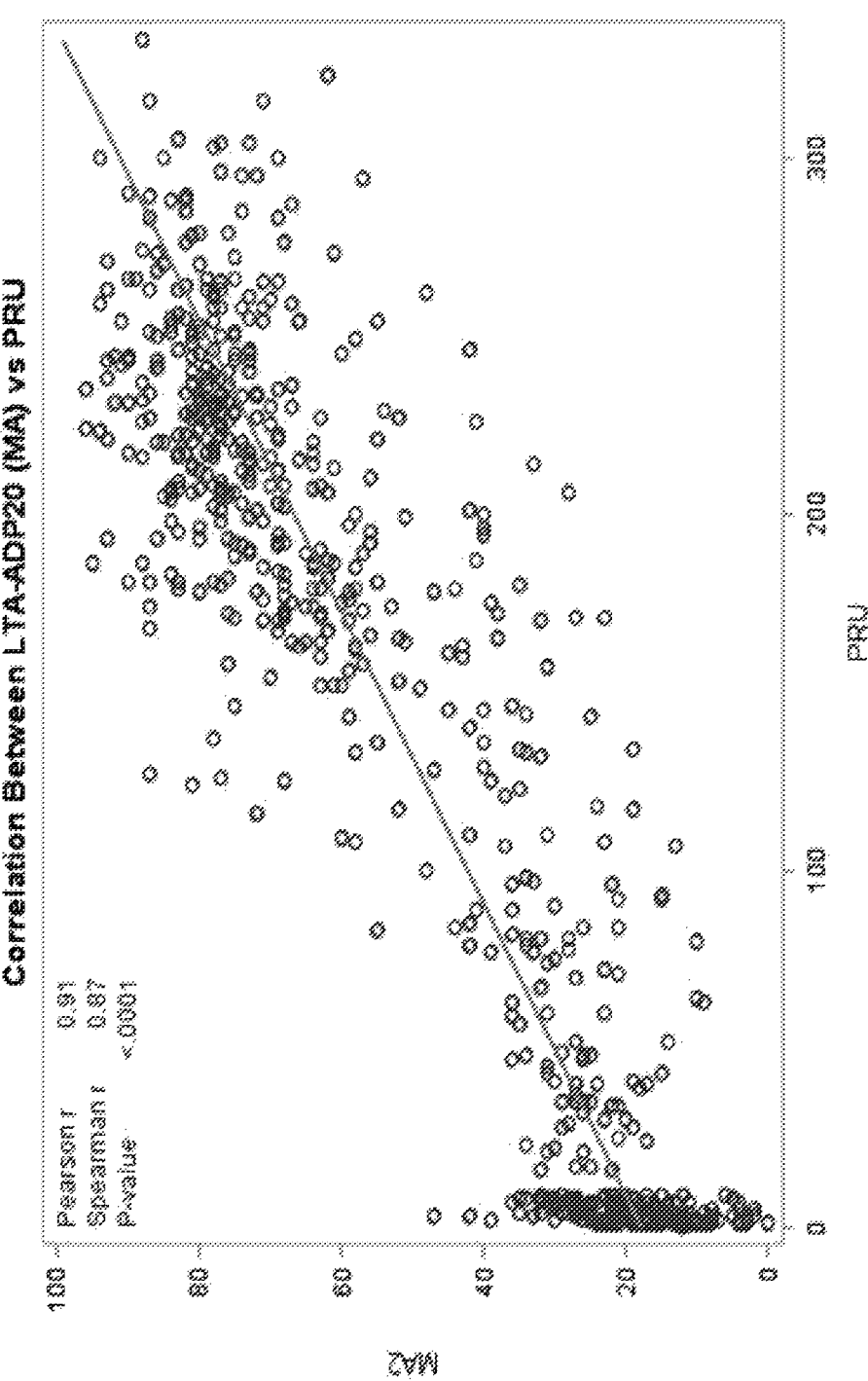
FIGS. 9A-C show correlation analyses between platelet function assays measured by LTA, VerifyNow, and VASP ELISA. Pearson and Spearman correlation analyses were performed between LTA measured aggregation and Veri-
Figure 9B:
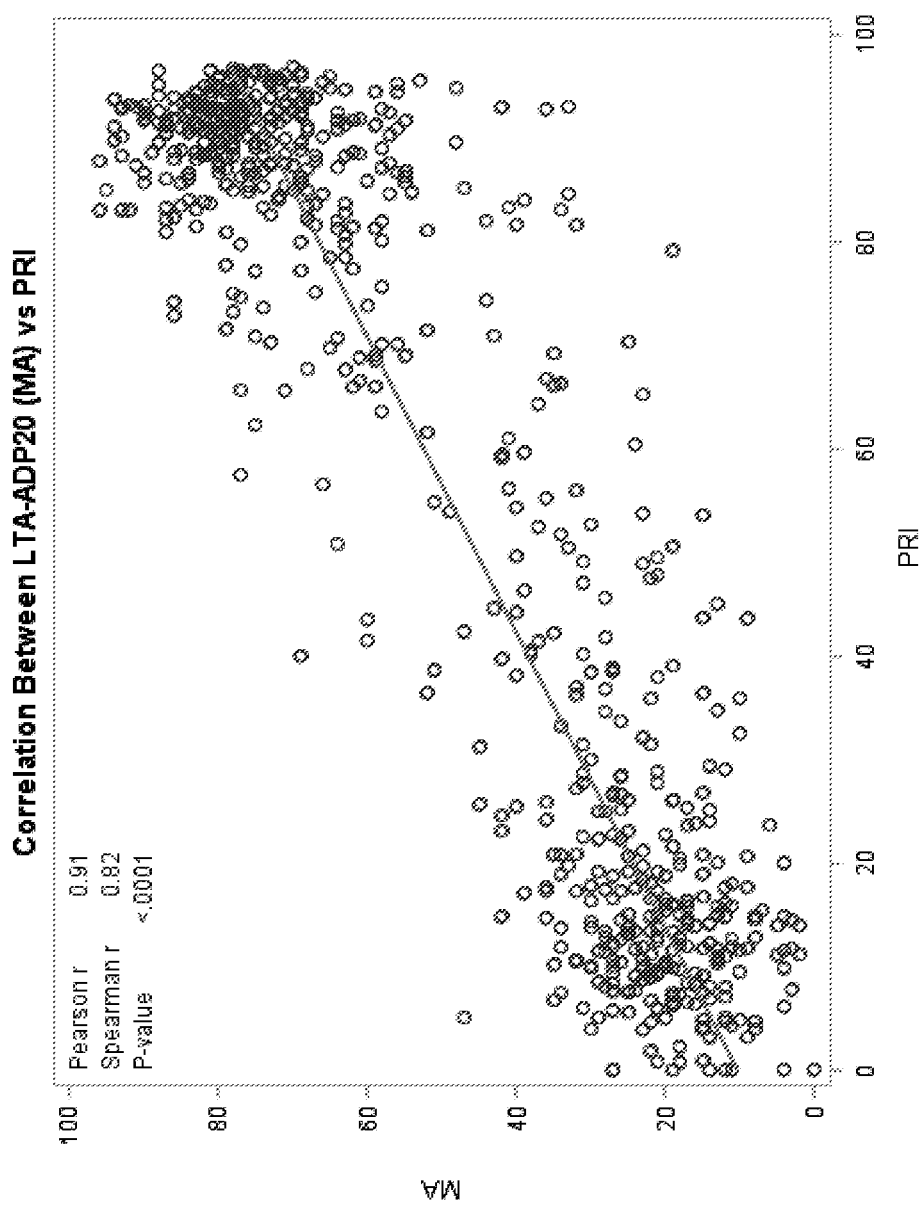
Figure 9C:
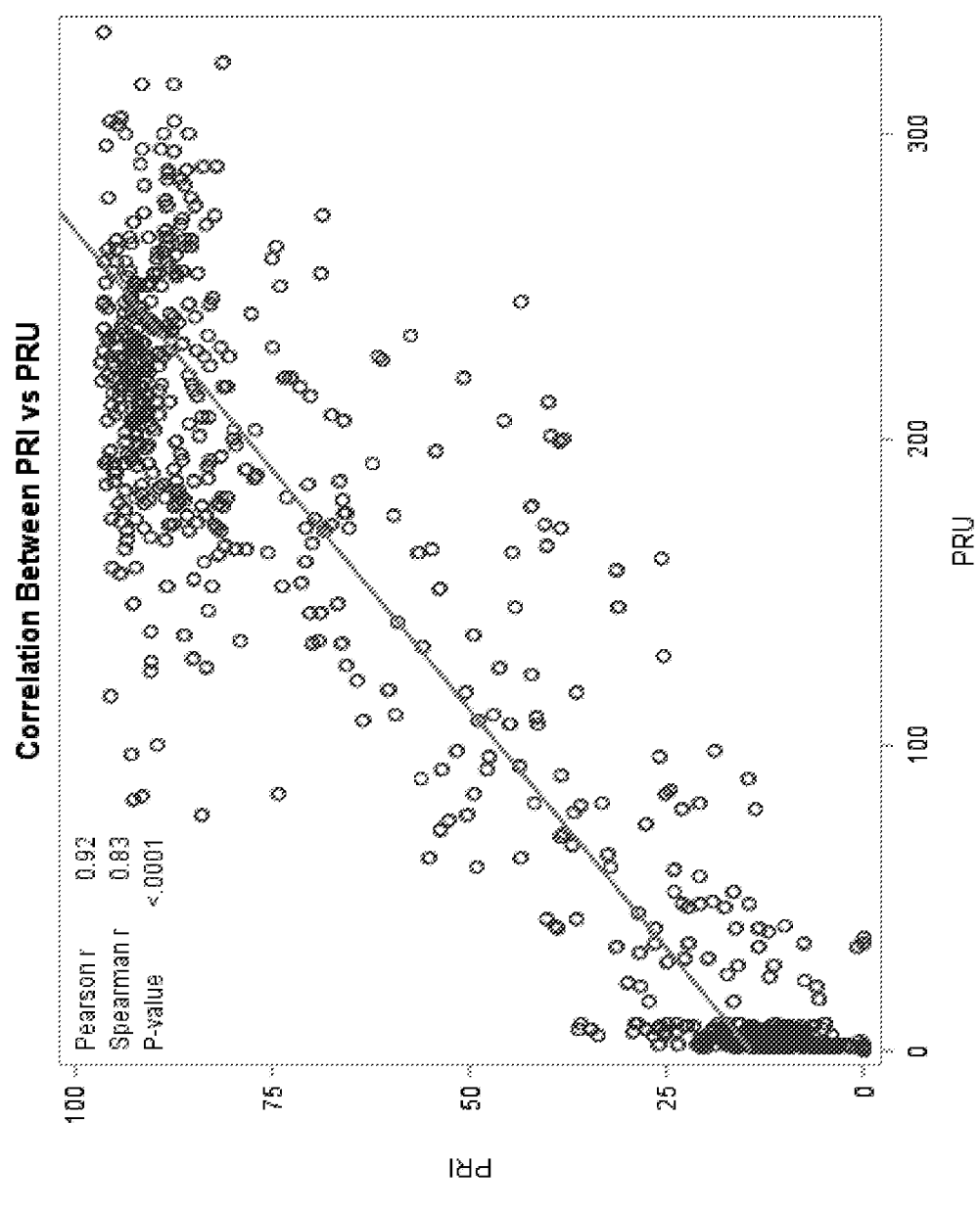

The statistically significant immediate and sustained reversal measured using the primary efficacy assessment of aggregometry was confirmed with VerifyNow and VASP (FIGS. 8A and 8B). Correlation analyses between each of the three platelet function test results demonstrated highly significant correlation for all comparisons with r values ≥0.81 and >0.91 for Pearson's and Spearman's analyses, respectively (P<0.0001 for all comparisons, FIG. 9).

To assess the extent to which normal platelet function was restored, post-PB2452 platelet function was compared with pre-ticagrelor baseline platelet function using all three assays. PB2452 restored mean platelet aggregation to within 80% of baseline at all post-treatment time points up to 20 hours (FIG. 10A). Mean VerifyNow platelet reactivity revealed rapid and sustained normalization of platelet function with PRU≥180 for 24 hours (FIG. 10B). When restoration of P2Y12 receptor signaling was assessed with VASP, PRI was restored to nearly 100% of baseline within 5 minutes and sustained for 20-24 hours (FIG. 10C).

To determine whether acute ticagrelor reversal causes a potentially prothrombotic rebound increase in platelet aggregation, platelet aggregation in response to a low concentration of ADP was determined (5 µM instead of the usual 20 µM). Additionally, platelet aggregation in response to other agonists including arachidonic acid and thrombin receptor activating peptide was also tested. As expected, 5 µM ADP elicited a lower response than 20 µM ADP (FIGS. 12A and 12B), and the responses to arachidonic acid and thrombin receptor activating peptide after reversal were similar to baseline before ticagrelor or PB2425 administration (data not shown).

Pharmacokinetics

Figure 11A:
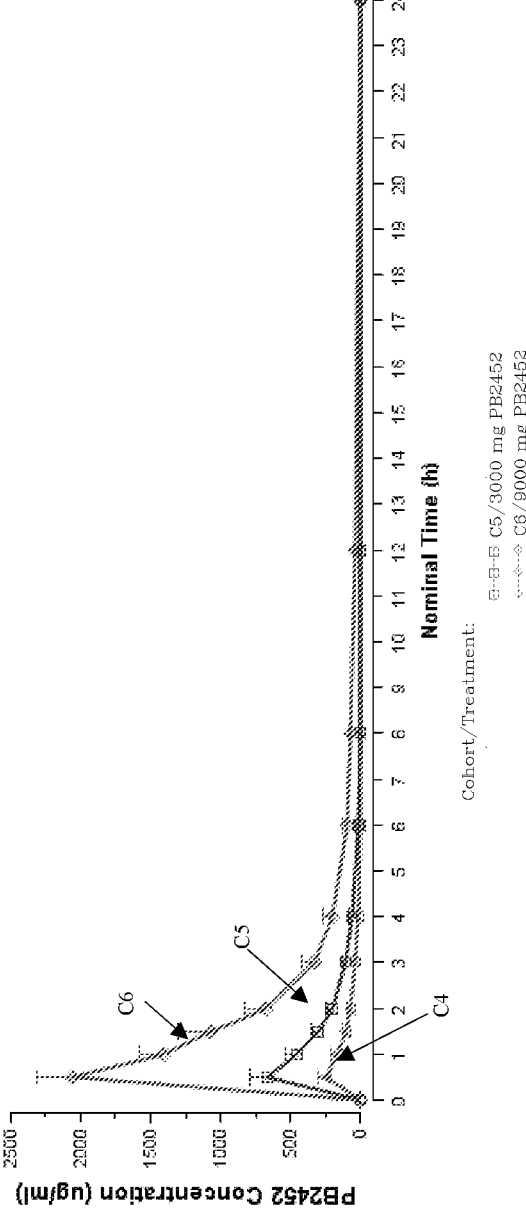
Figure 11B:
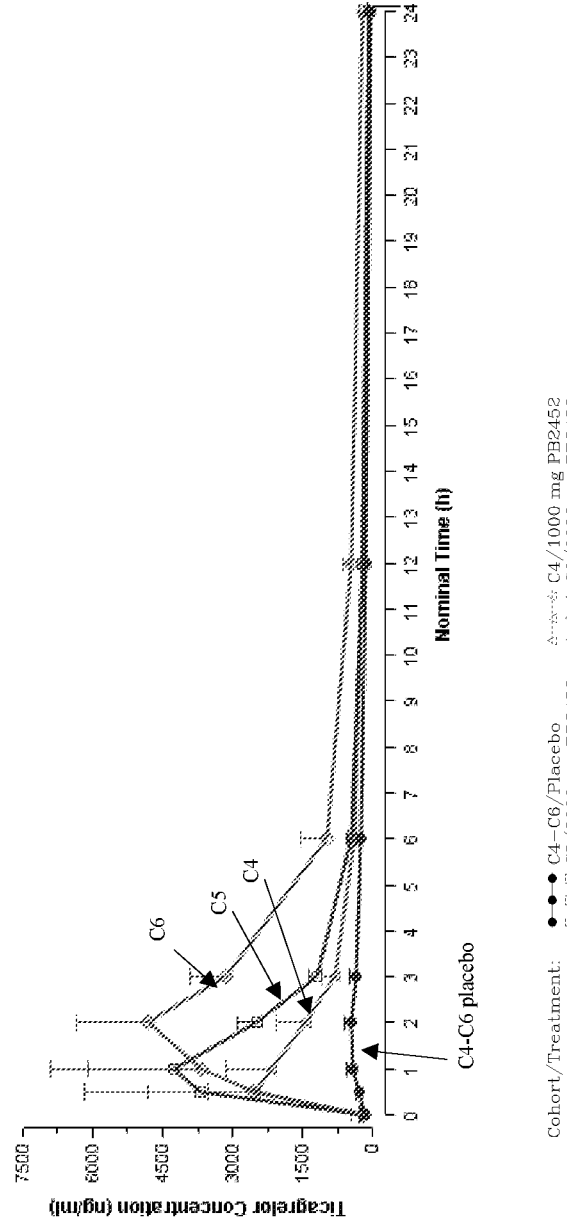
Figure 11C:
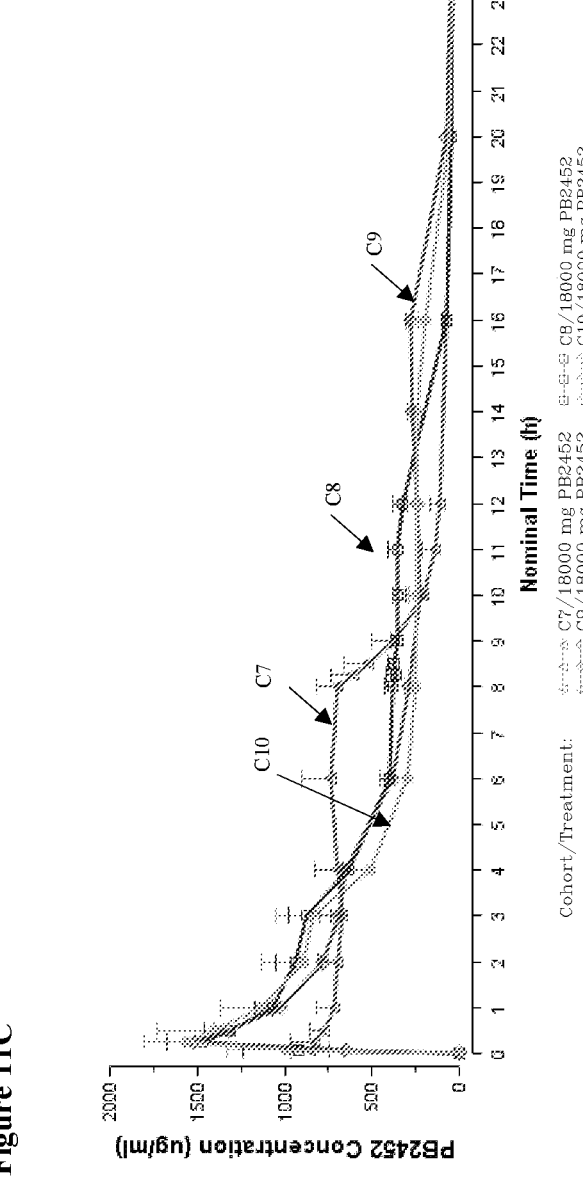
Figure 11D:
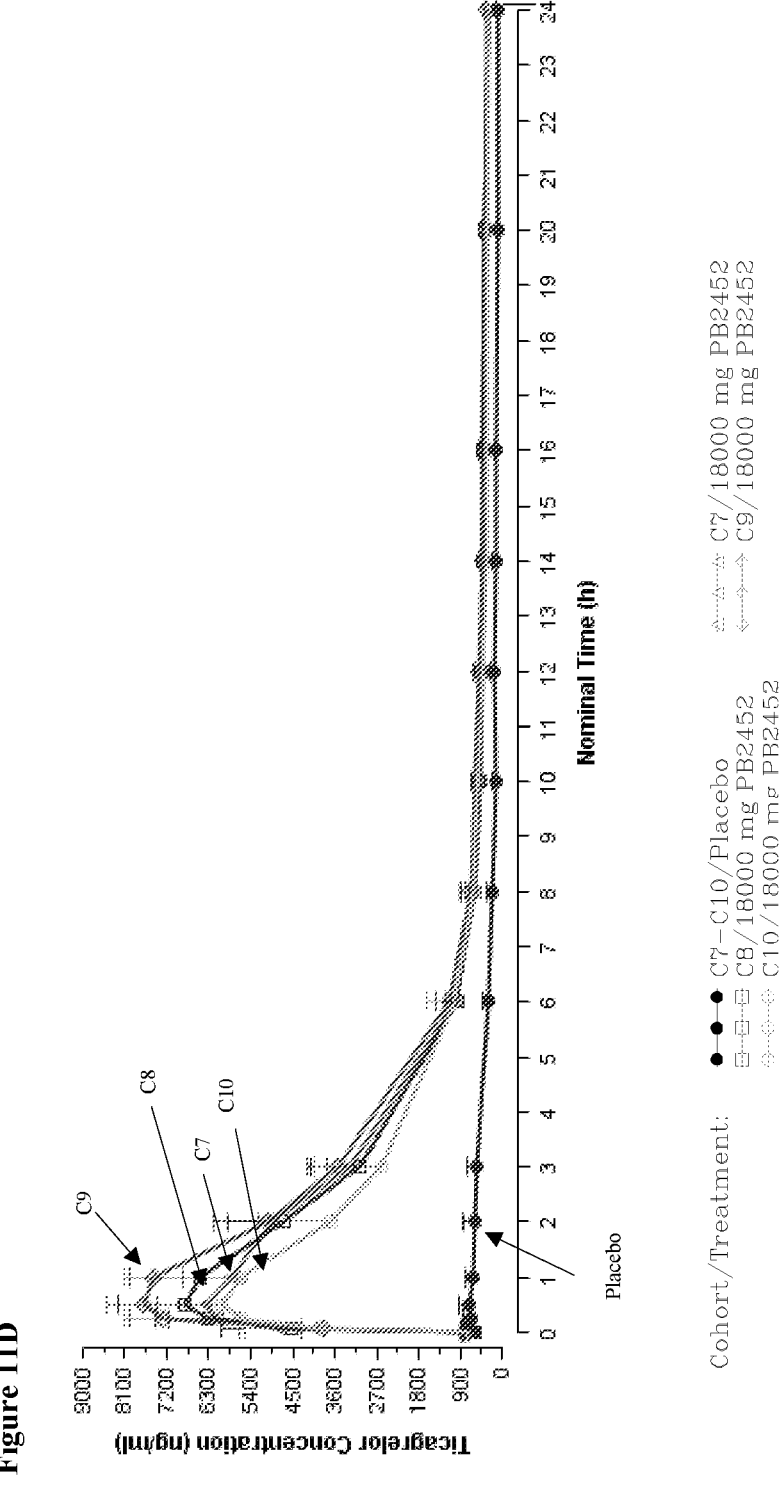

Pharmacokinetic analysis of PB2425 demonstrated dose-linear increases in mean exposure across the dose range of 0.1 to 9.0 grams (FIG. 11A). The estimated distribution half-life and terminal half-life were 0.86 hours and 6.9 hours, respectively, with an estimated clearance of 1.88 L/min and a volume of distribution of approximately 2.9 L, suggesting PB2452 confinement to the vascular compartment. In subjects receiving ticagrelor alone, total ticagrelor concentrations peaked at 900 ng/mL approximately 2 hours after an oral dose. In the presence of PB2452, the mean concentration of circulating ticagrelor increased by approximately 2-5.6-fold (FIG. 11B). At the 18 gram dose level with 8- to 16-hour infusions, PB2452 exposure was extended for 12-24 hours (FIG. 11C), and mean ticagrelor concentrations increased by 5.6 fold compared with those in subjects given ticagrelor alone (FIG. 11D). These increases in ticagrelor exposure appeared to be dependent on PB2452 dose and likely reflect tight binding between PB2452 and ticagrelor and the subsequent redistribution of extra-vascular ticagrelor into the vascular compartment.

Immunogenicity

Of the 48 subjects given PB2452, 21 (43.8%) had detectable anti-drug antibodies, of whom 15 (31.3%) had pre-existing (pre-dose) antibodies and 6 (12.5%) were positive post-dosing, albeit with low titers of 40 (n=5) or 160 (n=1). In subjects assigned to placebo, 3 of 16 (18.8%) tested positive, with 2 having pre-existing antibodies. All antibody titers were low and had no observed effect on PB2452 safety or efficacy.

Discussion

This study demonstrated that intravenous infusion of the monoclonal antibody fragment PB2452 significantly reversed the antiplatelet effects of ticagrelor as measured using multiple sensitive assays of platelet function. Within the healthy population studied, there were no serious adverse events or infusion reactions associated with PB2452. Therefore, PB2452 represents an effective means to reverse ticagrelor's antiplatelet effect in patients with bleeding or in urgent need of hemostasis during invasive procedures.

The ability to reverse the action of the novel oral anticoagulants has been a major advance in anti-thrombotic therapy. Currently, there is no effective way to reverse the antiplatelet effects of oral $P2Y_{12}$ antagonists such as ticagrelor, other than to hold the drug and wait 3 to 5 days for its effects to dissipate, which is problematic in patients with life-threatening bleeding or at high risk of thrombosis. Treatment guidelines and ticagrelor prescribing information state to wait at least 5 days prior to surgical procedures. Waiting this long is impossible in patients who need emergent surgery and may be inadvisable in a patient needing urgent surgery. Unfortunately, platelet transfusion is not useful for patients taking ticagrelor because the drug will bind to the fresh platelets. (Godier (2015); Teng (2016)). Therefore, there is a need for a ticagrelor reversal agent.

PB2452 is a recombinant human IgG1 monoclonal antibody antigen-binding fragment that binds with high specificity to ticagrelor its active metabolite AR-C124910XX. (Buchanan (2015)). With its high affinity, PB2452 can neutralize free ticagrelor and drug bound to the P2Y12 receptor, which without being bound by theory, explains the observed rapid reversal with PB2452. The mechanism of action is specific to ticagrelor only and will not work on clopidogrel or prasugrel, which are irreversible P2Y12 receptor antagonists, nor is any other off-target binding be anticipated.

CONCLUSION

Intravenous PB2452 reverses the antiplatelet effects of ticagrelor. Administration of PB2452 may be a useful strategy for ticagrelor reversal in patients with serious bleeding or requiring urgent surgery or other invasive procedures.

Example 3—Study to Evaluate the Safety, Tolerability, PK and PD of PB2452 in Older and Elderly Subjects Pre-Dosed with Ticagrelor and Acetylsalicylic Acid The safety, tolerability, pharmacokinetics and pharmacodynamics of PB2452 will be compared to matching placebo, in older and elderly patients with ticagrelor and acetylsalicylic acid (ASA) pretreatment in a Phase 2A, randomized, double-blind, placebo-controlled, single dose, sequential group study. Various dose levels and administration regiments will be administered to older (ages 50 to 64 years) and elderly (ages 65 to 80 years) male and female subjects.

Up to 5 dose levels and/or administration regimens will be evaluated in up to 5 cohorts. Each cohort will include 8 to 12 subjects randomized in a 3:1 ratio (PB2452:placebo).

The initial cohort (Cohort 1) will include approximately 8 subjects ages 50 to 64 years pretreated with ASA+ticagrelor who will be randomized to receive 18 grams (g) of PB2452 or matching placebo administered as an initial 6 g bolus infused over 10 minutes, followed by 12 g infused over the next 15 hours and 50 minutes to complete a 16 hour regimen. This initial regimen was shown to be safe and well tolerated in healthy young adults (18 to 50 years) in a prior Phase 1 study, and provided immediate and sustained reversal of the antiplatelet effects of ticagrelor.

Following completion of Cohort 1, subsequent cohorts may test the same, higher or lower dose levels, and/or different infusion regimens of PB2452 or matching placebo in the same population as in Cohort 1, or in different populations such as elderly subjects (65 to 80 years old).

The study will consist of a Screening period (Days −45 to −4), a Check-in day (Day −3) and Pretreatment Period, an on-site Randomization/Treatment day (Day 1), 3 days on-site for treatment and safety monitoring, a Follow-up Visit (Day 7), and a Final Follow-up visit (Day 28 [±2 days]). Seven days prior to Randomization (Day −7), subjects will be administered 81 mg ASA orally once daily (QD) until the final dose on the morning of Day 1 before receiving study drug. A ticagrelor 180 mg oral loading dose will be administered on the morning of Day −2 followed by 90 mg every 12 hours until the 5th dose has been administered on the morning of Day 1. A 6th dose of ticagrelor may be administered 24 hours after the initiation of study drug in a subsequent cohort.

In the morning on Day −2, subjects will begin pretreatment with ticagrelor as described in the preceding paragraph. On Day 1, subjects will be randomized in a ratio 3:1 (PB2452:placebo), to receive an IV dose of PB2452 or placebo 2 hours following the 5th ticagrelor dose. Subjects may be discharged from the clinical site between Days 3 and 7 inclusive and will return for a Follow-up visit on Day 7, if already discharged, and on Day 28 (±2 days).

Study Drug, Dosage, and Route of Administration:

PB2452: PB2452 IV infusion will be administered on Day 1 for up to 48 hours. The total dose for each subject will not exceed 30 g. The infusion rate will not exceed 18 g over 30 minutes and the concentration will not exceed 24 g in 250 mL. Subjects will not receive more than 250 mL of study drug infusion within any 1-hour period.

Matching Placebo: 0.9% sodium chloride single IV infusion, to be delivered at a rate and volume matching the active infusion.

Ticagrelor: Ticagrelor 90 mg oral tablet (immediate release) will be administered as a 180 mg (2×90 mg tablets) loading dose plus 90 mg every 12 hours for 4 additional doses. In one or more subsequent cohorts following cohort 1, subjects may also receive an additional single oral dose of 90 mg ticagrelor 24 hours after the initiation of the study drug infusion (6th ticagrelor dose).

Aspirin (acetylsalicylic acid; ASA): Aspirin (ASA) 81 mg oral tablet (enteric coated) will be administered daily between Day –7 and in the morning before receiving study medication on Day 1. Subjects may resume ASA after discharge from the study. Subjects entering the study who are already taking ASA daily must be willing to document a daily 81 mg dose between Day –7 and Day 1 and must suspend further ASA doses until discharge from the clinical facility.

Evaluation Criteria:

Safety Assessments: Safety and tolerability will be assessed by monitoring and recording of AEs, clinical laboratory test results (hematology, coagulation, serum chemistry, and urinalysis), vital sign measurements (SBP and DBP, oral body temperature, respiratory rate [RR], and HR), 12 lead ECG, immunogenicity, biomarkers and physical examination findings.

Immunogenicity: Blood/serum samples will be screened for the presence of binding anti-drug antibodies (ADAs) at Check-in and on Days 1, 7 and 28 (±2 days).

Pharmacodynamic Assessments:

PD Data and Parameters Will be Generated from PRU, LTA, and PRI Assays:

VerifyNow®P2Y$_{12}$:

PRU at each assessment point

Percent of reversal in ticagrelor antiplatelet activity by PRU at each assessment point Maximum PRU Time to maximum PRU Maximum PRU within 4 hours Time to ≥180 PRU Time to ≥200 PRU Time to ≥220 PRU Time to 60%, 80%, and 90% of reversal in PRU within 30 minutes or 4 hours

LTA:

The maximum and final extent of aggregation for up to 4 platelet agonists, (20 μM adenosine diphosphate [ADP], 5 μM ADP, 1.6 mM arachidonic acid [AA], and 15 μM thrombin receptor activating peptide [TRAP]), will be recorded at each assessment point.

will be recorded at each assessment point.

Percent of reversal in ticagrelor antiplatelet aggregation

Maximum platelet aggregation

Time to maximum platelet aggregation

Maximum platelet aggregation within 4 hours

Time to 60%, 80%, and 90% of reversal in platelet aggregation

Number and percent of subjects achieving 60%, 80%, and 90% of reversal in platelet aggregation within 30 minutes or 4 hours VASP by ELISA:

PRI at each assessment point;

Percent of reversal in PRI at each assessment point;

Maximum PRI;

Time to maximum PRI;

Maximum PRI within 4 hours;

Time to 60%, 80%, and 90% of reversal in PRI;

Number and percent of subjects achieving 60%, 80%, and 90% of reversal in PRI within 30 minutes or 4 hours.

For Cohorts receiving a 6th dose of ticagrelor 24 hours following study drug, PD parameters will be calculated for Days 1 and Day 2 separately.

Pharmacokinetic Assessments:

Blood Collection for Plasma: Blood samples will be drawn at appropriate timepoints and plasma concentration of PB2452 at each sampling timepoint will be assessed. The following PK parameters will be calculated:

Area under the plasma concentration versus time curve (AUC) from time zero to the time of the last quantifiable concentration (AUC$^{0-\tau}$)

Observed maximum plasma concentration (C$_{max}$)

Time to reach the observed maximum plasma concentration (T$_{max}$)

AUC from time zero to 24 hours post-dose (AUC$_{0-24}$)

AUC from time zero to 48 hours post-dose (AUC$_{0-48}$)

AUC from time zero extrapolated to infinity (AUC$_{0-\infty}$; if data permit)

Terminal elimination half-life (t½; if data permit)

Clearance (CL; if data permit)

Plasma PK concentration for ticagrelor and the metabolite TAM at each sampling timepoint will be assessed. The following PK parameters will be calculated:

C$_{max}$

T$_{max}$

AUC$_{0-\tau}$

AUC from time zero to 12 hours post-dose (AUC$_{0-12}$)

AUC$_{0-24}$

AUC$_{0-48}$

AUC$_{0-\infty}$; if data permit t½; if data permit

For Cohorts receiving a 6th dose of ticagrelor 24 hours following study drug initiation, AUC$_{0-48}$ will not be calculated for neither plasma PB2452 nor ticagrelor/TAM. The remaining PK parameters may be calculated for Days 1 and 2 separately.

Urine Collection Pooled urine samples to assess urine PB2452, ticagrelor, and TAM concentrations will be collected over these intervals: before dosing (within 60 minutes prior to the first ticagrelor dose on Day –2) and 0 to 6, 6 to 12, and 12 to 24 hours. In patients receiving a 6th dose of ticagrelor, pooled urine samples to assess urine ticagrelor and TAM concentrations will be collected over these intervals beginning with the 6th ticagrelor dose: 0 to 6, 6 to 12, 12 to 24 hours.

Pharmacokinetic parameters for PB2452, ticagrelor, and TAM concentrations in urine for all subjects in the PK population to be calculated are:

Total amount of drug excreted in urine at 24 hours after dosing (Ae$_{24}$) and at 48 hours after dosing (Ae$_{48}$)

Total amount of drug excreted in urine from time t1 to t2 (Ae$_{t1-t2}$) hours when the values of t1 to t2 are 0 to 6, 6 to 12, 12 to 24 and 24 to 48 hours Fraction excreted in urine from 1 to 24 hours after dosing ($Fe_{24}$) and from 1 to 48 hours after dosing ($Fe_{48}$)

Renal clearance (CLr) for 24 hours after dosing

For Cohorts receiving a 6th dose of ticagrelor 24 hours following study drug initiation, $Fe_{48}$ and $Ae_{24-48}$ will not be calculated. Other urine PK parameters may be calculated for Day 1 and 2 separately.

Example 4—Study to Evaluate the Safety, Tolerability, Pharmacokinetics, and Pharmacodynamics of PB2452 with High-Dose Ticagrelor Pretreatment in Healthy Subjects A cohort of healthy subjects pretreated with 180 mg of oral ticagrelor twice daily for 48 hours was randomized in a 3:1 ratio (PB2452:placebo) to a dose and regimen of PB2452 or placebo. The dose regime of PB2452 was 12 g infused over 10 minutes, followed by 12 g over 6 hours, followed by 12 g over 18 hours. Platelet function was determined as described above.

INCORPORATION BY REFERENCE

All publications, patents, and patent publications cited are incorporated by reference herein in their entirety for all purposes.

This application incorporates by reference the following publication in its entirety for all purposes: US 2016/0130366.

REFERENCES

Bhatt D L, Hulot J S, Moliterno D J, Harrington R A. Antiplatelet and anticoagulation therapy for acute coronary syndromes. Circ Res. 2014; 114:1929-43.

Yusuf S, Zhao F, Mehta S R, et al.: Effects of clopidogrel in addition to aspirin in patients with acute coronary syndromes without S T-segment elevation. N Engl J Med. 2001; 345(23):1716.

Mehta S R, Yusuf S, Peters R J, et al.: Effects of pretreatment with clopidogrel and aspirin followed by long-term therapy in patients undergoing percutaneous coronary intervention: the PCI-CURE study. Lancet. 2001; 358 (9281):527-33.

Bhatt D L, Fox K A, Hacke W, et al.: Clopidogrel and aspirin versus aspirin alone for the prevention of atherothrombotic events. N Engl J Med. 2006; 354(16):1706-17.

Bhatt D L, Flather M D, Hacke W, et al.: Patients with prior myocardial infarction, stroke, or symptomatic peripheral arterial disease in the CHARISMA trial. J Am Coll Cardiol. 2007; 49(19):1982-8.

Chen Z M, Jiang L X, Chen Y P, et al.: Addition of clopidogrel to aspirin in 45,852 patients with acute myocardial infarction: randomised placebo-controlled trial. Lancet. 2005; 366(9497):1607-21.

Wiviott S D, Braunwald E, McCabe C H, et al.: Prasugrel versus clopidogrel in patients with acute coronary syndromes. N Engl J Med. 2007; 357(20):2001-15.

Prasugrel versus clopidogrel for acute coronary syndromes without revascularization. N Engl J Med. 2012; 367(14): 1297-309.

Wiviott S D, White H D, Ohman E M, et al.: Prasugrel versus clopidogrel for patients with unstable angina or non-S T-segment elevation myocardial infarction with or without angiography: a secondary, prespecified analysis of the TRILOGY ACS trial. Lancet. 2013; 382(9892): 605-13.

Koski R, Kennedy B. Comparative Review of Oral P2Y12 Inhibitors. P T. 2018; 43(6):352-357.

Wallentin L, Becker R C, Budaj A, et al.: Ticagrelor versus clopidogrel in patients with acute coronary syndromes. N Engl J Med. 2009; 361(11):1045-57.

Cannon C P, Harrington R A, James S, et al.: Comparison of ticagrelor with clopidogrel in patients with a planned invasive strategy for acute coronary syndromes (PLATO): a randomised double-blind study. Lancet. 2010; 375 (9711):283-93.

James S K, Roe M T, Cannon C P, Cornel J H, Horrow J, Husted S, et al. Ticagrelor versus clopidogrel in patients with acute coronary syndromes intended for non-invasive management: substudy from prospective randomised PLATelet inhibition and patient outcomes (PLATO) trial. BMJ. 2011; 342:d3527.

Plavix [prescribing information] (clopidogrel bisulfate). Bridgewater, NJ: Bristol-Myers Squibb/Sanofi Pharmaceuticals Partnership; 2017.

Brilinta [prescribing information] (ticagrelor). Wilmington, DE: Astra Zeneca L P; 2016 Effient [prescribing information] (prasugrel). Eli Lilly and Company, Indianapolis, IN, 46285, 2018

Ducrocq G, Amarenco P, Labreuche J, et al.: A history of stroke/transient ischemic attack indicates high risks of cardiovascular event and hemorrhagic stroke in patients with coronary artery disease. Circulation. 2013 Feb. 12; 127(6):730-8.

Bhatt D L Intensifying Platelet Inhibition—Navigating between Scylla and Charybdis. N Engl J Med. 2007; 357:2078-2081.

Capodanno D, Angiolillo D. Management of Antiplatelet Therapy in Patients With Coronary Artery Disease Requiring Cardiac and Noncardiac Surgery. Circulation. 2013; 128:2785-2798.

Douketis J D, Spyropoulos A C, Spencer F A, et al. Perioperative Management of Antithrombotic Therapy. Antithrombotic Therapy and Prevention of Thrombosis, 9th ed: American College of Chest Physicians Evidence-Based Clinical Practice Guidelines. Chest. 2012 February; 141(2 Suppl):e326S-e350S.

Buchanan A, Newton P, Pehrsson S, et al.: Structural and functional characterization of a specific antidote for ticagrelor. Blood. 2015; 125(22):3484-90.

Gurbel P A, Bliden K P, Butler K, et al. Randomized double-blind assessment of the ONSET and OFFSET of the antiplatelet effects of ticagrelor versus clopidogrel in patients with stable coronary artery disease: the ONSET/OFFSET study. Circulation. 2009; 120(25):2577-85.

Godier A, Taylor G, Gaussem P. Inefficacy of platelet transfusion to reverse ticagrelor. N Engl J Med. 2015; 372(2):196-7.

Teng R, Carlson G F, Nylander S, Andersson T L. Effects of autologous platelet transfusion on platelet inhibition in ticagrelor- and clopidogrel-treated subjects. J Thromb Haemost. 2016; 14:2342-52.

Jin L, Yu H, Dong T, Zhang B, Yan H, Liao H, Zou X. The Prognostic Value of ADP-Induced Platelet Aggregation for Bleeding Complications in Low—Intermediate Risk Patients with Acute Coronary Syndrome Taking Clopidogrel After Percutaneous Coronary Intervention. Heart Lung Circ. 2017 January; 26(1):49-57

Reed G W, Kumar A, Guo J, et al.: Point-of-care platelet function testing predicts bleeding in patients exposed to clopidogrel undergoing coronary artery bypass grafting: Verify pre-op TIMI 45—a pilot study. Clin Cardiol. 2015; 38(2):92-8.

Mangiacapra F, Ricottini E, Barbato E, et al.: Incremental Value of Platelet Reactivity Over a Risk Score of Clinical and Procedural Variables in Predicting Bleeding After Percutaneous Coronary Intervention via the Femoral Approach: Development and Validation of a New Bleeding Risk Score. Circ Cardiovasc Interv. 2015; 8(5). pii: e002106.

Tantry U S, Bonello L, Aradi D, et al.: Consensus and update on the definition of on-treatment platelet reactivity to adenosine diphosphate associated with ischemia and bleeding. J Am Coll Cardiol. 2013; 62(24):2261-73.

Aradi D, Kirtane A, Bonello L, et al.: Bleeding and stent thrombosis on P2Y12-inhibitors: collaborative analysis on the role of platelet reactivity for risk stratification after percutaneous coronary intervention. Eur Heart J. 2015; 36(27):1762-71.

The invention claimed is:

1. A method of reversing ticagrelor-associated bleeding, or reducing the risk of said bleeding, in a patient who had previously been administered ticagrelor, comprising administering to the patient a pharmaceutical composition comprising a dose of between about 18 g and about 48 g of an antibody or fragment thereof that binds to ticagrelor ((1S, 2S,3R,5S)-3-[7-{[(1R,2S)-2-(3,4-difluorophenyl)cyclopropyl]amino}-5-(propylthio)-3H-[1,2,3]triazolo[4,5-d]pyrimidin-3-yl]-5-(2-hydroxyethoxy)cyclopentane-1,2-diol) or a metabolite or derivative thereof, wherein the antibody or fragment thereof comprises complementarity-determining region (CDR) combinations selected from the group consisting of:

a) SEQ ID NO:53 (VH CDR1), SEQ ID NO:54 (VH CDR2), SEQ ID NO:55 (VH CDR3), SEQ ID NO:58 (VL CDR1), SEQ ID NO:59 (VL CDR2), and SEQ ID NO:60 (VL CDR3);

b) SEQ ID NO:63 (VH CDR1), SEQ ID NO:64 (VH CDR2), SEQ ID NO:65 (VH CDR3), SEQ ID NO:68 (VL CDR1), SEQ ID NO:69 (VL CDR2), and SEQ ID NO:70 (VL CDR3); and c) SEQ ID NO:73 (VH CDR1), SEQ ID NO:74 (VH CDR2), SEQ ID NO:75 (VH CDR3), SEQ ID NO:78 (VL CDR1), SEQ ID NO:79 (VL CDR2), and SEQ ID NO:80 (VL CDR3).

2. The method of claim 1, wherein the antibody or fragment thereof comprises a combination of heavy chain variable region (VH) and light chain variable region (VL) sequences selected from the group consisting of SEQ ID NO:52 and SEQ ID NO:57; SEQ ID NO: 62 and SEQ ID NO:67; and SEQ ID NO:72 and SEQ ID NO:77.

3. The method of claim 1, wherein the pharmaceutical composition is administered to the patient intravenously.

4. The method of claim 3, wherein the pharmaceutical composition is administered intravenously over about 15 minutes to about 36 hours.

5. The method of claim 1, wherein the pharmaceutical composition is administered in the following schedule: 12 g of the antibody or fragment thereof infused over 10 minutes, followed by 12 g of the antibody or fragment thereof over 6 hours, followed by 12 g of the antibody or fragment thereof over 18 hours.

6. The method of claim 1, wherein the pharmaceutical composition comprises about 50 mg/mL to about 200 mg/mL of the antibody or fragment thereof, about 5 mM to about 50 mM histidine/histidine hydrochloride buffer, about 100 mM to about 300 mM sucrose, and about 0.01% (w/v) to about 1.0% (w/v) polysorbate 80, at about pH 5.5 to about 6.5.

7. The method of claim 6, wherein the pharmaceutical formulation comprises 100 mg/mL of the antibody or fragment thereof, 25 mM histidine/histidine hydrochloride buffer, 290 mM sucrose, and 0.05% (w/v) polysorbate 80, at about pH 6.0.

8. The method of claim 1, wherein the ticagrelor-associated bleeding is major bleeding.

9. The method of claim 1, wherein the patient requires urgent surgery or intervention.

10. The method of claim 1, wherein the patient is at risk of developing, or has been diagnosed with, a disease selected from the group consisting of Acute Coronary Syndrome (ACS), myocardial infarction (MI), unstable angina, stable ischemic heart disease, sickle cell disease, atrial fibrillation, coronary arterial disease, peripheral arterial disease, ischemic stroke requiring one or more coronary stents, carotid artery stents requiring stents following an intracranial aneurysm, and arterio-venous fistulae created for hemodialysis.

11. The method of claim 1, wherein administration of the antibody or fragment thereof restores platelet aggregation to at least 80% of baseline within 1 minute to 60 minutes of starting administration.

12. The method of claim 11, wherein administration of the antibody or fragment thereof restores platelet aggregation within 5 minutes of starting administration.

13. The method of claim 11, wherein the restoration of platelet aggregation is sustained for at least 12 hours after starting administration.

14. The method of claim 1, wherein the antibody or a fragment thereof comprises a CDR combination comprising: SEQ ID NO:73 (VH CDR1), SEQ ID NO:74 (VH CDR2), SEQ ID NO:75 (VH CDR3), SEQ ID NO:78 (VL CDR1), SEQ ID NO:79 (VL CDR2), and SEQ ID NO:80 (VL CDR3).

15. The method of claim 1, wherein the antibody or fragment thereof comprises a combination of heavy chain variable region (VH) and light chain variable region (VL) sequences comprising SEQ ID NO:72 and SEQ ID NO:77.

16. The method of claim 1, wherein the patient has been administered ticagrelor before administration of the anti-ticagrelor antibody or fragment thereof.

17. The method of claim 1, wherein the antibody or fragment thereof is an antibody fragment.

18. The method of claim 17, wherein the antibody fragment is a Fab.

19. The method of claim 1, wherein the pharmaceutical composition is administered in three or more segments, and wherein the first segment is a bolus.

20. The method of claim 1, wherein the patient is at risk of developing, or has been diagnosed with Acute Coronary Syndrome (ACS).

21. The method of claim 1, wherein the patient is at risk of developing, or has been diagnosed with myocardial infarction (MI).

22. The method of claim 1, wherein the patient is at risk of developing, or has been diagnosed with ischemic stroke.

23. The method of claim 1, wherein the patient has been administered aspirin (acetylsalicylic acid).

24. The method of claim 1, wherein the method reverses ticagrelor-associated bleeding in the patient.

25. The method of claim 1, wherein the method reduces the risk of ticagrelor-associated bleeding in the patient.

26. The method of claim 1, wherein the dose is 18 g.

27. The method of claim 1, wherein the dose is 24 g.

28. The method of claim 1, wherein the dose is 36 g.

29. The method of claim 1, wherein the antibody or fragment thereof binds to ticagrelor active metabolite (TAM).

30. The method of claim 1, wherein the patient has been administered ticagrelor and one or more additional drugs that inhibit the activity of cytochrome P450 isoform 3A (CYP3A).

31. The method of claim 1, wherein the patient is receiving concomitant oral or intravenous therapy with a strong CYP3A inhibitor.

32. The method of claim 18, wherein the Fab is a human IgG1 monoclonal Fab.

33. The method of claim 1, wherein the pharmaceutical composition comprises about 100 mg/mL of the antibody or fragment thereof.

34. A method of reversing ticagrelor-associated bleeding, or reducing the risk of said bleeding, in a patient who had previously been administered ticagrelor, comprising administering to the patient a pharmaceutical composition comprising a dose of about 36 g of an antibody Fab fragment that binds to ticagrelor ((1S,2S,3R,5S)-3-[7-{[(1R,2S)-2-(3,4-difluorophenyl)cyclopropyl]amino}-5-(propylthio)-3H-[1,2,3]triazolo[4,5-d]pyrimidin-3-yl]-5-(2-hydroxyethoxy)cyclopentane-1,2-diol) or ticagrelor active metabolite (TAM), wherein the Fab thereof comprises complementarity-determining region (CDR) combination: SEQ ID NO:73 (VH CDR1), SEQ ID NO:74 (VH CDR2), SEQ ID NO:75 (VH CDR3), SEQ ID NO:78 (VL CDR1), SEQ ID NO:79 (VL CDR2), and SEQ ID NO:80 (VL CDR3);

wherein the pharmaceutical composition is administered in the following schedule: 12 g of the antibody or fragment thereof infused over 10 minutes, followed by 12 g of the antibody or fragment thereof over 6 hours, followed by 12 g of the antibody or fragment thereof over 18 hours.

35. The method of claim 34, wherein the Fab comprises a combination of heavy chain variable region (VH) and light chain variable region (VL) sequences comprising SEQ ID NO:72 and SEQ ID NO:77.

36. The method of claim 35, wherein the patient requires urgent surgery or intervention.

37. The method of claim 35, wherein the patient is at risk of developing, or has been diagnosed with, a disease selected from the group consisting of Acute Coronary Syndrome (ACS), myocardial infarction (MI), unstable angina, stable ischemic heart disease, sickle cell disease, atrial fibrillation, coronary arterial disease, peripheral arterial disease, ischemic stroke requiring one or more coronary stents, carotid artery stents requiring stents following an intracranial aneurysm, and arterio-venous fistulae created for hemodialysis.

38. The method of claim 35, wherein the patient is receiving concomitant oral or intravenous therapy with a strong CYP3A inhibitor.

39. The method of claim 35, wherein the Fab is a human IgG1 monoclonal Fab.

40. The method of claim 35, wherein the pharmaceutical composition comprises about 100 mg/mL of the antibody or fragment thereof.

* * * * *

SEQUENCE LISTING

```
<160> NUMBER OF SEQ ID NOS: 86

<210> SEQ ID NO 1
<211> LENGTH: 363
<212> TYPE: DNA
<213> ORGANISM: Homo sapiens

<400> SEQUENCE: 1
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc aacagagtac     300
gacctgcaac ggcctttcgg gtttgacttc tggggcaagg ggacaatggt caccgtctcg     360
agt                                                                   363

<210> SEQ ID NO 2
<211> LENGTH: 121
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Tyr Asp Leu Gln Arg Pro Phe Gly Phe Asp Phe Trp Gly
            100                 105                 110

Lys Gly Thr Met Val Thr Val Ser Ser
        115                 120

<210> SEQ ID NO 3
<211> LENGTH: 5
<212> TYPE: PRT
<213> ORGANISM: Homo sapiens

<400> SEQUENCE: 3

Ser Tyr Ala Met Ser
1               5
```

-continued

```
<210> SEQ ID NO 4
<211> LENGTH: 17
<212> TYPE: PRT
<213> ORGANISM: Homo sapiens

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 12
<212> TYPE: PRT
<213> ORGANISM: Homo sapiens

<400> SEQUENCE: 5

Glu Tyr Asp Leu Gln Arg Pro Phe Gly Phe Asp Phe
1               5                   10

<210> SEQ ID NO 6
<211> LENGTH: 333
<212> TYPE: DNA
<213> ORGANISM: Homo sapiens

<400> SEQUENCE: 6
tcctatgtgc tgactcagcc accctcagcg tctggggccc ccgggcagag ggctaccatc      60
tcctgctctg gaagcagctc caacatcgga agtaatcttg tgaactggta ccaacaattc     120
ccaggagagg cccccaagct cctcatcttt agtgacaatc aacgaccctc aggggtccct     180
gaccgattct ctggctccag gtctggcacc tcagcctccc tggccatcag tgggctccag     240
tccgaggatg aggctgatta ttactgtgca acgtgggatg acagactgga tggttatgtg     300
gtattcggcg gagggaccaa gctgaccgtc cta                                  333

<210> SEQ ID NO 7
<211> LENGTH: 111
<212> TYPE: PRT
<213> ORGANISM: Homo sapiens

<400> SEQUENCE: 7

Ser Tyr Val Leu Thr Gln Pro Pro Ser Ala Ser Gly Ala Pro Gly Gln
1               5                   10                  15

Arg Ala Thr Ile Ser Cys Ser Gly Ser Ser Ser Asn Ile Gly Ser Asn
            20                  25                  30

Leu Val Asn Trp Tyr Gln Gln Phe Pro Gly Glu Ala Pro Lys Leu Leu
        35                  40                  45

Ile Phe Ser Asp Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Arg Leu
                85                  90                  95

Asp Gly Tyr Val Val Phe Gly Gly Gly Thr Lys Leu Thr Val Leu
            100                 105                 110

<210> SEQ ID NO 8
<211> LENGTH: 13
<212> TYPE: PRT
<213> ORGANISM: Homo sapiens
```

<400> SEQUENCE: 8

Ser Gly Ser Ser Ser Asn Ile Gly Ser Asn Leu Val Asn
1               5                   10

<210> SEQ ID NO 9
<211> LENGTH: 7
<212> TYPE: PRT
<213> ORGANISM: Homo sapiens

<400> SEQUENCE: 9

Ser Asp Asn Gln Arg Pro Ser
1               5

<210> SEQ ID NO 10
<211> LENGTH: 12
<212> TYPE: PRT
<213> ORGANISM: Homo sapiens

<400> SEQUENCE: 10

Ala Thr Trp Asp Asp Arg Leu Asp Gly Tyr Val Val
1               5                   10

<210> SEQ ID NO 11
<211> LENGTH: 345
<212> TYPE: DNA
<213> ORGANISM: Homo sapiens

<400> SEQUENCE: 11
caggtacagc tgcagcagtc aggggctgag gtgaagaagc ctggggcctc agtgaaggtt      60
tcctgcaagg cttctggata caccttcatt acctatggta ttcactgggt gcgccaggcc     120
cccggacaag ggcttgagtg gatgggatgg atcgaccccg ggcatggtta cacaaaatat     180
tcacagaagt tccagggcag agtcaccatt accagggaca catccgcgag cacagcctac     240
atggagatga gcagcctcag atctgaagac acggctgtgt attactgtgc gagagcggac     300
ctgggtgact actggggccg gggaaccctg gtcaccgtct cgagt                     345

<210> SEQ ID NO 12
<211> LENGTH: 115
<212> TYPE: PRT
<213> ORGANISM: Homo sapiens

<400> SEQUENCE: 12

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Ile Thr Tyr
                20                  25                  30

Gly Ile His Trp Val Arg Gln Ala Pro Gly Gln Gly Leu Glu Trp Met
            35                  40                  45

Gly Trp Ile Asp Pro Gly His Gly Tyr Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Met Ser Ser Leu Arg Ser Glu Asp Thr Ala Val Tyr Tyr Cys
                85                  90                  95

Ala Arg Ala Asp Leu Gly Asp Tyr Trp Gly Arg Gly Thr Leu Val Thr
            100                 105                 110

Val Ser Ser
        115

```
<210> SEQ ID NO 13
<211> LENGTH: 5
<212> TYPE: PRT
<213> ORGANISM: Homo sapiens

<400> SEQUENCE: 13

Thr Tyr Gly Ile His
1               5

<210> SEQ ID NO 14
<211> LENGTH: 17
<212> TYPE: PRT
<213> ORGANISM: Homo sapiens

<400> SEQUENCE: 14

Trp Ile Asp Pro Gly His Gly Tyr Thr Lys Tyr Ser Gln Lys Phe Gln
1               5                   10                  15

Gly

<210> SEQ ID NO 15
<211> LENGTH: 6
<212> TYPE: PRT
<213> ORGANISM: Homo sapiens

<400> SEQUENCE: 15

Ala Asp Leu Gly Asp Tyr
1               5

<210> SEQ ID NO 16
<211> LENGTH: 330
<212> TYPE: DNA
<213> ORGANISM: Homo sapiens

<400> SEQUENCE: 16
cagtctgtcg tgacgcagcc gccctcagtg tctgcggccc caggacagaa ggtcaccatc        60
tcctgctctg gaagcagctc caacattggg aagaattatg tttcctggtt ccagcagctc       120
ccaggtacag cccccaaact cctcatttat gacaatcata agcgaccctc agggattcct       180
gaccgattct ctgcctccaa gtctggcacg tcagccaccc tggtcatctc cggtctccag       240
actggggacg aggcccatta ttactgcgga acatgggata ccagactgag tgctggggtg       300
ttcggcggag ggaccaaggt caccgtccta                                        330

<210> SEQ ID NO 17
<211> LENGTH: 110
<212> TYPE: PRT
<213> ORGANISM: Homo sapiens

<400> SEQUENCE: 17

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Lys Asn
                20                  25                  30

Tyr Val Ser Trp Phe Gln Gln Leu Pro Gly Thr Ala Pro Lys Leu Leu
            35                  40                  45

Ile Tyr Asp Asn His Lys Arg Pro Ser Gly Ile Pro Asp Arg Phe Ser
        50                  55                  60

Ala Ser Lys Ser Gly Thr Ser Ala Thr Leu Val Ile Ser Gly Leu Gln
65                  70                  75                  80
```

```
Thr Gly Asp Glu Ala His Tyr Tyr Cys Gly Thr Trp Asp Thr Arg Leu
                85                  90                  95

Ser Ala Gly Val Phe Gly Gly Gly Thr Lys Val Thr Val Leu
            100                 105                 110

<210> SEQ ID NO 18
<211> LENGTH: 13
<212> TYPE: PRT
<213> ORGANISM: Homo sapiens

<400> SEQUENCE: 18

Ser Gly Ser Ser Ser Asn Ile Gly Lys Asn Tyr Val Ser
1               5                   10

<210> SEQ ID NO 19
<211> LENGTH: 7
<212> TYPE: PRT
<213> ORGANISM: Homo sapiens

<400> SEQUENCE: 19

Asp Asn His Lys Arg Pro Ser
1               5

<210> SEQ ID NO 20
<211> LENGTH: 11
<212> TYPE: PRT
<213> ORGANISM: Homo sapiens

<400> SEQUENCE: 20

Gly Thr Trp Asp Thr Arg Leu Ser Ala Gly Val
1               5                   10

<210> SEQ ID NO 21
<211> LENGTH: 360
<212> TYPE: DNA
<213> ORGANISM: Homo sapiens

<400> SEQUENCE: 21
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgg ccatgatagt     300
agtggttact cctactcctt tgacttctgg gggcggggga ccacggtcac cgtctcgagt     360

<210> SEQ ID NO 22
<211> LENGTH: 120
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly His Asp Ser Ser Gly Tyr Ser Tyr Ser Phe Asp Phe Trp Gly Arg
            100                 105                 110

Gly Thr Thr Val Thr Val Ser Ser
        115                 120

<210> SEQ ID NO 23
<211> LENGTH: 5
<212> TYPE: PRT
<213> ORGANISM: Homo sapiens

<400> SEQUENCE: 23

Ser Tyr Ala Met Ser
1               5

<210> SEQ ID NO 24
<211> LENGTH: 17
<212> TYPE: PRT
<213> ORGANISM: Homo sapiens

<400> SEQUENCE: 24

Ala Ile Ser Gly Ser Gly Gly Ser Thr Tyr Tyr Ala Asp Ser Val Lys
1               5                   10                  15

Gly

<210> SEQ ID NO 25
<211> LENGTH: 11
<212> TYPE: PRT
<213> ORGANISM: Homo sapiens

<400> SEQUENCE: 25

Asp Ser Ser Gly Tyr Ser Tyr Ser Phe Asp Phe
1               5                   10

<210> SEQ ID NO 26
<211> LENGTH: 330
<212> TYPE: DNA
<213> ORGANISM: Homo sapiens

<400> SEQUENCE: 26
cagtctgtgt tgacgcagcc gccctcagcg tctgggaccc ccgggcagag ggtcaccatc      60
tcttgttctg gcaacatctc caacatcgga agtaacactg tcaactggta tcaacacgtc     120
ccaggagcgg cccccagact cctcatctat gttaatgatc agcggccgtc aggggtccct     180
gaccgattct ctggctccaa gtctggcacc tcagcctccc tggccatcag tgggctccag     240
tctgaagatg aggctgatta ttactgtgca acgtgggatg acaccctgaa tggaggggtc     300
ttcggcggag ggaccaagct gaccgtccta                                       330

<210> SEQ ID NO 27
<211> LENGTH: 110
<212> TYPE: PRT
<213> ORGANISM: Homo sapiens

<400> SEQUENCE: 27

Gln Ser Val Leu Thr Gln Pro Pro Ser Ala Ser Gly Thr Pro Gly Gln
1               5                   10                  15

Arg Val Thr Ile Ser Cys Ser Gly Asn Ile Ser Asn Ile Gly Ser Asn
```

-continued

```
                20                  25                  30
Thr Val Asn Trp Tyr Gln His Val Pro Gly Ala Ala Pro Arg Leu Leu
          35                  40                  45

Ile Tyr Val Asn Asp Gln Arg Pro Ser Gly Val Pro Asp Arg Phe Ser
     50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Thr Leu
               85                  90                  95

Asn Gly Gly Val Phe Gly Gly Gly Thr Lys Leu Thr Val Leu
          100                 105                 110
```

<210> SEQ ID NO 28
<211> LENGTH: 13
<212> TYPE: PRT
<213> ORGANISM: Homo sapiens

<400> SEQUENCE: 28

```
Ser Gly Asn Ile Ser Asn Ile Gly Ser Asn Thr Val Asn
1               5                   10
```

<210> SEQ ID NO 29
<211> LENGTH: 7
<212> TYPE: PRT
<213> ORGANISM: Homo sapiens

<400> SEQUENCE: 29

```
Val Asn Asp Gln Arg Pro Ser
1               5
```

<210> SEQ ID NO 30
<211> LENGTH: 11
<212> TYPE: PRT
<213> ORGANISM: Homo sapiens

<400> SEQUENCE: 30

```
Ala Thr Trp Asp Asp Thr Leu Asn Gly Gly Val
1               5                   10
```

<210> SEQ ID NO 31
<211> LENGTH: 387
<212> TYPE: DNA
<213> ORGANISM: Homo sapiens

<400> SEQUENCE: 31

```
caggtgcagc tgcaggagtc cggggctgag gtgaagaagc ctgggtcctc ggtgagggtc        60
tcctgcaagg cttctggagg caccttcgac agttatagta tccattgggt gcgccaggcc       120
cctggacaag ggcttgagtg gatgggaggg atcatccctg cctttgggac attaagcagc       180
gcacaggact ccaggccag agtcaccatt agcgcggaca gtccacgag cacagcctat        240 atggagctga gcggcctgag atctgaggac acggccgtat attactgtgc gagagggtcc       300
catctttacg atttttggag tgcttctcat cccccccaatg atgctcttgc tatttggggc       360
caaggaaccc tggtcaccgt ctcgagt                                          387
```

<210> SEQ ID NO 32
<211> LENGTH: 129
<212> TYPE: PRT
<213> ORGANISM: Homo sapiens

<400> SEQUENCE: 32

```
Gln Val Gln Leu Gln Glu Ser Gly Ala Glu Val Lys Lys Pro Gly Ser
1               5                   10                  15

Ser Val Arg Val Ser Cys Lys Ala Ser Gly Gly Thr Phe Asp Ser Tyr
            20                  25                  30

Ser Ile His Trp Val Arg Gln Ala Pro Gly Gln Gly Leu Glu Trp Met
        35                  40                  45

Gly Gly Ile Ile Pro Ala Phe Gly Thr Leu Ser Ser Ala Gln Asp Phe
    50                  55                  60

Gln Ala Arg Val Thr Ile Ser Ala Asp Lys Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Ala Arg Gly Ser His Leu Tyr Asp Phe Trp Ser Ala Ser His Pro Pro
            100                 105                 110

Asn Asp Ala Leu Ala Ile Trp Gly Gln Gly Thr Leu Val Thr Val Ser
        115                 120                 125

Ser

<210> SEQ ID NO 33
<211> LENGTH: 5
<212> TYPE: PRT
<213> ORGANISM: Homo sapiens

<400> SEQUENCE: 33

Ser Tyr Ser Ile His
1               5

<210> SEQ ID NO 34
<211> LENGTH: 17
<212> TYPE: PRT
<213> ORGANISM: Homo sapiens

<400> SEQUENCE: 34

Gly Ile Ile Pro Ala Phe Gly Thr Leu Ser Ser Ala Gln Asp Phe Gln
1               5                   10                  15

Ala

<210> SEQ ID NO 35
<211> LENGTH: 20
<212> TYPE: PRT
<213> ORGANISM: Homo sapiens

<400> SEQUENCE: 35

Gly Ser His Leu Tyr Asp Phe Trp Ser Ala Ser His Pro Pro Asn Asp
1               5                   10                  15

Ala Leu Ala Ile
            20

<210> SEQ ID NO 36
<211> LENGTH: 330
<212> TYPE: DNA
<213> ORGANISM: Homo sapiens

<400> SEQUENCE: 36
cagtctgtcg tgacgcagcc gccctcagtg tctgcggccc caggacagaa ggtcaccatc      60
tcctgctctg gaagcaactc cgacattggc aacaattatg tgtcgtggta ccaacagctc     120
ccaggaacag cccccaaact cctcatttat gacaataata aacgaccctc agggattcct     180
```

-continued gaccgattct ctggctccaa gtctggcacg tcagccaccc tggccatcac cggactccag      240
gctggggacg aggccgatta ttactgcggg acatgggata tcagcctgag cgctggcttg      300
ttcggcggag ggaccaaggt caccgtccta      330

<210> SEQ ID NO 37
<211> LENGTH: 110
<212> TYPE: PRT
<213> ORGANISM: Homo sapiens

<400> SEQUENCE: 37

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Ala Gly Asp Glu Ala Asp Tyr Tyr Cys Gly Thr Trp Asp Ile Ser Leu
                85                  90                  95

Ser Ala Gly Leu Phe Gly Gly Gly Thr Lys Val Thr Val Leu
            100                 105                 110

<210> SEQ ID NO 38
<211> LENGTH: 13
<212> TYPE: PRT
<213> ORGANISM: Homo sapiens

<400> SEQUENCE: 38

Ser Gly Ser Asn Ser Asp Ile Gly Asn Asn Tyr Val Ser
1               5                   10

<210> SEQ ID NO 39
<211> LENGTH: 7
<212> TYPE: PRT
<213> ORGANISM: Homo sapiens

<400> SEQUENCE: 39

Asp Asn Asn Lys Arg Pro Ser
1               5

<210> SEQ ID NO 40
<211> LENGTH: 11
<212> TYPE: PRT
<213> ORGANISM: Homo sapiens

<400> SEQUENCE: 40

Gly Thr Trp Asp Ile Ser Leu Ser Ala Gly Leu
1               5                   10

<210> SEQ ID NO 41
<211> LENGTH: 387
<212> TYPE: DNA
<213> ORGANISM: Homo sapiens

<400> SEQUENCE: 41
caggtgcagc tgcaggagtc cgggggctgag gtgaagaagc ctgggtcctc ggtgagggtc      60
tcctgcaagg cttctggagg caccttcgac agttatagta tccattgggt cgcgccaggcc     120

-continued

```
cctggacaag ggcttgagtg gatgggaggg atcatccctg cctttgggac attaagcagc        180
gcacaggact tccaggccag agtcaccatt agcgcggaca agtccacgag cacagcctat        240
atggagctga gcggcctgag atctgaggac acggccgtat attactgtgc gagagggagc        300
ttcgactaca ggttttggag tgcttctcat ccccccaatg atgctcttgc tatttggggc        360
caaggaaccc tggtcaccgt ctcgagt                                            387
```

```
<210> SEQ ID NO 42
<211> LENGTH: 129
<212> TYPE: PRT
<213> ORGANISM: Homo sapiens

<400> SEQUENCE: 42

Gln Val Gln Leu Gln Glu Ser Gly Ala Glu Val Lys Lys Pro Gly Ser
1               5                   10                  15

Ser Val Arg Val Ser Cys Lys Ala Ser Gly Gly Thr Phe Asp Ser Tyr
            20                  25                  30

Ser Ile His Trp Val Arg Gln Ala Pro Gly Gln Gly Leu Glu Trp Met
        35                  40                  45

Gly Gly Ile Ile Pro Ala Phe Gly Thr Leu Ser Ser Ala Gln Asp Phe
    50                  55                  60

Gln Ala Arg Val Thr Ile Ser Ala Asp Lys Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Ala Arg Gly Ser Phe Asp Tyr Arg Phe Trp Ser Ala Ser His Pro Pro
            100                 105                 110

Asn Asp Ala Leu Ala Ile Trp Gly Gln Gly Thr Leu Val Thr Val Ser
        115                 120                 125

Ser
```

```
<210> SEQ ID NO 43
<211> LENGTH: 5
<212> TYPE: PRT
<213> ORGANISM: Homo sapiens

<400> SEQUENCE: 43

Ser Tyr Ser Ile His
1               5
```

```
<210> SEQ ID NO 44
<211> LENGTH: 17
<212> TYPE: PRT
<213> ORGANISM: Homo sapiens

<400> SEQUENCE: 44

Gly Ile Ile Pro Ala Phe Gly Thr Leu Ser Ser Ala Gln Asp Phe Gln
1               5                   10                  15

Ala
```

```
<210> SEQ ID NO 45
<211> LENGTH: 20
<212> TYPE: PRT
<213> ORGANISM: Homo sapiens

<400> SEQUENCE: 45

Gly Ser Phe Asp Tyr Arg Phe Trp Ser Ala Ser His Pro Pro Asn Asp
1               5                   10                  15
```

-continued

Ala Leu Ala Ile
            20

<210> SEQ ID NO 46
<211> LENGTH: 330
<212> TYPE: DNA
<213> ORGANISM: Homo sapiens

<400> SEQUENCE: 46
cagtctgtcg tgacgcagcc gccctcagtg tctgcggccc caggacagaa ggtcaccatc        60
tcctgctctg gaagcaactc cgacattggc aacaattatg tgtcgtggta ccaacagctc       120
ccaggaacag cccccaaact cctcatttat gacaataata aacgaccctc agggattcct       180
gaccgattct ctggctccaa gtctggcacg tcagccaccc tggccatcac cggactccag       240 gctgggacg aggccgatta ttactgcggg acatgggata tcagcctgag cgctggcttg       300
ttcggcggag ggaccaaggt caccgtccta       330

<210> SEQ ID NO 47
<211> LENGTH: 110
<212> TYPE: PRT
<213> ORGANISM: Homo sapiens

<400> SEQUENCE: 47

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Ala Gly Asp Glu Ala Asp Tyr Tyr Cys Gly Thr Trp Asp Ile Ser Leu
                85                  90                  95

Ser Ala Gly Leu Phe Gly Gly Gly Thr Lys Val Thr Val Leu
            100                 105                 110

<210> SEQ ID NO 48
<211> LENGTH: 13
<212> TYPE: PRT
<213> ORGANISM: Homo sapiens

<400> SEQUENCE: 48

Ser Gly Ser Asn Ser Asp Ile Gly Asn Asn Tyr Val Ser
1               5                   10

<210> SEQ ID NO 49
<211> LENGTH: 7
<212> TYPE: PRT
<213> ORGANISM: Homo sapiens

<400> SEQUENCE: 49

Asp Asn Asn Lys Arg Pro Ser
1               5

<210> SEQ ID NO 50
<211> LENGTH: 11
<212> TYPE: PRT

<213> ORGANISM: Homo sapiens

<400> SEQUENCE: 50

Gly Thr Trp Asp Ile Ser Leu Ser Ala Gly Leu
1               5                   10

<210> SEQ ID NO 51
<211> LENGTH: 387
<212> TYPE: DNA
<213> ORGANISM: Homo sapiens

<400> SEQUENCE: 51
caggtgcagc tgcaggagtc cgggggctgag gtgaagaagc ctgggtcctc ggtgagggtc      60
tcctgcaagg cttctggagg caccttcgac agttatagta tccattgggt gcgccaggcc     120
cctggacaag ggcttgagtg gatgggaggg atcatccctg cctttgggac attaagcagc     180
gcacaggact ccaggccag agtcaccatt agcgcggaca agtccacgag cacagcctat      240
atggagctga gcggcctgag atctgaggac acggccgtat attactgtgc gagaggctcc     300
ttcgactact acttttggag tgcttctcat ccccccaatg atgctcttgc tatttggggc     360
caaggaaccc tggtcaccgt ctcgagt                                         387

<210> SEQ ID NO 52
<211> LENGTH: 129
<212> TYPE: PRT
<213> ORGANISM: Homo sapiens

<400> SEQUENCE: 52

Gln Val Gln Leu Gln Glu Ser Gly Ala Glu Val Lys Lys Pro Gly Ser
1               5                   10                  15

Ser Val Arg Val Ser Cys Lys Ala Ser Gly Gly Thr Phe Asp Ser Tyr
            20                  25                  30

Ser Ile His Trp Val Arg Gln Ala Pro Gly Gln Gly Leu Glu Trp Met
        35                  40                  45

Gly Gly Ile Ile Pro Ala Phe Gly Thr Leu Ser Ser Ala Gln Asp Phe
    50                  55                  60

Gln Ala Arg Val Thr Ile Ser Ala Asp Lys Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Ala Arg Gly Ser Phe Asp Tyr Tyr Phe Trp Ser Ala Ser His Pro Pro
            100                 105                 110

Asn Asp Ala Leu Ala Ile Trp Gly Gln Gly Thr Leu Val Thr Val Ser
        115                 120                 125

Ser

<210> SEQ ID NO 53
<211> LENGTH: 5
<212> TYPE: PRT
<213> ORGANISM: Homo sapiens

<400> SEQUENCE: 53

Ser Tyr Ser Ile His
1               5

<210> SEQ ID NO 54
<211> LENGTH: 17
<212> TYPE: PRT
<213> ORGANISM: Homo sapiens

<400> SEQUENCE: 54

Gly Ile Ile Pro Ala Phe Gly Thr Leu Ser Ser Ala Gln Asp Phe Gln
1               5                   10                  15

Ala

<210> SEQ ID NO 55
<211> LENGTH: 20
<212> TYPE: PRT
<213> ORGANISM: Homo sapiens

<400> SEQUENCE: 55

Gly Ser Phe Asp Tyr Tyr Phe Trp Ser Ala Ser His Pro Pro Asn Asp
1               5                   10                  15

Ala Leu Ala Ile
            20

<210> SEQ ID NO 56
<211> LENGTH: 330
<212> TYPE: DNA
<213> ORGANISM: Homo sapiens

<400> SEQUENCE: 56
cagtctgtcg tgacgcagcc gccctcagtg tctgcggccc caggacagaa ggtcaccatc      60
tcctgctctg gaagcaactc cgacattggc aacaattatg tgtcgtggta ccaacagctc     120
ccaggaacag cccccaaact cctcatttat gacaataata aacgaccctc agggattcct     180
gaccgattct ctggctccaa gtctggcacg tcagccaccc tggccatcac cggactccag     240
gctggggacg aggccgatta ttactgcggg acatgggata tcagcctgag cgctggcttg     300
ttcggcggag ggaccaaggt caccgtccta                                      330

<210> SEQ ID NO 57
<211> LENGTH: 110
<212> TYPE: PRT
<213> ORGANISM: Homo sapiens

<400> SEQUENCE: 57

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Ala Gly Asp Glu Ala Asp Tyr Tyr Cys Gly Thr Trp Asp Ile Ser Leu
                85                  90                  95

Ser Ala Gly Leu Phe Gly Gly Gly Thr Lys Val Thr Val Leu
            100                 105                 110

<210> SEQ ID NO 58
<211> LENGTH: 13
<212> TYPE: PRT
<213> ORGANISM: Homo sapiens

<400> SEQUENCE: 58

Ser Gly Ser Asn Ser Asp Ile Gly Asn Asn Tyr Val Ser
1               5                   10

<210> SEQ ID NO 59
<211> LENGTH: 7
<212> TYPE: PRT
<213> ORGANISM: Homo sapiens

<400> SEQUENCE: 59

Asp Asn Asn Lys Arg Pro Ser
1               5

<210> SEQ ID NO 60
<211> LENGTH: 11
<212> TYPE: PRT
<213> ORGANISM: Homo sapiens

<400> SEQUENCE: 60

Gly Thr Trp Asp Ile Ser Leu Ser Ala Gly Leu
1               5                   10

<210> SEQ ID NO 61
<211> LENGTH: 387
<212> TYPE: DNA
<213> ORGANISM: Homo sapiens

<400> SEQUENCE: 61
caggtgcagc tgcaggagtc cgggggctgag gtgaagaagc ctgggtcctc ggtgagggtc        60
tcctgcaagg cttctggagg caccttcgac agttatagta tccattgggt gcgccaggcc       120
cctggacaag ggcttgagtg gatgggaggg atcatccctg cctttgggac attaagcagc       180
gcacaggact tccaggccag agtcaccatt agcgcggaca gtccacgag cacagcctat        240 atggagctga gcggcctgag atctgaggac acggccgtat attactgtgc gagagggtcc       300
catctttacg attttttggag tgcttctcat ccccccaatg atgctcttgc tatttggggc       360
caaggaaccc tggtcaccgt ctcgagt                                           387

<210> SEQ ID NO 62
<211> LENGTH: 129
<212> TYPE: PRT
<213> ORGANISM: Homo sapiens

<400> SEQUENCE: 62

Gln Val Gln Leu Gln Glu Ser Gly Ala Glu Val Lys Lys Pro Gly Ser
1               5                   10                  15

Ser Val Arg Val Ser Cys Lys Ala Ser Gly Gly Thr Phe Asp Ser Tyr
            20                  25                  30

Ser Ile His Trp Val Arg Gln Ala Pro Gly Gln Gly Leu Glu Trp Met
        35                  40                  45

Gly Gly Ile Ile Pro Ala Phe Gly Thr Leu Ser Ser Ala Gln Asp Phe
    50                  55                  60

Gln Ala Arg Val Thr Ile Ser Ala Asp Lys Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Ala Arg Gly Ser His Leu Tyr Asp Phe Trp Ser Ala Ser His Pro Pro
            100                 105                 110

Asn Asp Ala Leu Ala Ile Trp Gly Gln Gly Thr Leu Val Thr Val Ser
        115                 120                 125

-continued

Ser

```
<210> SEQ ID NO 63
<211> LENGTH: 5
<212> TYPE: PRT
<213> ORGANISM: Homo sapiens

<400> SEQUENCE: 63

Ser Tyr Ser Ile His
1               5

<210> SEQ ID NO 64
<211> LENGTH: 17
<212> TYPE: PRT
<213> ORGANISM: Homo sapiens

<400> SEQUENCE: 64

Gly Ile Ile Pro Ala Phe Gly Thr Leu Ser Ser Ala Gln Asp Phe Gln
1               5                   10                  15

Ala

<210> SEQ ID NO 65
<211> LENGTH: 20
<212> TYPE: PRT
<213> ORGANISM: Homo sapiens

<400> SEQUENCE: 65

Gly Ser His Leu Tyr Asp Phe Trp Ser Ala Ser His Pro Pro Asn Asp
1               5                   10                  15

Ala Leu Ala Ile
            20

<210> SEQ ID NO 66
<211> LENGTH: 330
<212> TYPE: DNA
<213> ORGANISM: Homo sapiens

<400> SEQUENCE: 66
cagtctgtcg tgacgcagcc gccctcagtg tctgcggccc caggacagaa ggtcaccatc      60
tcctgctctg gaagcaactc cgacattggc aacaattatg tgtcgtggta ccaacagctc     120
ccaggaacag cccccaaact cctcatttat gacaataata aacgaccctc agggattcct     180
gaccgattct ctggctccaa gtctggcacg tcagccaccc tggccatcac cggactccag     240
gctggggacg aggccgatta ttactgcggg acatggctgt acgaccgggc cgtcggcttg     300
ttcggcggag ggaccaaggt caccgtccta                                       330

<210> SEQ ID NO 67
<211> LENGTH: 110
<212> TYPE: PRT
<213> ORGANISM: Homo sapiens

<400> SEQUENCE: 67

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60
```

```
Gly Ser Lys Ser Gly Thr Ser Ala Thr Leu Ala Ile Thr Gly Leu Gln
65                  70                  75                  80

Ala Gly Asp Glu Ala Asp Tyr Tyr Cys Gly Thr Trp Leu Tyr Asp Arg
                85                  90                  95

Ala Val Gly Leu Phe Gly Gly Gly Thr Lys Val Thr Val Leu
            100                 105                 110

<210> SEQ ID NO 68
<211> LENGTH: 13
<212> TYPE: PRT
<213> ORGANISM: Homo sapiens

<400> SEQUENCE: 68

Ser Gly Ser Asn Ser Asp Ile Gly Asn Asn Tyr Val Ser
1               5                   10

<210> SEQ ID NO 69
<211> LENGTH: 7
<212> TYPE: PRT
<213> ORGANISM: Homo sapiens

<400> SEQUENCE: 69

Asp Asn Asn Lys Arg Pro Ser
1               5

<210> SEQ ID NO 70
<211> LENGTH: 11
<212> TYPE: PRT
<213> ORGANISM: Homo sapiens

<400> SEQUENCE: 70

Gly Thr Trp Leu Tyr Asp Arg Ala Val Gly Leu
1               5                   10

<210> SEQ ID NO 71
<211> LENGTH: 387
<212> TYPE: DNA
<213> ORGANISM: Homo sapiens

<400> SEQUENCE: 71
caggtgcagc tgcaggagtc cggggctgag gtgaagaagc ctgggtcctc ggtgagggtc      60
tcctgcaagg cttctggagg caccttcgac agttatagta tccattgggt gcgccaggcc     120
cctggacaag ggcttgagtg gatgggaggg atcatccctg cctttgggac attaagcagc     180
gcacaggact tccaggccag agtcaccatt agcgcggaca gtccacgag cacagcctat      240 atggagctga gcggcctgag atctgaggac acggccgtat attactgtgc gagaggctcc     300
ttcgactact acttttggag tgcttctcat cccccaatg atgctcttgc tatttggggc      360
caaggaaccc tggtcaccgt ctcgagt                                          387

<210> SEQ ID NO 72
<211> LENGTH: 129
<212> TYPE: PRT
<213> ORGANISM: Homo sapiens

<400> SEQUENCE: 72

Gln Val Gln Leu Gln Glu Ser Gly Ala Glu Val Lys Lys Pro Gly Ser
1               5                   10                  15

Ser Val Arg Val Ser Cys Lys Ala Ser Gly Gly Thr Phe Asp Ser Tyr
            20                  25                  30
```

-continued

```
Ser Ile His Trp Val Arg Gln Ala Pro Gly Gln Gly Leu Glu Trp Met
        35                  40                  45

Gly Gly Ile Ile Pro Ala Phe Gly Thr Leu Ser Ser Ala Gln Asp Phe
    50                  55                  60

Gln Ala Arg Val Thr Ile Ser Ala Asp Lys Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Ala Arg Gly Ser Phe Asp Tyr Tyr Phe Trp Ser Ala Ser His Pro Pro
            100                 105                 110

Asn Asp Ala Leu Ala Ile Trp Gly Gln Gly Thr Leu Val Thr Val Ser
        115                 120                 125

Ser

<210> SEQ ID NO 73
<211> LENGTH: 5
<212> TYPE: PRT
<213> ORGANISM: Homo sapiens

<400> SEQUENCE: 73

Ser Tyr Ser Ile His
1               5

<210> SEQ ID NO 74
<211> LENGTH: 17
<212> TYPE: PRT
<213> ORGANISM: Homo sapiens

<400> SEQUENCE: 74

Gly Ile Ile Pro Ala Phe Gly Thr Leu Ser Ser Ala Gln Asp Phe Gln
1               5                   10                  15

Ala

<210> SEQ ID NO 75
<211> LENGTH: 20
<212> TYPE: PRT
<213> ORGANISM: Homo sapiens

<400> SEQUENCE: 75

Gly Ser Phe Asp Tyr Tyr Phe Trp Ser Ala Ser His Pro Pro Asn Asp
1               5                   10                  15

Ala Leu Ala Ile
            20

<210> SEQ ID NO 76
<211> LENGTH: 330
<212> TYPE: DNA
<213> ORGANISM: Homo sapiens

<400> SEQUENCE: 76
cagtctgtcg tgacgcagcc gccctcagtg tctgcggccc caggacagaa ggtcaccatc      60
tcctgctctg gaagcaactc cgacattggc aacaattatg tgtcgtggta ccaacagctc     120
ccaggaacag cccccaaact cctcatttat gacaataata aacgaccctc agggattcct     180
gaccgattct ctggctccaa gtctggcacg tcagccaccc tggccatcac cggactccag     240
gctggggacg aggccgatta ttactgcggg acatggctgt acgaccgggc cgtcggcttg     300
ttcggcggag ggaccaaggt caccgtccta                                      330
```

-continued

```
<210> SEQ ID NO 77
<211> LENGTH: 110
<212> TYPE: PRT
<213> ORGANISM: Homo sapiens

<400> SEQUENCE: 77

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Ala Gly Asp Glu Ala Asp Tyr Tyr Cys Gly Thr Trp Leu Tyr Asp Arg
                85                  90                  95

Ala Val Gly Leu Phe Gly Gly Gly Thr Lys Val Thr Val Leu
            100                 105                 110

<210> SEQ ID NO 78
<211> LENGTH: 13
<212> TYPE: PRT
<213> ORGANISM: Homo sapiens

<400> SEQUENCE: 78

Ser Gly Ser Asn Ser Asp Ile Gly Asn Asn Tyr Val Ser
1               5                   10

<210> SEQ ID NO 79
<211> LENGTH: 7
<212> TYPE: PRT
<213> ORGANISM: Homo sapiens

<400> SEQUENCE: 79

Asp Asn Asn Lys Arg Pro Ser
1               5

<210> SEQ ID NO 80
<211> LENGTH: 11
<212> TYPE: PRT
<213> ORGANISM: Homo sapiens

<400> SEQUENCE: 80

Gly Thr Trp Leu Tyr Asp Arg Ala Val Gly Leu
1               5                   10

<210> SEQ ID NO 81
<211> LENGTH: 234
<212> TYPE: PRT
<213> ORGANISM: Homo sapiens

<400> SEQUENCE: 81

Gln Val Gln Leu Gln Glu Ser Gly Ala Glu Val Lys Lys Pro Gly Ser
1               5                   10                  15

Ser Val Arg Val Ser Cys Lys Ala Ser Gly Gly Thr Phe Asp Ser Tyr
            20                  25                  30

Ser Ile His Trp Val Arg Gln Ala Pro Gly Gln Gly Leu Glu Trp Met
        35                  40                  45

Gly Gly Ile Ile Pro Ala Phe Gly Thr Leu Ser Ser Ala Gln Asp Phe
```

```
        50                  55                  60

Gln Ala Arg Val Thr Ile Ser Ala Asp Lys Ser Thr Ser Thr Ala Tyr
65                  70                  75                  80

Met Glu Leu Ser Gly Leu Arg Ser Glu Asp Thr Ala Val Tyr Tyr Cys
                    85                  90                  95

Ala Arg Gly Ser Phe Asp Tyr Tyr Phe Trp Ser Ala Ser His Pro Pro
                100                 105                 110

Asn Asp Ala Leu Ala Ile Trp Gly Gln Gly Thr Leu Val Thr Val Ser
            115                 120                 125

Ser Ala Ser Thr Lys Gly Pro Ser Val Phe Pro Leu Ala Pro Ser Ser
            130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
                180                 185                 190

Ser Leu Ser Ser Val Val Thr Val Pro Ser Ser Ser Leu Gly Thr Gln
            195                 200                 205

Thr Tyr Ile Cys Asn Val Asn His Lys Pro Ser Asn Thr Lys Val Asp
210                 215                 220

Lys Arg Val Glu Pro Lys Ser Cys Asp Lys
225                 230
```

```
<210> SEQ ID NO 82
<211> LENGTH: 216
<212> TYPE: PRT
<213> ORGANISM: Homo sapiens

<400> SEQUENCE: 82

Gln Ser Val Val Thr Gln Pro Pro Ser Val Ser Ala Ala Pro Gly Gln
1                   5                   10                  15

Lys Val Thr Ile Ser Cys Ser Gly Ser Asn Ser Asp Ile Gly Asn Asn
                    20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Ala Ile Thr Gly Leu Gln
65                  70                  75                  80

Ala Gly Asp Glu Ala Asp Tyr Tyr Cys Gly Thr Trp Leu Tyr Asp Arg
                    85                  90                  95

Ala Val Gly Leu Phe Gly Gly Gly Thr Lys Val Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190
```

-continued

```
Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 83
<211> LENGTH: 234
<212> TYPE: PRT
<213> ORGANISM: Homo sapiens
<220> FEATURE:
<223> OTHER INFORMATION: PB2452 VH with CH1

<400> SEQUENCE: 83

Gln Val Gln Leu Gln Glu Ser Gly Ala Glu Val Lys Lys Pro Gly Ser
1               5                   10                  15

Ser Val Arg Val Ser Cys Lys Ala Ser Gly Gly Thr Phe Asp Ser Tyr
        20                  25                  30

Ser Ile His Trp Val Arg Gln Ala Pro Gly Gln Gly Leu Glu Trp Met
        35                  40                  45

Gly Gly Ile Ile Pro Ala Phe Gly Thr Leu Ser Ser Ala Gln Asp Phe
    50                  55                  60

Gln Ala Arg Val Thr Ile Ser Ala Asp Lys Ser Thr Ser Thr Ala Tyr
65                  70                  75                  80

Met Glu Leu Ser Gly Leu Arg Ser Glu Asp Thr Ala Val Tyr Tyr Cys
            85                  90                  95

Ala Arg Gly Ser Phe Asp Tyr Tyr Phe Trp Ser Ala Ser His Pro Pro
            100                 105                 110

Asn Asp Ala Leu Ala Ile Trp Gly Gln Gly Thr Leu Val Thr Val Ser
            115                 120                 125

Ser Ala Ser Thr Lys Gly Pro Ser Val Phe Pro Leu Ala Pro Ser Ser
        130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys Asp Lys
225                 230

<210> SEQ ID NO 84
<211> LENGTH: 702
<212> TYPE: DNA
<213> ORGANISM: Homo sapiens
<220> FEATURE:
<223> OTHER INFORMATION: cDNA encoding PB2452 VH with CH1

<400> SEQUENCE: 84
caggttcaat tgcaagaaag cggtgcagaa gttaaaaaac cgggtagcag cgttcgtgtt        60
agctgtaaag caagcggtgg cacctttgat agctatagca ttcattgggt tcgtcaggca       120
ccgggtcagg gtctggaatg gatgggtggt attattccgg catttggcac cctgagcagc       180
gcacaggatt ttcaggcacg tgttaccatt agcgcagata aaagcaccag caccgcatat       240
```

-continued

--- atggaactga gcggtctgcg tagcgaagat accgcagtgt attattgtgc acgtggtagc      300
ttcgattatt acttttggag cgcaagccat ccgcctaatg atgcactggc aatttggggt      360
cagggcaccc tggttaccgt tagcagcgca agcaccaaag tccgagcgt ttttccgctg       420 gcaccgagca gcaaaagcac cagtggtggc accgcagcac tgggttgtct ggttaaagat      480
tattttccgg aaccggttac cgtgagctgg aatagcggtg cactgaccag cggtgttcat      540
acctttccgg cagttctgca gagcagcggt ctgtatagcc tgagcagcgt tgttaccgtt      600
ccgagcagca gcctgggcac ccagaccttat atttgtaatg ttaatcataa accgagcaat      660
accaaagtgg ataaacgtgt tgaaccgaaa agctgcgata aa                          702

<210> SEQ ID NO 85
<211> LENGTH: 216
<212> TYPE: PRT
<213> ORGANISM: Homo sapiens
<220> FEATURE:
<223> OTHER INFORMATION: PB2452 VL with CL

<400> SEQUENCE: 85

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Ala Gly Asp Glu Ala Asp Tyr Tyr Cys Gly Thr Trp Leu Tyr Asp Arg
                85                  90                  95

Ala Val Gly Leu Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 86
<211> LENGTH: 648
<212> TYPE: DNA
<213> ORGANISM: Homo sapiens
<220> FEATURE:
<223> OTHER INFORMATION: cDNA encoding PB2352 VL with CL

<400> SEQUENCE: 86
cagagcgttg tgacccagcc tccgagcgtt agcgcagctc cgggtcagaa agtgaccatt       60

-continued

```
agctgtagcg gtagcaatag cgatattggc aataactatg ttagctggta tcagcagctg      120
cctggcaccg caccgaaact gctgatttat gataataaca aacgtccgag cggtattccg      180
gatcgtttta gcggtagtaa aagcggcacc agcgcaaccc tggcaattac cggtctgcaa      240
gccggtgatg aagcagatta ttattgtggc acctggctgt atgatcgtgc agttggtctg      300
tttggtggtg gcaccaaagt taccgttctg ggtcagccga aagcagcacc gagcgttacc      360
ctgtttccgc ctagcagcga agaactgcag gcaaataaag caaccctggt ttgtctgatc      420
agcgattttt atccgggtgc agttaccgtt gcatggaaag cagatagcag tccggttaaa      480
gccggtgttg aaaccaccac cccgagcaaa cagagcaata acaaatatgc agcaagcagc      540
tatctgagcc tgacaccgga acagtggaaa agccatcgta gctatagctg tcaggttacc      600
catgaaggta gcaccgttga aaaaaccgtt gcaccgaccg aatgtagc                  648
```